US009192697B2

(12) United States Patent
Hoffmann et al.

(10) Patent No.: US 9,192,697 B2
(45) Date of Patent: Nov. 24, 2015

(54) BALLOON CATHETER FOR TREATING STENOSIS OF BODY PASSAGES AND FOR PREVENTING THREATENING RESTENOSIS

(75) Inventors: Erika Hoffmann, Eschweiler (DE); Roland Horres, Stolberg (DE); Volker Faust, Aachen (DE); Helmut Schreiber, Wurselen (DE); Armin Von Holst, Aachen (DE); Michael Hoffmann, Eschweiler (DE)

(73) Assignee: Hemoteq AG, Wurselen (DE)

( * ) Notice: Subject to any disclaimer, the term of this patent is extended or adjusted under 35 U.S.C. 154(b) by 247 days.

(21) Appl. No.: 13/023,594

(22) Filed: Feb. 9, 2011

(65) Prior Publication Data

US 2011/0160698 A1    Jun. 30, 2011

Related U.S. Application Data

(63) Continuation-in-part of application No. 12/307,261, filed as application No. PCT/DE2007/011173 on Jul. 3, 2007, now abandoned, application No. 13/023,594, which is a continuation-in-part of application No. 12/521,863, filed as application No. PCT/DE2008/000096 on Jan. 28, 2008, now Pat. No. 8,597,720.

(51) Int. Cl.
*A61L 29/16* (2006.01)
*A61M 25/10* (2013.01)

(52) U.S. Cl.
CPC ............ *A61L 29/16* (2013.01); *A61M 25/1029* (2013.01); *A61L 2300/41* (2013.01); *A61L 2300/416* (2013.01); *A61L 2300/42* (2013.01); *A61L 2300/426* (2013.01); *A61L 2300/80* (2013.01); *A61M 2025/1031* (2013.01); *A61M 2025/1075* (2013.01)

(58) Field of Classification Search
CPC ................ A61L 29/16; A61L 2300/41; A61L 2300/416; A61L 2300/42; A61M 25/1029
See application file for complete search history.

(56) References Cited

U.S. PATENT DOCUMENTS

| 304,121 | A | 8/1884 | Munch |
|---|---|---|---|
| 4,026,296 | A | 5/1977 | Stoy |
| 4,186,745 | A | 2/1980 | Lewis et al. |
| 4,364,392 | A | 12/1982 | Strother et al. |
| 4,481,323 | A | 11/1984 | Sterling |
| 4,490,421 | A | 12/1984 | Levy |
| 4,515,593 | A | 5/1985 | Norton |
| 4,589,873 | A | 5/1986 | Schwartz |
| 4,603,152 | A | 7/1986 | Laurin |
| 4,644,936 | A | 2/1987 | Schiff |
| 4,693,243 | A | 9/1987 | Buras |
| 4,733,665 | A | 3/1988 | Palmaz |
| 4,769,013 | A | 9/1988 | Lorenz |
| 4,784,647 | A | 11/1988 | Gross |
| 4,796,629 | A | 1/1989 | Grayzel |
| 4,800,882 | A | 1/1989 | Gianturco |
| 4,886,062 | A | 12/1989 | Wiktor |
| 4,906,244 | A | 3/1990 | Pinchuk et al. |
| 4,931,583 | A | 6/1990 | Hull et al. |
| 4,950,239 | A | 8/1990 | Gahara |
| 4,950,256 | A | 8/1990 | Luther |
| 4,994,033 | A | 2/1991 | Shockey et al. |
| 5,026,607 | A | 6/1991 | Kiezulas |
| 5,027,996 | A | 7/1991 | Fefeu |
| 5,041,100 | A | 8/1991 | Rowland |
| 5,049,131 | A | 9/1991 | Deuss |
| 5,087,244 | A | 2/1992 | Wolinsky et al. |
| 5,091,205 | A | 2/1992 | Fan |
| 2,098,381 | A | 3/1992 | Schneider |
| 5,092,841 | A | 3/1992 | Spears |
| 5,098,381 | A | 3/1992 | Schneider |
| 5,102,402 | A | 4/1992 | Dror et al. |
| 5,135,516 | A | 8/1992 | Sahatjian |
| 5,169,933 | A | 12/1992 | Anderson |
| 5,180,366 | A | 1/1993 | Woods |
| 5,199,951 | A | 4/1993 | Spears |
| 5,213,576 | A | 5/1993 | Abiuso et al. |
| 5,213,580 | A | 5/1993 | Slepian et al. |
| 5,232,444 | A | 8/1993 | Just et al. |
| 5,236,413 | A | 8/1993 | Feiring |
| 5,250,069 | A | 10/1993 | Nobuyoshi |
| 5,264,260 | A | 11/1993 | Saab |
| 5,270,086 | A | 12/1993 | Hamlin |
| 5,282,785 | A | 2/1994 | Shapland et al. |
| 5,286,254 | A | 2/1994 | Shapland et al. |

(Continued)

FOREIGN PATENT DOCUMENTS

| CA | 2363119 | 8/2000 |
|---|---|---|
| DE | 19908318 | 8/2000 |

(Continued)

OTHER PUBLICATIONS

Written Opinion for PCT/DE2008/000096.
International Preliminary Report on Patentability of International Application No. PCT/DE2007/001173 dated Aug. 4, 2009.
J. Wohrle et al., " Comparison of the heparin coated vs the uncoated Jostent- no influence on restenosis or clinical outcome" Europe Heart Journal (2001) vol. 22, pp. 1808-1816.
R. Charles, et al "Ceramide-Coated Balloon Catheters Limited Neointimal Hyperplasaia After Stretch Injury in Cartoid Arteries", Circ. Res. 2000, 87; 282-288.
D. Mastropaolo et al, "Crystal and molecular structure of paclitaxel (taxol)," Proc. Natl. Acad. Sci. USA, 92, pp. 6920-6924 (Jul. 1995).
U.S. Appl. No. 61/322,451, filed Apr. 9, 2010.

(Continued)

*Primary Examiner* — Suzanne Ziska
*Assistant Examiner* — Thurman Wheeler
(74) *Attorney, Agent, or Firm* — Walter Ottesen P.A.

(57) ABSTRACT

The present invention is directed to a method for coating catheter balloons with a defined amount of a pharmacologically active agent, wherein the coating method uses a coating device having a volume measuring device for releasing a measurable amount of a coating solution by means of a dispensing device specifically onto the surface of the catheter balloon.

5 Claims, 3 Drawing Sheets

(56) References Cited

U.S. PATENT DOCUMENTS

| | | | |
|---|---|---|---|
| 5,295,962 | A | 3/1994 | Crocker et al. |
| 5,304,121 | A | 4/1994 | Sahatjian |
| 5,318,531 | A | 6/1994 | Leone |
| 5,320,634 | A | 6/1994 | Vigil |
| 5,324,261 | A | 6/1994 | Amundson et al. |
| 5,328,468 | A | 7/1994 | Kaneko |
| 5,328,471 | A | 7/1994 | Slepian |
| 5,342,628 | A | 8/1994 | Picha |
| 5,344,400 | A | 9/1994 | Kaneko |
| 5,344,402 | A | 9/1994 | Crocker |
| 5,362,831 | A | 11/1994 | Mongelli |
| 5,368,566 | A | 11/1994 | Crocker |
| 5,370,614 | A | 12/1994 | Amundson et al. |
| 5,380,299 | A | 1/1995 | Fearnot |
| 5,383,928 | A | 1/1995 | Scott |
| 5,385,152 | A | 1/1995 | Abele |
| 5,405,472 | A | 4/1995 | Leone |
| 5,419,760 | A | 5/1995 | Narciso |
| 5,421,826 | A | 6/1995 | Crocker et al. |
| 5,425,703 | A | 6/1995 | Feiring |
| 5,427,767 | A | 6/1995 | Kresse et al. |
| 5,439,446 | A | 8/1995 | Barry |
| 5,443,496 | A | 8/1995 | Schwartz |
| 5,447,724 | A | 9/1995 | Helmus |
| 5,449,382 | A | 9/1995 | Dayton |
| 5,464,650 | A | 11/1995 | Berg |
| 5,470,307 | A | 11/1995 | Lindall |
| 5,489,525 | A | 2/1996 | Pastan |
| 5,498,238 | A | 3/1996 | Shapland et al. |
| 5,499,971 | A | 3/1996 | Shapland et al. |
| 5,500,180 | A | 3/1996 | Anderson |
| 5,542,926 | A | 8/1996 | Crocker |
| 5,545,208 | A | 8/1996 | Wolff |
| 5,549,603 | A | 8/1996 | Feiring |
| 5,554,119 | A | 9/1996 | Harrison et al. |
| 5,554,182 | A | 9/1996 | Dinh |
| 5,556,383 | A | 9/1996 | Wang et al. |
| 5,558,642 | A | 9/1996 | Schweich, Jr. et al. |
| 5,562,922 | A | 10/1996 | Lambert |
| 5,569,184 | A | 10/1996 | Crocker et al. |
| 5,569,463 | A | 10/1996 | Helmus |
| 5,571,089 | A | 11/1996 | Crocker |
| 5,578,075 | A | 11/1996 | Dayton |
| 5,588,962 | A | 12/1996 | Nicholas et al. |
| 5,599,306 | A | 2/1997 | Klein et al. |
| 5,599,307 | A | 2/1997 | Bacher et al. |
| 5,609,629 | A | 3/1997 | Fearnot et al. |
| 5,611,775 | A | 3/1997 | Machold et al. |
| 5,616,149 | A | 4/1997 | Barath |
| 5,624,411 | A | 4/1997 | Tuch |
| 5,626,862 | A | 5/1997 | Brem |
| 5,628,730 | A | 5/1997 | Shapland et al. |
| 5,629,008 | A | 5/1997 | Lee |
| 5,634,901 | A | 6/1997 | Alba |
| 5,637,086 | A | 6/1997 | Ferguson et al. |
| 5,651,986 | A | 7/1997 | Brem |
| 5,665,772 | A | 9/1997 | Cottens |
| 5,669,874 | A | 9/1997 | Feiring |
| 5,674,192 | A | 10/1997 | Sahatjian et al. |
| 5,674,241 | A | 10/1997 | Bley |
| 5,679,400 | A | 10/1997 | Tuch |
| 5,685,847 | A | 11/1997 | Barry |
| 5,688,516 | A | 11/1997 | Raad |
| 5,693,034 | A | 12/1997 | Buscemi et al. |
| 5,697,967 | A | 12/1997 | Dinh |
| 5,704,908 | A | 1/1998 | Hofmann et al. |
| 5,707,385 | A | 1/1998 | Williams |
| 5,716,981 | A | 2/1998 | Hunter |
| 5,728,066 | A | 3/1998 | Daneshvar |
| 5,733,925 | A | 3/1998 | Kunz |
| 5,766,158 | A | 6/1998 | Opolski |
| 5,769,883 | A | 6/1998 | Buscemi |
| 5,797,877 | A | 8/1998 | Hamilton |
| 5,800,538 | A | 9/1998 | Slepian et al. |
| 5,807,306 | A | 9/1998 | Shapland et al. |
| 5,810,763 | A | 9/1998 | Feiring |
| 5,833,657 | A | 11/1998 | Reinhardt et al. |
| 5,833,658 | A | 11/1998 | Levy |
| 5,843,089 | A | 12/1998 | Sahatjian et al. |
| 5,854,382 | A | 12/1998 | Loomis |
| 5,855,546 | A | 1/1999 | Hastings |
| 5,857,998 | A | 1/1999 | Barry |
| 5,865,801 | A | 2/1999 | Houser |
| 5,868,719 | A | 2/1999 | Tsukernik |
| 5,869,127 | A | 2/1999 | Zhong |
| 5,876,374 | A | 3/1999 | Alba |
| 5,893,840 | A | 4/1999 | Hull et al. |
| 5,900,246 | A | 5/1999 | Lambert |
| 5,902,266 | A | 5/1999 | Leone |
| 5,902,299 | A | 5/1999 | Jayaraman |
| 5,928,279 | A | 7/1999 | Shannon |
| 5,935,275 | A | 8/1999 | Burgard et al. |
| 5,935,506 | A | 8/1999 | Schmitz et al. |
| 5,947,977 | A | 9/1999 | Slepian et al. |
| 5,954,693 | A | 9/1999 | Barry |
| 5,954,706 | A | 9/1999 | Sahatjian et al. |
| 5,977,163 | A | 11/1999 | Li |
| 5,981,568 | A | 11/1999 | Krunz et al. |
| 6,048,356 | A | 4/2000 | Ravenscroft et al. |
| 6,048,515 | A | 4/2000 | Kresse et al. |
| 6,048,620 | A | 4/2000 | Zhong |
| 6,093,463 | A | 7/2000 | Thakrar |
| 6,099,454 | A | 8/2000 | Hastings |
| 6,099,926 | A | 8/2000 | Thakrar |
| 6,129,705 | A | 10/2000 | Grantz |
| 6,142,973 | A | 11/2000 | Carleton |
| 6,146,356 | A | 11/2000 | Wang et al. |
| 6,146,358 | A | 11/2000 | Rowe |
| 6,183,658 | B1 | 2/2001 | Lesniak et al. |
| 6,186,745 | B1 | 2/2001 | Johnson |
| 6,195,583 | B1 | 2/2001 | Feiring |
| 6,203,551 | B1 | 3/2001 | Wu |
| 6,218,016 | B1 | 4/2001 | Tedeschi et al. |
| 6,219,577 | B1 | 4/2001 | Brown, III et al. |
| 6,240,407 | B1 | 5/2001 | Chang |
| 6,245,103 | B1 | 6/2001 | Stinson |
| 6,262,107 | B1 | 7/2001 | Li |
| 6,270,522 | B1 | 8/2001 | Simhambhatla |
| 6,280,411 | B1 | 8/2001 | Lennox |
| 6,283,947 | B1 | 9/2001 | Mirzaee |
| 6,287,332 | B1 | 9/2001 | Bolz et al. |
| 6,296,619 | B1 | 10/2001 | Brisken et al. |
| 6,299,604 | B1 | 10/2001 | Ragheb |
| 6,306,166 | B1 | 10/2001 | Barry et al. |
| 6,344,028 | B1 | 2/2002 | Barry |
| 6,355,029 | B1 | 3/2002 | Joye et al. |
| 6,364,856 | B1 | 4/2002 | Ding et al. |
| 6,364,893 | B1 | 4/2002 | Sahatjian et al. |
| 6,369,039 | B1 | 4/2002 | Palasis et al. |
| 6,389,314 | B2 | 5/2002 | Feiring |
| 6,391,033 | B2 | 5/2002 | Ryan |
| 6,398,708 | B1 | 6/2002 | Hastings |
| 6,409,716 | B1 | 6/2002 | Sahatjian et al. |
| 6,418,448 | B1 | 7/2002 | Sarkar |
| 6,419,692 | B1 | 7/2002 | Yang et al. |
| 6,428,534 | B1 | 8/2002 | Joye et al. |
| 6,432,102 | B2 | 8/2002 | Joye |
| 6,440,990 | B1 | 8/2002 | Cottens |
| 6,443,941 | B1 | 9/2002 | Slepian et al. |
| 6,451,373 | B1 | 9/2002 | Hossainy |
| 6,468,297 | B1 | 10/2002 | Williams |
| 6,494,862 | B1 | 12/2002 | Ray |
| 6,506,408 | B1 | 1/2003 | Palasis |
| 6,511,477 | B2 | 1/2003 | Altman |
| 6,514,245 | B1 | 2/2003 | Williams |
| 6,524,274 | B1 | 2/2003 | Rosenthal et al. |
| 6,527,740 | B1 | 3/2003 | Jackson |
| 6,537,194 | B1 | 3/2003 | Winkler |
| 6,541,039 | B1 | 4/2003 | Lesniak et al. |
| 6,544,221 | B1 | 4/2003 | Kokish et al. |
| 6,544,223 | B1 | 4/2003 | Kokish |
| 6,545,097 | B2 | 4/2003 | Pinchuk et al. |
| 6,548,569 | B1 | 4/2003 | Williams et al. |
| 6,582,353 | B1 | 6/2003 | Hastings |

(56) References Cited

U.S. PATENT DOCUMENTS

| | | |
|---|---|---|
| 6,585,926 B1 | 7/2003 | Mirzaee |
| 6,592,548 B2 | 7/2003 | Jayaraman |
| 6,602,246 B1 | 8/2003 | Joye |
| 6,616,650 B1 | 9/2003 | Rowe |
| 6,623,452 B2 | 9/2003 | Chien et al. |
| 6,623,749 B2 | 9/2003 | Williams et al. |
| 6,638,246 B1 | 10/2003 | Naimark et al. |
| 6,645,135 B1 | 11/2003 | Bhat |
| 6,648,879 B2 | 11/2003 | Holland |
| 6,656,156 B2 | 12/2003 | Yang et al. |
| 6,663,880 B1 | 12/2003 | Roorda et al. |
| 6,682,545 B1 | 1/2004 | Kester |
| 6,685,648 B2 | 2/2004 | Flaherty |
| 6,699,272 B2 | 3/2004 | Slepian et al. |
| 6,706,013 B1 | 3/2004 | Bhat et al. |
| 6,730,105 B2 | 5/2004 | Shiber |
| 6,733,474 B2 | 5/2004 | Kusleika |
| 6,780,324 B2 | 8/2004 | Le Garrec et al. |
| 6,786,900 B2 | 9/2004 | Joye |
| 6,786,901 B2 | 9/2004 | Joye |
| 6,790,224 B2 | 9/2004 | Gerberding |
| 6,796,960 B2 | 9/2004 | Cioanta et al. |
| 6,805,898 B1 | 10/2004 | Wu |
| 6,811,550 B2 | 11/2004 | Holland |
| 6,838,493 B2 | 1/2005 | Williams et al. |
| 6,858,644 B2 | 2/2005 | Benigni et al. |
| 6,863,861 B1 | 3/2005 | Zhang (Ken) |
| 6,867,247 B2 | 3/2005 | Williams et al. |
| 6,890,339 B2 | 5/2005 | Sahatjian et al. |
| 6,890,583 B2 | 5/2005 | Chudzik et al. |
| 6,899,731 B2 | 5/2005 | Li et al. |
| 6,908,462 B2 | 6/2005 | Joye |
| 6,918,927 B2 | 7/2005 | Bates et al. |
| 6,923,996 B2 | 8/2005 | Epstein et al. |
| 6,939,320 B2 | 9/2005 | Lennox |
| 6,942,680 B2 | 9/2005 | Grayzel |
| 6,955,661 B1 | 10/2005 | Herweck et al. |
| 6,960,346 B2 * | 11/2005 | Shukla et al. ............ 424/400 |
| 6,972,015 B2 | 12/2005 | Joye |
| 6,991,647 B2 | 1/2006 | Jadhav |
| 6,995,661 B2 | 2/2006 | Amari |
| 7,005,414 B2 | 2/2006 | Barnikol et al. |
| 7,008,979 B2 | 3/2006 | Schottman et al. |
| 7,018,371 B2 | 3/2006 | Forman |
| 7,037,319 B2 | 5/2006 | Weber |
| 7,048,714 B2 | 5/2006 | Richter |
| 7,056,533 B2 | 6/2006 | Chudzik et al. |
| 7,060,051 B2 | 6/2006 | Palasis |
| 7,060,062 B2 | 6/2006 | Joye |
| 7,066,904 B2 | 6/2006 | Rosenthal et al. |
| 7,070,576 B2 | 7/2006 | Obrien |
| 7,081,112 B2 | 7/2006 | Joye |
| 7,090,655 B2 | 8/2006 | Barry |
| 7,105,175 B2 | 9/2006 | Schwarz |
| 7,108,684 B2 | 9/2006 | Farnan |
| 7,115,299 B2 | 10/2006 | Kokish |
| 7,150,738 B2 | 12/2006 | Ray |
| 7,160,317 B2 | 1/2007 | Mc Hale et al. |
| 7,166,098 B1 | 1/2007 | Steward et al. |
| 7,179,251 B2 | 2/2007 | Palasis |
| 7,232,486 B2 | 6/2007 | Keri |
| 7,241,455 B2 | 7/2007 | Richard |
| 7,247,338 B2 | 7/2007 | Pui |
| 7,279,002 B2 | 10/2007 | Shaw |
| 7,303,572 B2 | 12/2007 | Melsheimer |
| 7,306,625 B1 | 12/2007 | Stratford et al. |
| 7,323,189 B2 | 1/2008 | Pathak |
| 7,335,184 B2 | 2/2008 | Laguna |
| 7,357,940 B2 | 4/2008 | Richard et al. |
| 7,364,585 B2 | 4/2008 | Weber |
| 7,371,257 B2 | 5/2008 | Sahatjian et al. |
| 7,381,418 B2 | 6/2008 | Richard |
| 7,393,685 B1 | 7/2008 | Jordan |
| 7,402,172 B2 | 7/2008 | Chin et al. |
| 7,407,671 B2 | 8/2008 | McBride et al. |
| 7,407,684 B2 | 8/2008 | Spencer et al. |
| 7,459,169 B2 | 12/2008 | Nilsson et al. |
| 7,462,165 B2 | 12/2008 | Ding et al. |
| 7,470,252 B2 | 12/2008 | Mickley et al. |
| 7,473,242 B2 | 1/2009 | Donovan et al. |
| 7,491,188 B2 | 2/2009 | Holman et al. |
| 7,494,497 B2 | 2/2009 | Weber |
| 7,527,604 B2 | 5/2009 | Naimark |
| 7,553,292 B2 | 6/2009 | Kilpatrick et al. |
| 7,563,324 B1 | 7/2009 | Chen |
| 7,572,245 B2 | 8/2009 | Herweck et al. |
| 7,588,642 B1 | 9/2009 | Morris |
| 7,604,631 B2 | 10/2009 | Reynolds |
| 7,632,288 B2 | 12/2009 | Wu |
| 7,682,387 B2 | 3/2010 | Shulze et al. |
| 7,718,213 B1 | 5/2010 | Scheer |
| 7,731,685 B2 | 6/2010 | Ragheb |
| 7,744,644 B2 | 6/2010 | Weber et al. |
| 7,750,041 B2 | 7/2010 | Speck et al. |
| 7,753,876 B2 | 7/2010 | Cervantes |
| 7,758,892 B2 | 7/2010 | Chen et al. |
| 7,762,995 B2 | 7/2010 | Eversull |
| 7,767,219 B2 | 8/2010 | Weber et al. |
| 7,771,740 B2 | 8/2010 | Strickler et al. |
| 7,773,447 B2 | 8/2010 | Kajigaya |
| 7,794,751 B2 | 9/2010 | Chudzik et al. |
| 7,803,149 B2 | 9/2010 | Bates |
| 7,811,622 B2 | 10/2010 | Bates et al. |
| 8,291,854 B2 | 10/2012 | Behnisch |
| 8,414,910 B2 | 4/2013 | Wang |
| 2001/0020151 A1 | 9/2001 | Reed et al. |
| 2002/0010489 A1 | 1/2002 | Grayzel |
| 2002/0037358 A1 | 3/2002 | Barry et al. |
| 2002/0041898 A1 | 4/2002 | Unger |
| 2002/0042645 A1 | 4/2002 | Shannon |
| 2002/0098278 A1 | 7/2002 | Bates et al. |
| 2002/0151844 A1 | 10/2002 | Yang et al. |
| 2002/0183581 A1 | 12/2002 | Yoe et al. |
| 2003/0028210 A1 | 2/2003 | Boyle |
| 2003/0040712 A1 | 2/2003 | Ray et al. |
| 2003/0060877 A1 | 3/2003 | Falotico |
| 2003/0064965 A1 | 4/2003 | Richter |
| 2003/0077253 A1 | 4/2003 | Palasis |
| 2003/0083740 A1 | 5/2003 | Pathak |
| 2003/0114791 A1 | 6/2003 | Rosenthal et al. |
| 2003/0130717 A1 | 7/2003 | Hale et al. |
| 2003/0153870 A1 | 8/2003 | Meyer |
| 2003/0158517 A1 | 8/2003 | Kokish |
| 2003/0233068 A1 | 12/2003 | Jayaraman |
| 2003/0236513 A1 | 12/2003 | Schwarz et al. |
| 2003/0236514 A1 | 12/2003 | Schwarz |
| 2004/0023851 A1 | 2/2004 | Barnikol |
| 2004/0033251 A1 | 2/2004 | Sparer et al. |
| 2004/0034336 A1 | 2/2004 | Scott et al. |
| 2004/0039437 A1 | 2/2004 | Sparer et al. |
| 2004/0044308 A1 | 3/2004 | Naimark et al. |
| 2004/0044404 A1 | 3/2004 | Stucke et al. |
| 2004/0047911 A1 | 3/2004 | Lyu et al. |
| 2004/0059290 A1 | 3/2004 | Palasis |
| 2004/0064093 A1 | 4/2004 | Hektner et al. |
| 2004/0073284 A1 | 4/2004 | Bates et al. |
| 2004/0077948 A1 | 4/2004 | Violante et al. |
| 2004/0086569 A1 | 5/2004 | Sparer et al. |
| 2004/0098014 A1 | 5/2004 | Flugelman et al. |
| 2004/0098108 A1 | 5/2004 | Harder et al. |
| 2004/0106987 A1 | 6/2004 | Palasis et al. |
| 2004/0111144 A1 | 6/2004 | Lawin et al. |
| 2004/0115273 A1 | 6/2004 | Sparer et al. |
| 2004/0117222 A1 | 6/2004 | Rokosz |
| 2004/0127978 A1 | 7/2004 | Sparer et al. |
| 2004/0137066 A1 | 7/2004 | Jayaraman |
| 2004/0142011 A1 | 7/2004 | Nilsson et al. |
| 2004/0143287 A1 | 7/2004 | Konstantino |
| 2004/0175406 A1 | 9/2004 | Schwarz |
| 2004/0180039 A1 | 9/2004 | Toner et al. |
| 2004/0202691 A1 | 10/2004 | Richard |
| 2004/0210191 A1 | 10/2004 | Farnan |
| 2004/0215169 A1 | 10/2004 | Li |
| 2004/0219214 A1 | 11/2004 | Gravett et al. |

(56) References Cited

U.S. PATENT DOCUMENTS

| | | |
|---|---|---|
| 2004/0224003 A1 | 11/2004 | Schultz |
| 2004/0224080 A1 | 11/2004 | Epstein et al. |
| 2004/0230176 A1 | 11/2004 | Shanahan et al. |
| 2004/0234575 A1 | 11/2004 | Horres et al. |
| 2004/0260239 A1 | 12/2004 | Kusleika |
| 2005/0015046 A1 | 1/2005 | Weber et al. |
| 2005/0025801 A1 | 2/2005 | Richard et al. |
| 2005/0025802 A1 | 2/2005 | Richard et al. |
| 2005/0025803 A1 | 2/2005 | Richard et al. |
| 2005/0025848 A1 | 2/2005 | Huang |
| 2005/0027283 A1 | 2/2005 | Richard et al. |
| 2005/0037048 A1 | 2/2005 | Song |
| 2005/0037050 A1 | 2/2005 | Weber |
| 2005/0043678 A1 | 2/2005 | Freyman |
| 2005/0055077 A1 | 3/2005 | Marco et al. |
| 2005/0060028 A1 | 3/2005 | Horres et al. |
| 2005/0064005 A1 | 3/2005 | Dinh et al. |
| 2005/0064038 A1 | 3/2005 | Dinh et al. |
| 2005/0101522 A1 | 5/2005 | Speck et al. |
| 2005/0106206 A1 | 5/2005 | Herweck et al. |
| 2005/0129727 A1 | 6/2005 | Weber et al. |
| 2005/0129731 A1 | 6/2005 | Horres |
| 2005/0137618 A1 | 6/2005 | Kunis |
| 2005/0154416 A1 | 7/2005 | Herweck et al. |
| 2005/0158359 A1 | 7/2005 | Epstein et al. |
| 2005/0169969 A1 | 8/2005 | Li et al. |
| 2005/0176678 A1 | 8/2005 | Horres |
| 2005/0181015 A1 | 8/2005 | Zhong |
| 2005/0182361 A1 | 8/2005 | Lennox |
| 2005/0209548 A1 | 9/2005 | Dev |
| 2005/0215722 A1 | 9/2005 | Pinchunk et al. |
| 2005/0220853 A1 | 10/2005 | Dao et al. |
| 2005/0222677 A1 | 10/2005 | Bates et al. |
| 2005/0226991 A1 | 10/2005 | Hossainy et al. |
| 2005/0233061 A1 | 10/2005 | Schwarz |
| 2005/0244456 A1 | 11/2005 | Nilsson et al. |
| 2005/0244459 A1 | 11/2005 | DeWitt et al. |
| 2005/0246009 A1 | 11/2005 | Toner et al. |
| 2005/0251106 A1 | 11/2005 | Cervantes |
| 2005/0266083 A1 | 12/2005 | Shukla et al. |
| 2005/0273049 A1 | 12/2005 | Krulevitch |
| 2005/0273075 A1 | 12/2005 | Krulevitch |
| 2005/0278021 A1 | 12/2005 | Bates et al. |
| 2005/0288629 A1 | 12/2005 | Kunis |
| 2006/0002968 A1 | 1/2006 | Stewart |
| 2006/0002973 A1 | 1/2006 | Barry |
| 2006/0013853 A1 | 1/2006 | Richard |
| 2006/0013854 A1 | 1/2006 | Strickler et al. |
| 2006/0020243 A1 | 1/2006 | Speck et al. |
| 2006/0020331 A1 | 1/2006 | Bates et al. |
| 2006/0025848 A1 | 2/2006 | Weber et al. |
| 2006/0041225 A1 | 2/2006 | Wallace |
| 2006/0057208 A1 | 3/2006 | Holzer et al. |
| 2006/0058815 A1 | 3/2006 | Mickley et al. |
| 2006/0067977 A1 | 3/2006 | Labrecque et al. |
| 2006/0079836 A1 | 4/2006 | Holman et al. |
| 2006/0083768 A1 | 4/2006 | Labrecque et al. |
| 2006/0085058 A1 | 4/2006 | Rosenthal et al. |
| 2006/0088566 A1 | 4/2006 | Parsonage |
| 2006/0088596 A1 | 4/2006 | Labrecque |
| 2006/0112536 A1 | 6/2006 | Herweck et al. |
| 2006/0121081 A1 | 6/2006 | Labrecque et al. |
| 2006/0121088 A1 | 6/2006 | Hunter |
| 2006/0124056 A1 | 6/2006 | Behnisch et al. |
| 2006/0129093 A1 | 6/2006 | Jackson |
| 2006/0134160 A1 | 6/2006 | Troczynski et al. |
| 2006/0134168 A1 | 6/2006 | Chappa et al. |
| 2006/0135548 A1 | 6/2006 | Keri |
| 2006/0147491 A1 | 7/2006 | DeWitt et al. |
| 2006/0165754 A1 | 7/2006 | Ranade |
| 2006/0167407 A1 | 7/2006 | Weber et al. |
| 2006/0171982 A1 | 8/2006 | Timm |
| 2006/0171984 A1 | 8/2006 | Cromack et al. |
| 2006/0171985 A1 | 8/2006 | Richard et al. |
| 2006/0184112 A1 | 8/2006 | Horn |
| 2006/0190022 A1 | 8/2006 | Beyar et al. |
| 2006/0193890 A1 | 8/2006 | Owens |
| 2006/0193891 A1 | 8/2006 | Richard |
| 2006/0195176 A1 | 8/2006 | Bates et al. |
| 2006/0200048 A1 | 9/2006 | Furst |
| 2006/0200556 A1 | 9/2006 | Brave |
| 2006/0204537 A1 | 9/2006 | Ratner et al. |
| 2006/0212106 A1 | 9/2006 | Weber et al. |
| 2006/0224115 A1 | 10/2006 | Willard |
| 2006/0228452 A1 | 10/2006 | Cromack et al. |
| 2006/0240065 A1 | 10/2006 | Chen |
| 2006/0240070 A1 | 10/2006 | Cromack et al. |
| 2006/0280858 A1 | 12/2006 | Kokish |
| 2006/0286071 A1 | 12/2006 | Epstein et al. |
| 2006/0286141 A1 | 12/2006 | Campbell |
| 2007/0003599 A1 | 1/2007 | Schwarz |
| 2007/0020307 A1 | 1/2007 | Zhong et al. |
| 2007/0027523 A1 | 2/2007 | Toner et al. |
| 2007/0067882 A1 | 3/2007 | Atanasoska et al. |
| 2007/0078413 A1 | 4/2007 | Stenzel |
| 2007/0083149 A1 | 4/2007 | Steward et al. |
| 2007/0088246 A1 | 4/2007 | Steward et al. |
| 2007/0088255 A1 | 4/2007 | Toner et al. |
| 2007/0093745 A1 | 4/2007 | Steward et al. |
| 2007/0104766 A1 | 5/2007 | Wang |
| 2007/0106250 A1 | 5/2007 | Seward et al. |
| 2007/0106363 A1 | 5/2007 | Weber |
| 2007/0112330 A1 | 5/2007 | Palasis |
| 2007/0129474 A1* | 6/2007 | Salamone et al. ............ 524/261 |
| 2007/0129792 A1 | 6/2007 | Picart et al. |
| 2007/0150465 A1 | 6/2007 | Brave |
| 2007/0150466 A1 | 6/2007 | Brave |
| 2007/0150470 A1 | 6/2007 | Brave |
| 2007/0150515 A1 | 6/2007 | Brave |
| 2007/0150646 A1 | 6/2007 | Yoon |
| 2007/0154554 A1 | 7/2007 | Burgermeister et al. |
| 2007/0178136 A1 | 8/2007 | Arney |
| 2007/0185561 A1 | 8/2007 | Schmitz |
| 2007/0212386 A1 | 9/2007 | Patravale et al. |
| 2007/0212387 A1 | 9/2007 | Patravale et al. |
| 2007/0212393 A1 | 9/2007 | Patravale et al. |
| 2007/0212394 A1 | 9/2007 | Reyes et al. |
| 2007/0224234 A1 | 9/2007 | Steckel et al. |
| 2007/0225800 A1 | 9/2007 | Sahatjian et al. |
| 2007/0232996 A1 | 10/2007 | Andersen |
| 2007/0244548 A1 | 10/2007 | Myers et al. |
| 2007/0244549 A1 | 10/2007 | Pathak |
| 2007/0254010 A1 | 11/2007 | Richard |
| 2007/0255206 A1 | 11/2007 | Reneker |
| 2007/0292478 A1 | 12/2007 | Youri |
| 2008/0020013 A1 | 1/2008 | Reyes et al. |
| 2008/0021385 A1 | 1/2008 | Barry et al. |
| 2008/0027421 A1 | 1/2008 | Vancelette |
| 2008/0031173 A1 | 2/2008 | Zhang |
| 2008/0040314 A1 | 2/2008 | Brave |
| 2008/0050415 A1 | 2/2008 | Atanasoska et al. |
| 2008/0051541 A1 | 2/2008 | Strickler et al. |
| 2008/0057102 A1 | 3/2008 | Roorda |
| 2008/0071350 A1 | 3/2008 | Stinson |
| 2008/0071358 A1 | 3/2008 | Weber |
| 2008/0089958 A1 | 4/2008 | Diehl |
| 2008/0091008 A1 | 4/2008 | Viswanath |
| 2008/0095847 A1 | 4/2008 | Glauser et al. |
| 2008/0102033 A1 | 5/2008 | Speck et al. |
| 2008/0102034 A1 | 5/2008 | Speck et al. |
| 2008/0104004 A1 | 5/2008 | Brave |
| 2008/0113081 A1 | 5/2008 | Hossainy et al. |
| 2008/0114331 A1 | 5/2008 | Holman |
| 2008/0118544 A1 | 5/2008 | Wang |
| 2008/0132992 A1 | 6/2008 | Bates et al. |
| 2008/0140002 A1 | 6/2008 | Ramzipoor et al. |
| 2008/0145396 A1 | 6/2008 | Bates et al. |
| 2008/0145398 A1 | 6/2008 | Bates et al. |
| 2008/0157444 A1 | 7/2008 | Melsheimer |
| 2008/0171129 A1 | 7/2008 | Ranade et al. |
| 2008/0175887 A1 | 7/2008 | Wang |
| 2008/0195042 A1 | 8/2008 | Weber |
| 2008/0195079 A1 | 8/2008 | Moore et al. |
| 2008/0199506 A1 | 8/2008 | Horres |

(56) References Cited

U.S. PATENT DOCUMENTS

| | | |
|---|---|---|
| 2008/0206304 A1 | 8/2008 | Lindquist et al. |
| 2008/0208182 A1 | 8/2008 | Lafontaine |
| 2008/0220041 A1 | 9/2008 | Brito et al. |
| 2008/0249464 A1 | 10/2008 | Spencer et al. |
| 2008/0255508 A1 | 10/2008 | Wang |
| 2008/0255509 A1 | 10/2008 | Wang |
| 2008/0255510 A1 | 10/2008 | Wang |
| 2008/0274159 A1 | 11/2008 | Schultz |
| 2008/0276935 A1 | 11/2008 | Wang |
| 2008/0287984 A1 | 11/2008 | Weber et al. |
| 2008/0311173 A1 | 12/2008 | Schwarz et al. |
| 2009/0005849 A1 | 1/2009 | Hossainy et al. |
| 2009/0018501 A1 | 1/2009 | Yribarren et al. |
| 2009/0024200 A1 | 1/2009 | Wilcox et al. |
| 2009/0047414 A1 | 2/2009 | Corbeil et al. |
| 2009/0048667 A1 | 2/2009 | Mochizuki et al. |
| 2009/0054837 A1 | 2/2009 | Von Holst et al. |
| 2009/0069883 A1 | 3/2009 | Ding et al. |
| 2009/0076448 A1 | 3/2009 | Consigny et al. |
| 2009/0088735 A1 | 4/2009 | Abboud |
| 2009/0098176 A1 | 4/2009 | Helmus |
| 2009/0105686 A1 | 4/2009 | Snow et al. |
| 2009/0105687 A1 | 4/2009 | Deckman et al. |
| 2009/0111960 A1 | 4/2009 | Parsonage |
| 2009/0112239 A1 | 4/2009 | To |
| 2009/0120361 A1 | 5/2009 | Schiele |
| 2009/0136560 A1 | 5/2009 | Bates et al. |
| 2009/0192537 A1 | 7/2009 | Obrien |
| 2009/0204082 A1 | 8/2009 | Wesselmann et al. |
| 2009/0226502 A1 | 9/2009 | Chen |
| 2009/0227948 A1 | 9/2009 | Chen et al. |
| 2009/0227949 A1 | 9/2009 | Knapp et al. |
| 2009/0227980 A1 | 9/2009 | Kangas et al. |
| 2009/0246252 A1 | 10/2009 | Arps et al. |
| 2009/0254063 A1 | 10/2009 | Oepen et al. |
| 2009/0258049 A1 | 10/2009 | Klein et al. |
| 2009/0276036 A1 | 11/2009 | Nagura |
| 2009/0299355 A1 | 12/2009 | Bencini |
| 2009/0299356 A1 | 12/2009 | Watson |
| 2009/0318848 A1 | 12/2009 | Shippy, III et al. |
| 2010/0010470 A1 | 1/2010 | Bates |
| 2010/0015200 A1 | 1/2010 | McClain et al. |
| 2010/0023108 A1 | 1/2010 | Toner et al. |
| 2010/0030183 A1 | 2/2010 | Toner et al. |
| 2010/0036585 A1 | 2/2010 | Scharfenberg |
| 2010/0049294 A1 | 2/2010 | Zukowski et al. |
| 2010/0049296 A1 | 2/2010 | Sarasam et al. |
| 2010/0049309 A1 | 2/2010 | Bates et al. |
| 2010/0055294 A1 | 3/2010 | Wang et al. |
| 2010/0056985 A1 | 3/2010 | Weber et al. |
| 2010/0063585 A1 | 3/2010 | Hoffmann et al. |
| 2010/0069838 A1 | 3/2010 | Weber |
| 2010/0074934 A1 | 3/2010 | Hunter |
| 2010/0076542 A1 | 3/2010 | Orlowski |
| 2010/0087783 A1 | 4/2010 | Weber et al. |
| 2010/0092540 A1 | 4/2010 | Pinchuk et al. |
| 2010/0096781 A1 | 4/2010 | Huang et al. |
| 2010/0125239 A1 | 5/2010 | Perry et al. |
| 2010/0131043 A1 | 5/2010 | Casas et al. |
| 2010/0145266 A1 | 6/2010 | Orlowski |
| 2010/0179475 A1 | 7/2010 | Hoffmann et al. |
| 2010/0198190 A1 | 8/2010 | Michal et al. |
| 2010/0209471 A1 | 8/2010 | Weber |
| 2010/0209473 A1 | 8/2010 | Dhont et al. |
| 2010/0228333 A1 | 9/2010 | Drasler et al. |
| 2010/0233228 A1 | 9/2010 | Speck |
| 2010/0233236 A1 | 9/2010 | Zhao |
| 2010/0239635 A1 | 9/2010 | McClain |
| 2010/0249702 A1 | 9/2010 | Magana et al. |
| 2010/0256748 A1 | 10/2010 | Taylor |
| 2010/0261662 A1 | 10/2010 | Schreck et al. |
| 2010/0268191 A1 | 10/2010 | Trudel et al. |
| 2010/0272773 A1 | 10/2010 | Kangas et al. |
| 2010/0272778 A1 | 10/2010 | McClain |
| 2010/0285085 A1 | 11/2010 | Stankus et al. |
| 2010/0292641 A1 | 11/2010 | Wijay et al. |
| 2010/0298769 A1 | 11/2010 | Schewe et al. |
| 2010/0312182 A1 | 12/2010 | Adden et al. |
| 2010/0318020 A1 | 12/2010 | Atanasoska et al. |
| 2010/0324645 A1 | 12/2010 | Stankus et al. |
| 2010/0324648 A1 | 12/2010 | Scheller et al. |
| 2010/0331816 A1 | 12/2010 | Dadino et al. |
| 2010/0331947 A1 | 12/2010 | Shalev et al. |
| 2011/0008260 A1 | 1/2011 | Flanagan |
| 2011/0015664 A1 | 1/2011 | Kangas |
| 2011/0020151 A1 | 1/2011 | Tiefenthaler |
| 2011/0054396 A1 | 3/2011 | Kangas et al. |
| 2011/0054443 A1 | 3/2011 | Weber |
| 2011/0087191 A1 | 4/2011 | Scheuermann |
| 2011/0152765 A1 | 6/2011 | Weber |
| 2011/0160645 A1 | 6/2011 | Sutermeister |
| 2011/0160659 A1 | 6/2011 | Clarke |
| 2011/0160698 A1 | 6/2011 | Hoffmann |
| 2011/0178503 A1 | 7/2011 | Kangas |
| 2011/0196340 A1 | 8/2011 | Barry |
| 2011/0251590 A1 | 10/2011 | Weber |
| 2011/0270152 A1 | 11/2011 | Atanasoska |
| 2011/0275980 A1 | 11/2011 | Weber |
| 2011/0301565 A1 | 12/2011 | Weber |
| 2012/0059316 A1 | 3/2012 | Owens |
| 2012/0078227 A1 | 3/2012 | Kangas |
| 2012/0095396 A1 | 4/2012 | Radhakrishnan |
| 2012/0231037 A1 | 9/2012 | Levi |
| 2013/0035483 A1 | 2/2013 | Zeng |
| 2013/0053947 A1 | 2/2013 | Kangas |

FOREIGN PATENT DOCUMENTS

| | | |
|---|---|---|
| DE | 102004020856 | 4/2005 |
| EP | 0383429 | 1/1990 |
| EP | 0372088 | 6/1990 |
| EP | 0379156 | 7/1990 |
| EP | 0399712 | 11/1990 |
| EP | 0470246 | 2/1991 |
| EP | 0551182 | 7/1993 |
| EP | 0734721 | 3/1996 |
| EP | 0747069 | 4/1996 |
| EP | 0519063 | 5/1996 |
| EP | 0712615 | 5/1996 |
| EP | 0717041 | 6/1996 |
| EP | 0770401 | 5/1997 |
| EP | 0633796 | 11/1997 |
| EP | 0950386 | 10/1999 |
| EP | 0937469 | 10/2000 |
| EP | 0623354 | 10/2002 |
| EP | 0568310 | 11/2003 |
| EP | 1189553 | 3/2004 |
| EP | 1407726 | 4/2004 |
| EP | 1521603 | 4/2005 |
| EP | 1667760 | 6/2006 |
| EP | 1372737 | 12/2006 |
| EP | 1810665 | 7/2007 |
| EP | 1666071 | 8/2007 |
| EP | 1666070 | 9/2007 |
| EP | 1857127 | 11/2007 |
| EP | 1539266 | 4/2008 |
| EP | 1981559 | 10/2008 |
| EP | 1996246 | 12/2008 |
| EP | 2043704 | 4/2009 |
| EP | 2108390 | 10/2009 |
| EP | 2125058 | 12/2009 |
| EP | 2125060 | 12/2009 |
| EP | 1594459 | 2/2010 |
| EP | 1669092 | 3/2010 |
| EP | 2172242 | 4/2010 |
| EP | 1534356 | 7/2010 |
| EP | 1786487 | 11/2010 |
| EP | 2251050 | 11/2010 |
| EP | 2241341 | 1/2011 |
| GB | 2112646 | 7/1983 |
| GB | 2127839 | 9/1983 |
| JP | 663145 | 3/1994 |
| JP | 663145 A | 3/1994 |
| JP | 2002240847 | 8/2002 |

(56) References Cited

FOREIGN PATENT DOCUMENTS

| | | |
|---|---|---|
| RU | 200513564 | 4/2004 |
| WO | 8912478 | 12/1989 |
| WO | 9108790 | 6/1991 |
| WO | 9211896 | 7/1992 |
| WO | 9215286 | 9/1992 |
| WO | 9306792 | 4/1993 |
| WO | 9421308 | 9/1994 |
| WO | 9423787 | 10/1994 |
| WO | 9503036 | 2/1995 |
| WO | 9503083 | 2/1995 |
| WO | 9508305 | 3/1995 |
| WO | 9521636 | 8/1995 |
| WO | 9625176 | 8/1996 |
| WO | 9632907 | 10/1996 |
| WO | 9639949 | 12/1996 |
| WO | 9710011 | 3/1997 |
| WO | 97025085 | 7/1997 |
| WO | 9733552 | 9/1997 |
| WO | 9741916 | 11/1997 |
| WO | 9831415 | 7/1998 |
| WO | 9901458 | 1/1999 |
| WO | 9908729 | 2/1999 |
| WO | 9916500 | 4/1999 |
| WO | 9925336 | 5/1999 |
| WO | 9929353 | 6/1999 |
| WO | 0032238 | 6/2000 |
| WO | 0032267 | 6/2000 |
| WO | 0045744 | 8/2000 |
| WO | 0149358 | 7/2001 |
| WO | 0160441 | 8/2001 |
| WO | 0238065 | 5/2002 |
| WO | 0243796 | 6/2002 |
| WO | 02076509 | 10/2002 |
| WO | 03022265 | 3/2003 |
| WO | 03026718 | 4/2003 |
| WO | 03/039612 | 5/2003 |
| WO | 03059430 | 7/2003 |
| WO | 03094991 | 11/2003 |
| WO | 2004028582 | 4/2004 |
| WO | 2004028610 | 4/2004 |
| WO | 2004050140 | 6/2004 |
| WO | 2004060346 | 7/2004 |
| WO | 2004060471 | 7/2004 |
| WO | 2004089958 | 10/2004 |
| WO | 2004091684 | 10/2004 |
| WO | 2005027994 | 3/2005 |
| WO | 2005027996 | 3/2005 |
| WO | 2005032611 | 4/2005 |
| WO | 2005/082434 | 9/2005 |
| WO | 2006036970 | 4/2006 |
| WO | 2006102359 | 9/2006 |
| WO | 2006108420 | 10/2006 |
| WO | 2006116348 | 11/2006 |
| WO | 2006116989 | 11/2006 |
| WO | 2006130326 | 12/2006 |
| WO | 2007011707 | 1/2007 |
| WO | 2007090382 | 8/2007 |
| WO | 2007090385 | 8/2007 |
| WO | 2008003298 | 1/2008 |
| WO | 2008014222 | 1/2008 |
| WO | 2008045228 | 4/2008 |
| WO | 2008086794 | 7/2008 |
| WO | 2008089730 | 7/2008 |
| WO | 2008101486 | 8/2008 |
| WO | 2007109114 | 9/2008 |
| WO | 2008109114 | 9/2008 |
| WO | 2008125890 | 10/2008 |
| WO | 2008137237 | 11/2008 |
| WO | 2009002855 | 12/2008 |
| WO | 2009014692 | 1/2009 |
| WO | 2009018816 | 2/2009 |
| WO | 2009026914 | 3/2009 |
| WO | 2009036118 | 3/2009 |
| WO | 2009036135 | 3/2009 |
| WO | 2009066330 | 5/2009 |
| WO | 2009100394 | 8/2009 |
| WO | 2009120361 | 10/2009 |
| WO | 2009121565 | 10/2009 |
| WO | 2009135125 | 11/2009 |
| WO | 2010009335 | 1/2010 |
| WO | 2010021757 | 2/2010 |
| WO | 2010026578 | 3/2010 |
| WO | 2010079218 | 7/2010 |
| WO | 2010080575 | 7/2010 |
| WO | 2010086863 | 8/2010 |
| WO | 2010096476 | 8/2010 |
| WO | 2010111232 | 9/2010 |
| WO | 2010120620 | 10/2010 |
| WO | 2010124098 | 10/2010 |
| WO | 2010146096 | 12/2010 |
| WO | 2010147805 | 12/2010 |
| WO | 2011009096 | 1/2011 |
| WO | 2011028419 | 3/2011 |
| WO | 2011097103 | 8/2011 |

OTHER PUBLICATIONS

U.S. Appl. No. 61/330,201, filed Apr. 30, 2010.
U.S. Appl. No. 61/332,544, filed Apr. 9, 2010.
U.S. Appl. No. 61/352,117, filed Jun. 7, 2010.
U.S. Appl. No. 61/379,608, filed Sep. 2, 2010.
U.S. Appl. No. 61/385,849, filed Sep. 23, 2010.
U.S. Appl. No. 61/394,104, filed Oct. 18, 2010.
U.S. Appl. No. 61/421,054, filed Dec. 8, 2010.
Abstract from Liggins, R. T., Hunter, W. L and Burt, H. M. 'Solid-state characterization of paclitaxel.' Journal of Pharmaceutical Sciences, 86: 1458-1463, (1997).
Abstracts from the 70th Scientific Sessions, Orange County Convention center, Orlando, Florida, Nov. 9-12, 1997, Supplement to Circulation, vol. 96, No. 8, Supplement I, 1-341,1-288 and 1-608.
Alexis et al., 'In vitro study of release mechanisms of paclitaxel and rapamycin from drug-incorporated biodegradable stent matrices' Journal of Controlled Release 98 (2004) 67-74.
Axel, Dorothea I., et al., Paclitaxel Inhibits Arterial Smooth Muscle Cell Proliferation and Migration In Vitro and In Vivo Using Local Drug Delivery, Jul. 15, 1997, vol. 96 (2), 636-651.
Axel De Labriolle et al., "Paclitaxel-eluting balloon: From bench to bed", Catheterization and Cardiovascular Interventions, vol. 73. No. 5, Apr. 1, 2009, pp. 643-652.
Buvardi, S., et al., 'Merck Index', 1996, Merck and Co., p. 144.
Cardiovascular and Interventional Radiology, Supplement 1, Sep. 28-Oct. 2, 1997, 158-161.
Consigny PM, Barry JJ, Vitali NJ.; 'Local Delivery of an Antiproliferative Drug with Use of Hydrogel-coated Angioplasty Balloons1' J Vasc Intery Radiol. Jul.-Aug. 1994;5(4):553-60.
Cortese et al., "Paclitaxel-coated balloon versus drug-eluting stent during PCI of small coronary vessels, a prospective randomised clinical trial. The PICCOLETO Study", Heart 2010; 96:1291-1296.
Finkelstein et al., "Local Drug Delivery via a Coronary Stent with Programmable Release Pharmocokinetics," 2003, Circulation, 107, 777-784.
Partial European Search Report in EP 07005256.8, dated Jan. 25, 2008.
PCT/US 08/72660 Search Report, Nov. 6, 2008.
PCT/US 2005/47235 Search Report, Dec. 28, 2005.
Presentation by Dr. Cortese, "Paclitaxel-eluting balloon versus paclitaxel-eluting stent in small coronary vessel disease." The Piccoleto Trial.
Scheller et al., "Treatment of Coronary In-Stent Restenosis with a Paclitaxel-Coated Balloon Catheter", The New England Journal of Medicine, 2006; 355:2113-24.
Scollott, S.J., et al., Taxol Inhibits Neointimal Smooth Muscle Cell Accumulation after Angioplasty in the Rat, 1995, Journal of Clinical Investigation, 95, pp. 1869-1876.
Westedt et al., "Paclitaxel releasing films consisting of poly(vinyl alcohol)-graft-poly(lactide-co-glycolide) and their potential as biodegradable stent coatings." 2006, J Control Release 111, 235-46 (abstract).

(56) References Cited

OTHER PUBLICATIONS

Xu et al., "Lactic-co-glycolic acid polymer with rapamycin coated stent reduces neo-intimal formation in a porcine coronary model", Journal of Clinical Cardiology, 2004, abstract.

Dowding et al., "Preparation and Swelling Properties of Poly(NIPAM) "Minigel" Particles Prepared by Inverse Suspension Polymerization," Journal of Colloid and Interface Science 221, 268-272 (2000).

Panda et al., "Synthesis and swelling characteristics of poly(N-isopropylacrylamide) temperature sensitive hydrogels crosslinked by electron beam irradiation," Radiation Physics and Chemistry 58 (2000) 101-110.

U.S. Appl. No. 61/394,104, filed Oct. 18, 2010; Inventor: Radhakrishnan et al.

Scheller et al., "A further alternative; Balloons can be coated, as well" Newsletter from annual meeting in DGK Apr. 21, 2006.

Mondesire (Targeting Mammalian Target of Rapamycin Synergistically Enhances Chemotherapy-Induced Cytotoxicity in Breast Cancer Cells, 10 Clin. Cancer Res. 7031 (2004).

Joner, et al., Comparative assessment of drug-eluting balloons in an advanced porcine model of coronary restenosis, Thrombosis and Haemostasis 105.5/2011, Prepublished online Feb. 8, 2011.

Radke, et al., Vascular effects of paclitaxel following drug-eluting balloon angioplasty in a porcine coronary model: the importance of excipients, EuroIntervention 7: 730-737, 2011.

Farb, et al., Pathological Analysis of Local Delivery of Paclitaxal Via a Polymer-Coated Stent, Circulation, 473-479, Jul. 24, 2001.

Drachman, et al., Neointimal Thickening After Stent Delivery of Paclitaxel: Change in Composition and Arrest of Growth Over Six Months, Journal of the American College of Cardiology, vol. 36, No. 7, 2325-2332, Dec. 2000.

* cited by examiner

BALLOON CATHETER FOR TREATING STENOSIS OF BODY PASSAGES AND FOR PREVENTING THREATENING RESTENOSIS

CROSS-REFERENCE TO RELATED APPLICATIONS

The present application is a continuation-in-part of U.S. application Ser. No. 12/307,261, filed Apr. 10, 2009, now abandoned published as US 2010/0063585, which is a US National Stage application of PCT Application No. PCT/DE07/01173, filed Jul. 3, 2007, designating the US. The present application is also a continuation-in-part of U.S. application Ser. No. 12/521,863, filed Mar. 22, 2010, now U.S. Pat. No. 8,597,720 published as US 2010/0179475, which is a US National Stage application of PCT Application No. PCT/DE08/000,096, filed Jan. 21, 2008, designating the US. PCT Application Nos. PCT/DE07/01173 and PCT/DE08/000,096, and the corresponding U.S. application Ser. Nos. 12/307,261 and 12/521,863, are all expressly incorporated herein by reference in their entirety.

DESCRIPTION

The present invention is directed to medical devices having short-term contact with the organism, as e.g. balloon catheters coated with at least one layer containing at least one antiproliferative, immunosuppressive, anti-angiogenic, anti-inflammatory, fungicidal and/or anti-thrombotic agent, methods for manufacturing these substance-releasing application aids and the use of these medical devices for the prevention of restenoses of the affected corporal lumina.

Since the end of the 80ies of the last century metallic tubular stent grafts adjusted to the corporal lumen have been established ever the more for the prevention of restenosis, i.e. the prevention of re-occlusion of vessels, the graft pressing from the inside against the vascular wall. Further development of these grafts known as stents to a drug-coated "drug eluting stents" is intensively pursued at the time because of positive results in minimizing restenosis rates in comparison with uncoated stents.

These long-term implants substituted continuously PCTA (percutaneous transluminal coronary angioplasty) carried out since the 60ies and nowadays occupy the major part of interventions performed, since re-occlusion rates of uncoated stents are in several cases lower than occlusions recurring after PCTA performance.

Successfully realised in drug eluting stents, the idea of combining mechanical and chemical prophylaxis was already investigated since the early days of stents in balloon catheters for preventing restenosis of coronary arteries and used in different varieties in clinical studies.

The drug-loaded balloon catheter, however, could not prevail over the stent. The reasons are obvious:

In PCTA the occluded part is enlarged for a short time of 1 to 3 minutes by means of an inflatable balloon at the catheter tip, if necessary repeated for more than two times. Herein the vessels must be overstretched in such a way that the occlusion is removed. From this procedure microlesions result in the vascular wall reaching up to the adventitia. After removing the catheter the lesioned vessel is left alone so that considerably high performance is required for the healing process, in dependence of the inflicted lesion grade resulting from the duration, the repetitions and the grade of overstretching. This is reflected in the high re-occlusion rate after PCTA.

In stent implantation the balloon catheter is used as a transport and implant aid so that also herein overstretching of the vascular wall occurs, but in this case overstretching is only needed for the time of stent dilation. If the stent is unalterably stuck in the correct position the balloon is deflated again and can be removed. Thus the time of the once overstretch is reduced. The reduction in restenosis rate shows that this reduced overstretch time and the likewise reduced degree of overstretching in stents can lead already to a reduced rate in post-treatment, despite of introducing exogenous material into the body. This promising advance didn't leave much space for further optimizing PCTA since there was confidence that stents as permanent implants are hopeful carriers of a new preferably restenosis-free era which led to a preferential use down to the present day. PTCA is only performed in less severe cases and in particularly severe cases ahead of a stent implantation. The next goal in stent history is the 100% sure prevention of restenosis. Therefore the search for the combination of an ideal drug and an ideal preferably biodegradable stent has set out. Suppression of cellular reactions is mainly accomplished during the first days and weeks by means of preferably antiproliferative, immunosuppressive and/or antiphlogistic agents and their likewise active derivatives/analogues and metabolites. The active agents and/or combinations of active agents are used herein in a sensible way for wound healing or for its support.

The improvements balloon catheters have undergone recently were related up to now mainly to the ability of placing a stent precisely and safely. PCTA as an independent method was widely replaced.

But when using PCTA there are advantages over the stent, not least because thus at no time after performing the treatment an exogenous object is present in the organism as an additional stress factor or initiator of sequelae as is restenosis. Therefore there are up to now links to the studies on drug-releasing balloon catheters carried out in the late 80ies.

Thus different embodiments of balloon catheters were described for example, in which the outer surface being in direct contact with the environment has openings through which an active agent liquid or solved under pressure during dilation is pressed against the vascular wall (e.g. in U.S. Pat. Nos. 5,087,244, 4,994,033, 4,186,745).

For example, EP 0 383 429 A discloses a balloon catheter with tiny openings trough which a heparin solution is released to the vascular wall during dilation.

Several disadvantages as a lower uptake of the active agent into the vascular wall, missing control on dosage, problems with the balloon material etc. have kept the option of an exogenous object-free treatment of stenoses in suspense. Coating balloons analogous to stents with active agents with or without a polymeric matrix caused also problems, on the one hand in the short contact time and consequently a lower substance release from the catheter to its environment, and on the other hand in the considerable difficulties to bring the coating on the balloon unscathed to its destination, before and during dilation.

Only recently a substance releasing balloon catheter became an alternative to stents (CardioNews Letter, Apr. 21, 2006). It involves a balloon catheter dipped into a solution of paclitaxel and a radiocontrast medium which led in a one year clinical study to a reduction in restenosis rate from 40 to 9%, in comparison to an uncoated balloon catheter. For example, such a balloon catheter is disclosed in WO 2004 28582 A1. Though these first results seem to be promising typical problems of such a treatment haven't been overcome.

In any case the optical resolution reached by the coating with a contrast medium is favourable, but the amount of the active agent effectively released and taken up at the site of action after PTCA performance remains individual and uncontrolled, since already after introducing the balloon catheter into the bloodstream starting from the groin to the heart an unquantifiable portion of the coating comes off. Additionally, also during balloon dilation further parts of the coating crumble away and are carried away from the surface by the bloodstream. Consequently, a part of the concentration of the active agent applied to the balloon catheter doesn't reach the affected site, but can be regarded simply as an ineffective intravenous administration. The amount of the lost portion can't be controlled and thus is not available for an optimal provision at the affected site. What is left on the balloon catheter must be sufficient for achieving a promising therapy, but the question remains how much substance actually reaches its target and is absorbed from the vascular wall.

Thus the alternative of a stent free restenosis treatment with this balloon catheter shall be brought on a new, effective and controllable road.

Furthermore, the conventional method of dip or spray coating for catheter balloons has the great disadvantage that it can never be determined how much substance actually was applied to the balloon surface which basically leads to a clear overdosage. Moreover it becomes ever the more important in regulatory affairs and for attaining marketing authorizations to provide well defined balloon coatings for which the substance amount was exactly determined. Conventional methods of dipping the balloon catheter several times in a coating solution or of exposing the balloon to a spray stream or mist of the coating solution didn't yield reproducible results, so that the application of a defined substance amount was not possible.

The objective of the present invention consists in providing a coating method for balloon catheters in which the amount of the applied coating and thus the amount of the applied substance can be exactly determined.

A further objective of the present invention is to provide a substance releasing balloon catheter and other medical devices for short-term use in the organism which ensure a controlled and optimal substance transfer to and into the vascular wall during short term exposure in order to induce a positive healing process.

It must be ensured therefor that on the one hand the active agent is not washed of from the medical device by body fluid on its way to the target site or is crumbled away at the latest when being dilated and thus an undefined respectively insufficient substance amount reaches the target. On the other hand the strongly limited exposure time must be sufficient to transfer the substance in a determined dosage from the catheter onto respectively into the vascular wall.

This task is solved by the teaching of the independent claims of the present invention. Further advantageous embodiments of the invention arise from the dependent claims, the description and the examples.

According to the invention the objective is solved by special coating methods for balloon catheters coating the balloon catheters with a defined amount of a pharmacologically active agent wherein the coating method uses a coating device with a volume measuring system for releasing a measurable amount of a coating solution by means of a release device specifically to the surface of the balloon catheter.

As a volume measuring system any device can be used which is able to provide a measured amount of coating solution or to measure or to display the amount of released coating solution. Volume measuring systems simplest are gamuts, scaled pipettes, scaled burettes, scaled containers, scaled cavities as well as pumps, valves, syringes or other piston-shaped containers able to provide, transport or release a measured amount of coating solution. Thus the volume measuring system only serves to provide or release a certain amount of coating solution or to measure and/or display the released amount of coating solution. Thus the volume measuring system serves to determine respectively to measure the amount of coating solution transferred from the release device to the surface of the balloon catheter and this the substance amount.

The coating solution contains at least one pharmacologically active agent together with at least one transport agent, citrate ester, contrast medium, polymer, polysaccharide, peptide, nucleotide, oil, fat, wax, fatty acid, fatty acid ester, hydrogel, salt, solvent, pharmacologically acceptable adjuvant or a mixture of aforesaid substances. Possible ingredients of the coating solution are described herein in detail.

The key component of the coating device is, however, the release device which can be realized as a nozzle, a plurality of nozzles, a thread, a mesh of threads, a piece of textile, a leather strip, a sponge, a ball, a syringe, a needle, a cannula or a capillary. According to the embodiment of the release device result some modifiable coating methods all based on the principle of transferring a measurable or predetermined but known substance amount to the surface of the balloon catheter thus yielding a coating with a defined substance concentration or amount and providing a reproducible coating with small deviations, something the conventional dip or spray methods didn't allow. For differentiating the methods certain term are used herein, as squirting method, pipetting method, capillary method, fold spray method, drag method, thread drag method or roll method, which are the preferred embodiments of the present invention.

Not only a method according to the invention but also a device according to the invention results from the use of a ball as a releasing device. The corresponding method is termed herein as roll method and the corresponding device has a ball with a lead for the coating solution to the ball. By means of a control, preferably an optical control, the ball is contacted to the surface of the catheter balloon. Through a valve or because of the pressure of the balloon surface on the ball the coating solution flows out of a cavity or a volume measuring system onto the ball. The ball is rolled over the surface of the catheter balloon and thus drives off the surface of the catheter balloon, wherein the coating solution added to the ball is transferred from the ball to the surface of the catheter balloon.

By means of such a device and with this roll method catheter balloons can be completely or only partially coated in the deflated or inflated state. For example, a catheter balloon can be specifically driven off and coated in the inflated or partially inflated state in the region of the widened folds, wherein the coating remains onside the folds after deflation (i.e. folding up), so that thus a specific coating of the folds can be achieved. In order to avoid that the ball damages the balloon respectively the balloon material this material is preferably rubber-like as e.g. caoutchouc or other polymers.

Other preferred coating methods are referred to in detail further down.

The present invention is directed particularly to coated catheter balloons with a substance releasing coating.

As catheter balloons conventional catheter balloons, bifurcation balloons as well as fold balloons or special balloons can be used.

The term catheter balloons respectively conventional catheter balloons refers to such dilatable catheter balloons which usually serve to place a stent by means of dilation. Furthermore, it refers also to non-dilatable catheter balloons for stent placement suitable for self-expanding stents and carrying a removable wrapper on the stent for avoiding premature stent expansion.

Expandable and recompressible catheter balloons with a wrapper as in non-dilatable catheter balloons for self-expanding stents are, however, usually used without a stent in order to protect the coating on the catheter balloon from premature removal.

Bifurcation balloons refer to catheter balloons for treating a bifurcation of a vessel, especially of a blood vessel. Such balloons may have two arms or consist of two combined or two separate balloons being used contemporarily or consecutively for the treatment of a vessel bifurcation respectively the placement of one or two stents in a vessel bifurcation or in the immediate proximity of a vessel bifurcation.

Fold balloons refer to balloons as described for example in EP 1189553 B1, EP 0519063 B1, WO 03/059430 A1 and WO 94/23787 A1, having "folds" in the compressed state of the balloon that open at least partially when expanding the balloon.

Special balloons refer to balloons with pores, particularly micropores, allowing liquids and solutions to pass through during expansion or on applying pressure. Such a balloon with micropores is disclosed in EP 383 429 A. Moreover, the term special balloon refers to balloons with an especially designed surface with microneedles described in WO 02/043796 A2 or to the catheter balloon disclosed in WO 03/026718 A1 with a micro raw or nano raw surface for embedding active agents with or without carrier substances.

The term balloon or catheter balloon basically refers to every expandable and recompressible as well as temporarily inflatable medical device usually used together with a catheter.

The coated balloons according to the invention can be used without a stent or with a crimped stent. Their use is not limited to a first treatment of stenotic vessels but they are also particularly useful to combat successfully an occurring restenosis (e.g. in-stent-restenosis) and a recurrent re-occlusion.

The catheter balloon can consist of current materials, especially polymers as described further down, and particularly of polyamide as e.g. PA 12, polyester, polyurethane, polyacrylates, polyethers and so on.

The stent may consist likewise of current materials a for example medical stainless steel, titanium, chrome, vanadium, tungsten, molybdenum, gold, Nitinol, magnesium, iron, alloys of aforesaid metals as well as polymeric material as e.g. chitosan, heparanes, polyhydroxybutyrates (PHB), polyglycerides, polylactides and copolymers of the aforesaid materials.

Preferably the coated catheter balloons according to the invention are used without an attached stent, but the use with a crimped stent is possible also. If apart of the coated balloon an attached crimped stent is used the stent may be bare or likewise coated wherein the stent may have a different coating and also a different active agent than the coating of the catheter balloon.

The term coating shall comprise not only a coating of the surface of the catheter balloon but also a filling or coating of folds, cavities, pores, microneedles or other fellable spaces on, between or in the balloon material.

The coating may be applied in one or more steps, have one or more layers, consist of one material or a composition of different active agents and contain preferably one or more active agents. As active agents respectively combinations of active agents anti-inflammatory, cystostatic, cytotoxic, antiproliferative, anti-microtubuli, anti-angiogenic anti-restenotic (anti-restenosis), antifungicide, antineoplastic, antimigrative, athrombogenic or antithrombogenic substances are suitable.

As further anti-inflammatory, cystostatic, cytotoxic, antiproliferative, anti-microtubuli, anti-angiogenic ant i-restenotic, antifungicide, antineoplastic, antimigrative, athrombogenic or antithrombogenic substances can be used preferably: vasodilators, sirolimus (rapamycin), somatostatin, tacrolimus, roxithromycin, dunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoposide, teniposide, nimustine, carmustine, lomustine, cyclophosphamide, 4-hydroxycyclophosphamide, estramustine, melphalan, ifosfamide, trofosfamide, chlorambucil, bendamustine, dacarbazine, busulfan, procarbazine, treosulfan, temozolomide, thiotepa, daunorubicin, doxorubicin, aclarubicin, epirubicin, mitoxantrone, idarubicin, bleomycin, mitomycin, dactinomycin, methotrexate, fludarabine, fludarabine-5'-dihydrogenephosphate, cladribine, mercaptopurine, thioguanine, cytarabine, fluorouracil, gemcitabine, capecitabine, docetaxel, carboplatin, cisplatin, oxaliplatin, amsacrine, irinotecan, topotecan, hydroxycarbamide, miltefosine, pentostatin, aldesleukin, tretinoin, asparaginase, pegaspargase, anastrozole, exemestane, letrozole, formestane, aminoglutethimide, adriamycin, azithromycin, spiramycin, cepharantin, 8-□-ergoline, dimethylergoline, agroclavin, 1-allylisurid, 1-allyltergurid, bromergurid, bromocriptin (ergotaman-3',6',18-trione, 2-bromo-12'-hydroxy-2'-(1-methylethyl)-5'-(2-methylpropyl)-, (5'alpha)-), elymociavin, ergocristin (ergotaman-3',6',18-trione, 12'-hydroxy-2'-(1-methylethyl)-5'-(phenylmethyl)-, (5'-alpha)-), ergocristinin, ergocornin (ergotaman-3',6',18-trione, 12'-hydroxy-2',5'-bis(1-methylethyl)-, (5'-alpha)-), ergocorninin, ergocryptin (ergotaman-3',6',18-trione, 12'-hydroxy-2'-(1-methylethyl)-5'-(2-methylpropyl)-, (5'alpha)-(9Cl)), ergocryptinin, ergometrin, ergonovin (ergobasin, INN: ergometrin, (8beta(S))-9,10-didehydro-N-(2-hydroxy-1-methylethyl)-6-methyl-ergoline-8-carboxamid), ergosin, ergosinin, ergotmetrinin, ergotamin (ergotaman-3',6',18-trione, 12'-hydroxy-2'-methyl-5'-(phenylmethyl)-, (5'-alpha)-(9Cl)), ergotaminin, ergovalin (ergotaman-3',6',18-trione, 12'-hydroxy-2'-methyl-5'-(1-methylethyl)-, (5'alpha)-), lergotril, lisurid (CAS-No.: 18016-80-3, 3-(9,10-didehydro-6-methylergolin-8alpha-yl)-1,1-diethyl carbamide), lysergol, lysergic acid (D-lysergic acid), lysergic acid amide (LSA, D-lysergic acid amide), lysergic acid diethylamide (LSD, D-lysergic acid diethylamide, INN: lysergamide, (8beta)-9,10-didehydro-N,N-diethyl-6-methyl-ergoline-8-carboxamide), isolysergic acid (D-isolysergic acid), isolysergic acid amide (D-isolysergic acid amide), isolysergic acid diethylamide (D-isolysergic acid diethylamide), mesulergin, metergolin, methergin (INN: methylergometrin, (8beta(S))-9,10-didehydro-N-(1-(hydroxymethyl)propyl)-6-methyl-ergo line-8-carboxamide), methylergometrin, methysergid (INN: methysergid, (8beta)-9,10-didehydro-N-(1-(hydroxymethyl)propyl)-1,6-dimethyl-ergoline-8-carboxamide), pergolid ((8beta)-8-((methylthio)methyl)-6-propyl-ergolin), protergurid and tergurid, celecoxip, thalidomid, Fasudil®, ciclosporin, smc proliferation inhibitor-2w, epothilone A and B, mitoxantrone, azathioprine, mycophenolatmofetil, c-myc-antisense, b-myc-antisense, betulinic acid, camptothecin, PI-88 (sulfated oligosaccharide), melanocyte-stimulating hormone (α-MSH), activated protein C, IL1-β-inhibitor, thymosine α-1, fumaric acid and its esters, calcipotriol, tacalcitol, lapachol, β-lapachone, podophyllotoxin, betulin, podophyllic acid 2-ethylhydrazide, molgramostim (rhuGM-CSF), peginterferon α-2b, lanograstim (r-HuG-CSF), filgrastim, macrogol, dacarbazin, basiliximab, daclizumab, selectin (cytokine antagonist), CETP inhibitor, cadherines, cytokinin inhibitors, COX-2 inhibitor, NFkB, angiopeptin, ciprofloxacin, camptothecin, fluoroblastin, monoclonal antibodies, which inhibit the muscle cell proliferation, bFGF antagonists, probucol, prostaglandins, 1,11-dimethoxycanthin-6-on, 1-hydroxy-11-methoxycanthin-6-on, scopolectin, colchicine, NO donors such as pentaerythritol tetranitrate and syndnoeimines, S-nitrosoderivatives, tamoxifen, staurosporine, β-estradiol, α-estradiol, estriol, estrone, ethinylestradiol, fosfestrol, medroxyprogesterone, estradiol cypionates, estradiol benzoates, tranilast, kamebakaurin and other terpenoids which are applied in the therapy of cancer, verapamil, tyrosine kinase inhibitors (tyrphostines), cyclosporine A and B, paclitaxel and its derivatives such as 6-α-hydroxy-paclitaxel, baccatin, taxotere, synthetically produced macrocyclic oligomers of carbon suboxide (MCS) and its derivatives as well as those obtained from native sources, mofebutazone, acemetacin, diclofenac, lonazolac, dapsone, o-carbamoylphenoxyacetic acid, lidocaine, ketoprofen, mefenamic acid, piroxicam, meloxicam, chloroquine phosphate, penicillamine, tumstatin, avastin, D-24851, SC-58125, hydroxychloroquine, auranofin, sodium aurothiomalate, oxaceprol, celecoxib, β-sitosterin, ademetionine, myrtecaine, polidocanol, nonivamide, levomenthol, benzocaine, aescin, ellipticine, D-24851 (Calbiochem), colcemid, cytochalasin A-E, indanocine, nocodazole, S 100 protein, bacitracin, vitronectin receptor antagonists, azelastine, guanidyl cyclase stimulator, tissue inhibitor of metal proteinase-1 and -2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1, active agents from the group of antibiotics such as cefadroxil, cefazolin, cefaclor, cefotixin, tobramycin, gentamycin, penicillins such as dicloxacillin, oxacillin, sulfonamides, metronidazol, antithrombotics such as argatroban, aspirin, abciximab, synthetic antithrombin, bivalirudin, coumadin, enoxaparin, desulfated and N-reacetylated heparin, tissue plasminogen activator, GpIIb/IIIa platelet membrane receptor, factor $X_a$ inhibitor antibodies, interleukin inhibitors, heparin, hirudin, r-hirudin, PPACK, protamine, sodium salt of 2-methylthiazolidin-2,4-dicarboxylic acid, prourokinase, streptokinase, warfarin, urokinase, vasodilators such as dipyramidole, trapidil, nitroprussides, PDGF antagonists such as triazolopyrimidine and seramin, ACE inhibitors such as captopril, cilazapril, lisinopril, enalapril, losartan, thioprotease inhibitors, prostacyclin, vapiprost, interferon α, β and γ, histamine antagonists, serotonin blockers, apoptosis inhibitors, apoptosis regulators such as p65, NF-kB or Bcl-xL antisense oligonucleotides, halofuginone, nifedipine, tocopherol, vitamin B1, B2, B6 and B12, folic acid, tranilast, molsidomine, tea polyphenols, epicatechin gallate, epigallocatechin gallate, Boswellic acids and their derivatives, leflunomide, anakinra, etanercept, sulfasalazine, etoposide, dicloxacillin, tetracycline, triamcinolone, mutamycin, procainamid, D24851, SC-58125, retinoic acid, quinidine, disopyramide, flecamide, propafenone, sotalol, amidorone, natural and synthetically prepared steroids such as bryophyllin A, inotodiol, maquirosid A, ghalakinosid, mansonin, streblosid, hydrocortisone, betamethasone, dexamethasone, non-steroidal substances (NSAIDS) such as fenoprofen, ibuprofen, indomethacin, naproxen, phenylbutazone and other antiviral agents such as acyclovir, ganciclovir and zidovudine, antimycotics such as clotrimazole, flucytosine, griseofulvin, ketoconazole, miconazole, nystatin, terbinafine, antiprotozoal agents such as chloroquine, mefloquine, quinine, furthermore natural terpenoids such as hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceanol A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-α-senecioyloxychaparrin, taxamairin A and B, regenilol, triptolide, furthermore cymarin, apocymarin, aristolochic acid, anopterin, hydroxyanopterin, anemonin, protoanemonin, berberine, cheliburin chloride, cictoxin, sinococuline, bombrestatin A and B, cudraisoflavone A, curcumin, dihydronitidine, nitidine chloride, 12-beta-hydroxypregnadiene-3,20-dione, bilobol, ginkgol, ginkgolic acid, helenalin, indicine, indicine-N-oxide, lasiocarpine, inotodiol, glycoside 1a, podophyllotoxin, justicidin A and B, larreatin, malloterin, mallotochromanol, isobutyrylmallotochromanol, maquiroside A, marchantin A, maytansine, lycoridicin, margetine, pancratistatin, liriodenine, oxoushinsunine, aristolactam-All, bisparthenolidine, periplocoside A, ghalakinoside, ursolic acid, deoxypsorospermin, psychorubin, ricin A, sanguinarine, manwu wheat acid, methylsorbifolin, sphatheliachromen, stizophyllin, mansonine, strebloside, akagerine, dihydrousambarensine, hydroxyusambarine, strychnopentamine, strychnophylline, usambarine, usambarensine, berberine, liriodenine, oxoushinsunine, daphnoretin, lariciresinol, methoxylariciresinol, syringaresinol, umbelliferon, afromoson, acetylvismione B, desacetylvismione A, vismione A and B, and sulfur-containing amino acids such as cysteine as well as salts, hydrates, solvates, enantiomers, racemates, enantiomeric mixtures, diastereomeric mixtures, metabolites, prodrugs and mixtures of the above mentioned active agents.

Basically any active agent as well as combination of active agents can be used, wherein, however, paclitaxel and paclitaxel derivatives, taxanes, docetaxel as well as rapamycin and rapamycin derivatives as e.g. biolimus A9, pimecrolimus, everolimus, zotarolimus, tacrolimus, fasudil and epothilones are preferred and particularly preferred are paclitaxel and rapamycin.

Paclitaxel is known under the brand name Taxol® and the chemical name [2aR-[2a,4,4a,6,9 (R*,S*),11,12,12a,12b]]-(benzoylamino)-hydroxybenzolpropionic acid-6,12b-bis-(acetyloxy)-12-(benzoyloxy)-2a-3,4,4a,5,6,9,10,11,12,12a, 12b-dodecahydro-4,11-dihydroxy-4-a,8,13,13-tetramethyl-5-oxo-7,11-methano-1H-cyclodeca[3,4]benz[1,2-b]oxet-9-yl-ester.

Rapamycin is also known as Rapamun or under the International Nonproprietary Name (INN) sirolimus as well as under the IUPAC name [3S-[3R*[E(1S*,3S*,4S*)],4S*,5R*, 8S*,9E,12R*,14R*,15S*,16R*,18S*,19S*,26aR*]]-5,6,8, 11,12,13,14,15,16,17,18,19,24,25,26,26a-hexadeca-hydro-5,19-dihydroxy-3-[2-(4-hydroxy-3-methoxycyclohexyl)-1-methylethenyl]-14,16-dimethoxy-4,10,12,18-tetramethyl-8-(2-propenyl)-15,19-epoxy-3H-pyrido[2,1-c][1,4]-oxaazacyclo-tricosene-1,7,20,21(4H,23H)-tetrone-monohydrate.

Prodrugs refer to a preliminary stage of a pharmacologically active compound which under physiological conditions is changed into the active compound.

The active agents or combinations of active agents reach their target site preferably by means of a transport agent or as their own transport mediator in a sufficient concentration during the limited exposure time of the short-term implant.

As already mentioned, a major problem of the embodiments of the state-of-the-art consists in transferring with a dilation time of maximally 1 minute and possibly several repetitions of the dilation after a certain pause and preferably maximally 45 seconds and particularly preferably for maximally 30 seconds a sufficient substance amount onto the stenotic or restenotic or thrombotic vessel section so that a restenosis or re-occlusion of the vessel section is impeded also in a dilation without stent placement. Since with higher exposure times, i.e. dilation times, the risk for a heart attack is increased there is only a short time left for the transfer of the substance(s) onto respectively into the vascular wall. Furthermore, in "biological stenting" without a stent also a repeated expansion and recompression of the catheter balloon for ensuring temporarily at least a slight bloodstream is critical since the active agent is released in its major part already during the first expansion of the catheter balloon and further dilations cannot contribute anymore to a considerable substance transfer onto the vascular wall.

Thus special coatings are needed which transfer in a relatively short time a relative high amount of substance in a controlled manner onto and/or into the vascular wall.

Transport Mediators

In order to increase the substance transfer preferably so-called transport mediators or transport accelerators are used which, however, can be the active agent itself.

Of special interest are embodiments according to the invention containing low molecular chemical compounds as transport mediators accelerating respectively facilitating the uptake of the active agent into the vascular wall so that the present active agent or combination of active agents can be transported during the short exposure time in a controlled manner and in the scheduled dosage through the cell membrane into the cytosol.

Herein the transport accelerator may also function as a carrier. Several options are possible: the linkage between the active agent and the carrier already exists and is cleaved after entering the cell, or it is formed on the outside of the membrane for the time of the passage through the membrane and cleaved again thereafter, or carrier and active agent form one entity subsisting also in the cytosol, but not negatively biasing the efficacy of the active agent.

Such properties are displayed by substances interacting directly with the lipid double layer of the cell membrane, with receptors on the cell membrane or entering the cytosol via membrane transport proteins acting as carriers or channels (ion pumps) where they change the membrane potential and thus the cellular membrane permeability. Thus the uptake of an active agent into cells is facilitated respectively accelerated.

Primarily, the ability of substances to diffuse through a membrane into the cell corresponds directly to the substance size. Smaller molecules pass easier than larger ones. Molecules undergoing a lesser number of hydrogen bridge bonds correspondingly also diffuse faster than molecules eager to form hydrogen bridges. Also the polarity of the molecule is important. Taking these facts into account a number of synthetic, semi-synthetic and native substances can be used to change the permeability of a cell membrane in such a way that the entering of an active agent occurs optimally.

Among such useful compounds are for example vasodilators encompassing endogenous substances as kinins, for example bradykinin, kallidin, histamine and NO synthase releasing from L-arginine the vasodilatory active NO. Substances of herbal origin as the verifiably vasodilatory Gingko biloba extract, DMSO, xanthones, flavonoids, terpenoids, herbal and animal colorants, food dyes. NO donors as e.g. pentaerythrityl tetranitrate (PETN), contrast media and contrast medium analogues belong likewise to this category.

Thus there are two possibilities which can also be combined for supporting the transport of one or more active agents into cells:
1. The transport accelerator respectively mediator causes an immediate substance transfer into cells limited by the exposure time with the medical device.
2. After removing the medical device the transport accelerator respectively mediator adheres to the cell wall in combination with the active agent and possibly an adhesion-supporting carrier (respectively reservoir). Thus the diffusion of the active agent into the cell is retarded and dose-controlled.

Transport mediators, the active agent respectively the combination of active agents as well as a possible matrix may be applied on the medical device adhesively and/or covalently, partially or entirely covering:
1. The transport mediator and the active agent adhere adhesively and/or covalently on the medical device or on an adhesively or covalently applied matrix.
2. The transport mediator and the active agent are covalently linked and adhere adhesively on the medical device or on a matrix adhesively or covalently applied on the medical device.
3. The transport mediator and the active agent are covalently linked and adhere covalently on the medical device or on a matrix adhesively or covalently applied on the medical device.

In many cases the effect of the mentioned substances is not limited to the transport properties, but they additionally display a positive beneficial effect. For example NO produced by the cell itself is not only vasodilatory but also has antiproliferative properties. Thus all NO donors are antiproliferatives and vasodilators at the same time.

Combinations with other antiproliferative, cytotoxic and cytostatic, anti-inflammatory and also antithrombotic substances can be used herein for potentiation respectively complementation of the adjuvant effectiveness.

Similar to nitric oxide is carbon monoxide. In one embodiment of the present invention CO or NO or a mixture of CO and NO is released from the inside of the catheter balloon through a plurality of micro- or nano-pores and supports during dilation the detachment of the coating on the catheter balloon from the balloon surface as well as the uptake of the active agent located in the coating of the balloon surface into the vascular wall as a vasodilator. On the balloon surface there is preferably a polymeric coating containing one or more active agents which counteract respectively impede a re-occlusion or restenosis of the vessel. Suitable polymers for such a coating are described further below.

Another embodiment according to the invention uses coatings on the catheter balloons, and if available, optionally also on the uncrimped stent, that contain CO or NO or CO and NO in a complexed or chemically bound form. In all embodiments NO as well as a combination of CO and NO, independent of the nature how both substances are present.

CO is provided preferably in a complexed form, for example as a complex with haemoglobin, haemoglobin derivatives, haemoglobin analogues or with metals and metal ions in form of carbonyl metallates. For example, NO can be provided as a complex with haemoglobin, haemoglobin derivatives, haemoglobin analogues, chemically bond as a nitrosamine or chemically bond in form of the functional group $-N_2O_2^-$, in complex compounds with metals and metal ions as e.g. $[Fe(H_2O)_5NO]^{2+}$, or in form of other nitroxides.

Haemoglobin derivatives are molecules generated from haemoglobin through chemical modification. Haemoglobin analogues are substances displaying haemoglobin characteristics in respect of oxygen complexation (namely to act as an oxygen transport system) or of carbon monoxide as well as the physiological compatibility of natural haemoglobin. Among these substances tagged as haemoglobin analogues are for example cells as molecular erythrocytes that can be isolated from certain earthworms and serve as an oxygen transport system as well as synthetic oxygen carriers as perfluorocarbon emulsions.

A particularly preferred embodiment comprises the use of haemoglobin colloids which can be obtained for example by isolating haemoglobin from pigs and crosslinking it with dialdehydes as glyoxal, glycolaldehyde, glutaric dialdehyde. Examples for such haemoglobin derivatives and their synthesis are described in WO 02/00229 A and WO 02/00230 A. Herein it is particularly referred to embodiments 1 and 2 as well as the pages 14-16 of WO 02/00230 A and the embodiments 1-13 as well as the pages 7-16 of the description. Such haemoglobin derivatives can then be enriched with CO and/or NO and be placed on the surface of the catheter balloon respectively also of the stent. The application can be carried out on or together with a biostable or biodegradable polymer.

Moreover, the gases CO, NO, $N_2O$, $N_2O_2$ or $N_2O_3$ can be also solved in oils or be absorbed in liposomal formulations or be administered in dispersions or emulsions. Examples for such oils suitable for serving as coating materials and for absorbing NO and/or CO are described in detail further down.

These substances containing CO and/or NO in a complexed, chemically bond and/or embedded form can further be integrated in or applied on a biostable or biodegradable polymeric matrix which is located on the surface of the catheter balloon respectively of the stent (if available), or with which the catheter balloon respectively the stent is coated, or with which the microstructures or the folds are filled. As already explained, the term "coating of the surface of the catheter balloon" shall comprise also the filling of possible folds micro- or nano-structures, micro- or nano-needles or other indentations or cavities on the surface of the balloon or in the balloon material.

Other embodiments according to the invention use enzymes synthesizing CO or NO or activators for these enzymes, nucleotide sequences as for example DNA and RNA encoding for these enzymes and enhancing the expression of these enzymes when brought into cells and/or inhibitors for enzymes breaking down CO or NO.

Another preferred embodiment is a catheter balloon with or without a stent on the surface of which a NO-synthesizing enzyme is located. This enzyme can be embedded optionally in a polymeric matrix of biostable or biodegradable, synthetic, semi-synthetic or biologic polymers, and/or applied on such a polymeric matrix and/or coated with such a polymeric layer.

Preferably, this NO-synthesizing enzyme is a NO synthase. NO synthases (NOS) as for example endothelial NO synthase (NOS III) are able to produce nitric oxide, for example from the amino acid L-arginine.

Thus in a further preferred embodiment a NO synthase together with a suitable amino acid, particularly arginine, are provided on the implant.

It is also preferred to provide corresponding activators of NO synthesizing enzymes with the implant. Activators may be for example statins or glutamate. A particularly preferred embodiment contains at least one NO-synthesizing enzyme, particularly a NO synthase, on the implant. This at least one NO-synthesizing enzyme is beneficially embedded in a polymeric matrix and particularly immobilized on a polymeric matrix and particularly covalently immobilized thereon thus enhancing the enzyme stability and making the enzyme degradation more difficult. At the same time also a substrate is provided, for example L-arginine, which can be located under, in as well as on the polymeric matrix. Furthermore, it is advantageous to provide also an activator for the enzyme as for example statins or glutamate so that on the implant surface a complete machinery for nitric oxide production is located. Statins can be for example: Atorvastatin, lovastatin, simvastatin, rosuvastatin, pravastatin, fluvastatin and cerivastatin.

Separately or concomitantly substances can be released from the surface of the temporary short-term implant which inhibit the degradation or inactivation of NO. Among these substances are especially those which foster the degradation or the inactivation of superoxide anions ($O_2^-$) or inhibit the formation of superoxide anions, as for example the enzymes superoxide dismutase and glutathione peroxidase as well as inhibitors of NADPH oxidase and activators of superoxide dismutase or glutathione peroxidase.

Preferably, superoxide dismutase (SOD), glutathione peroxidase (GSH-Px), catalase, activators of superoxide dismutase, activators of glutathione peroxidase and/or inhibitors of NADPH oxidase in combination with NO, a NO-containing compound or a NO-synthesizing enzyme are used. Particularly preferred is an implant with a coating comprising NO synthase, arginine, a statin, glutamate and an activator of superoxide dismutase or an activator or glutathione peroxidase.

Another preferred embodiment of the present invention comprises temporary short-term implants, i.e. catheter balloons with or without a crimped stent which can influence via a genetic approach the NO respectively CO homeostasis of cells, especially of endothelial and smooth muscle cells (SMC). Therefore nucleotide sequences respectively genes are transported into cells, preferably endothelial and smooth muscle cells, coating the internal vessel wall, that encode for a NI-synthesizing enzyme, for example a NO synthase as NOS III or a CO-synthesizing enzyme, for example a heme oxygenase, CO synthase (UPG III S: uroporphyrinogene III synthase), 2,4-dioxygenases as e.g. 1H-3-hydroxy-4-oxo-quinaldine-2,4-dioxygenase (QDO and MeQDO) or Aci-reducton oxidase.

This gene transfer provides the advantage that CO and/or NO are locally produced in situ where the vessel defect occurred or is feared to occur. The gene material in form of a DNA or RNA, preferably DNA, can be transported into the cells via viruses (for example adenoviruses or bacculoviruses) or as liposomal complexes. For example a gene encoding for NOS III or for heme oxigenase (HO) can be provided embedded in a pAH 9 vector and as a lipid vesicle being able to fuse with the lipophilic cell membrane and thus be transported into the cell. Inside the cell endosomes transport lipoplexes to the nucleus. The inducible DNA is not integrated into the chromosomal DNA of the cell but remains active in the nucleus as an independent so-called episomal plasmid DNA. A segment of the plasmid DNA arranged as a promoter starts the synthesis of the enzyme, e.g. of NOS III or of heme oxigenase which then would produce NO respectively CO.

This gene material is provided on the surface of the temporary short-term implant and contacts on dilation of the catheter balloon the respective cells that, absorb the gene material and start the enzyme production. Thus it is furthermore advantageous when also the respective substrate of the produced enzyme is located on the surface of the catheter balloon respectively of the stent. Substrates can be for example biliverdin or L-arginine. Moreover, there can be further substances on the surface of the catheter balloon or the stent which inhibit the degradation of NO respectively CO. Among these substances are the aforementioned activators of superoxide dismutase, activators of glutathione peroxidase, inhibitors of NADPH oxidase or superoxide dismutase and/or glutathione peroxidase themselves.

Furthermore, the formation respectively the activation of the formation and/or release of CO is preferred which can be controlled also by the temporary short-term implant according to the invention. As already explained, the catheter balloon may contain elementary CO as well as NO in its core, or CO in a complexed or chemically bond form be present on its surface, without or with a coating, especially a biodegradable or biostable polymeric coating.

CO can be provided as a gas, a liquid or as a solid. The liquid or the solid are preferred. Particularly, CO is used in a form able to release CO continually. Such forms for continual CO release comprise especially one or more polymeric matrix(ces), liposomal formulation(s), CO precursor, microformulation(s), nano-formulation(s), carbon coating(s) or CO complex compound(s).

A polymeric matrix is conceived as the embedding respectively storing of CO in a biopolymer as for example heparin, chitosan or derivatives thereof, in a synthetic or semi-synthetic polymer as e.g. polysulfones, polyacrylates and the like.

Liposomal formulations mean micelle-building systems, wherein CO is stored in micelles and is applied in this form onto a medical implant.

CO precursors designate chemical compounds able to release, respectively to build, CO. CO precursors are chemical compounds disintegrating to CO or releasing CO during their disintegration or being substrates for enzymes which produce CO during the conversion of these substrates. A particularly preferred CO source are CO complex compounds, for example out of ruthenium and iron, able to release CO.

Micro- and nano-formulations with CO refer to micro- and nanoparticles containing CO.

According to the invention a medical short-term implant (catheter balloon with or without a stent) is coated with at least one of the aforementioned CO containing formulations.

In this coating method according to the invention a catheter balloon with or without a stent is provided and its surface is coated at least partially with CO and/or one of the aforementioned CO containing formulations. For this coating CO can be used as a solid wherein corresponding cooling methods for solidifying the gas can be employed. The use of CO as a liquid or a gas, however, is possible too. For example, CO as a liquid or a gas is incorporated herein in micro- or nano-capsules, or embedded in liposomal formulations. These micro- or nano-capsules can release CO after dissolution. The liposomal formulations are degraded gradually, releasing CO in the meantime. Furthermore, powder forms are preferred in which CO is incorporated.

Furthermore it is preferred that the temporary short-term implant according to the invention concomitantly releases NO and CO, or enhances the release, respectively the production, of NO and CO. Furthermore it is preferred that besides NO and/or CO or instead of NO and CO compounds, especially neurotransmitters activating respectively stimulating guanylyl cyclase (sGC), are released from the catheter balloon with or without a stent. Fe ions, Zn ions and Ca ions are important for guanylyl cyclase activity and should be provided likewise through the temporary short-term implant. Thus medical temporary short-term implant are a preferred embodiment if they release at least one guanylyl cyclase activator, as for example iron ions, zinc ions, calcium ions, CO and/or NO.

As an example a catheter balloon should be mentioned that includes on its surface heme oxigenase (HO) or another CO-building enzyme. HO2 indicates the non-inducible and HO1 the inducible form of heme oxigenase.

Furthermore it is preferred that the heme oxigenase, particularly HO1, is provided together with a suitable substrate as for example heme. Instead of or together with a substrate also an activator of heme oxigenase can be present in, under and/or on the coating. Preferred substrates are heme, biliverdin or bilirubin, and as activators for example phorbol ester or rapamycin can be named. Particularly preferred are such embodiments with NO and/or CO in combination with paclitaxel or rapamycin.

All of the aforementioned substances are preferably included in a polymeric matrix of biodegradable or biostable synthetic, semi-synthetic or biological polymers, coated with such a matrix and/or applied on such a matrix. Suitable polymers for such a matrix are mentioned further below.

The temporary short-term implants according to the invention include in the catheter balloon or preferably on the surface of the catheter balloon and possibly of the stent with or without a polymeric matrix and at least one pharmacologically active agent especially an anti-inflammatory, cytostatic, cytotoxic, antiproliferative, anti-microtubuli, anti-angiogenic, anti-restenotic, antifungicide, antineoplastic, antimigratory, athrombogenic, antithrombogenic agent, at least one of the following substances:

a) CO, NO, mixture of CO and NO
b) NO synthase, a NO-synthesizing enzyme
c) L-arginine
d) statin(s)
e) glutamate
f) activators of NO synthase, activators of NO-synthesizing enzymes
g) superoxide dismutase and/or activators of superoxide dismutase
h) glutathione peroxidase and/or activators of glutathione peroxidase
i) inhibitors of NADPH oxidase
j) DNA or RNA encoding for NO synthase
k) heme oxigenase, a CO-synthesizing enzyme
l) DNA or RNA encoding for heme oxigenase
m) rapamycin
n) paclitaxel
o) heme
p) biliverdin
q) phorbol ester Preferred are the following combinations:
a+g, a+h, a+l, a+d, a+e, a+f, a+m, a+q, a+n, b+d, b+e, b+d+e, b+f, b+f+g, b+f+h, b+f+b+c+d, b+c+e, d+j, e+j, k+m, k+n, k+q, k+b, l+m, l+n, l+q, k+o, l+o The medical temporary short-term implants according to the invention, especially stents, are used for preventing or reducing restenosis, particularly in-stent restenosis.

The temporary short-term implants are particularly suitable for the treatment and prophylaxis of vascular diseases originating from a decrease in wall shear stress, respectively a concomitant stretch-induced increase in leucocyte adhesion and emigration. Such processes occur often at vessel bifurcations. The vessel implants according to the invention can cause an increase in wall shear stress and a strengthening or activation of smooth muscle cells (SMC), respectively of the vascular endothelium, thus reducing or lowering to physiological measures thrombocyte adhesion and diapedesis of leucocytes present in the bloodstream. This prevents inflammatory processes and avoids for example chronic inflammatory bowel diseases, as most notably Crohn's disease as well as atherosclerosis, stenosis or restenosis.

As previously mentioned these are mostly low molecular compounds facilitating transmembranous transport directly or indirectly. For example, dimethyl sulfoxide (DMSO) is known for a long time as a carrier substance for topical medicaments. Its contribution in ointments, tinctures, gels etc lies in its property as a transport mediator facilitating the absorption of active agents in the skin, or generally in cell membranes. Moreover, in low concentrations DMSO shows analgesic and antiphlogistic actions, which is an additional positive effect.

Endothelial cells produce nitric oxide (NO) from L-arginine through activation of NO synthase as an endogenously released signaling molecule having vasodilatory effects on the vascular wall. Therefore compounds releasing rapidly and specifically NO or increasing its bioavailability can be used equally well as transport mediators. Since NO is not only vasodilatory but shows also antiproliferative and antioxidative actions it has additional inhibitory effects particularly in restenosis. Here, pentaerythrytiltetranitrate (PETN) containing even four nitro groups, nitroprusside, nitroglycerine, hydralazines, isosorbide dinitrate (ISDN), 4-[5-amino-3-(4-pyridyl)-1-pyrazolyl]-1-methyl piperidines, benzodifuroxans, benzotrifuroxans, S-nitroso-N-acetyl-penicillamine (SNAP), aspirin-NO donor ester, 3-morpholinosydnon-imines (SIN-1), 8-bromo-cGMP (8-BrcGMP), 8-(4-chlorophenylthio)-cGMP (pCPT-cGMP), ☐,☐-methylene ATP, S-nitrosoglutathione (GSNO), monoethanolamine-nicotinates, phenoxyalkylamines, their derivatives, metabolites and analogues can be named. Other suitable compounds are for example Sodium (Z)-1-(N,N-diethylamino)diazene-1-ium-1,2-diolate (DEA-NO):

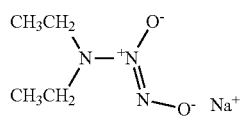

Sodium 1-(N,N-diethylamino)diazene-1-ium-1,2-diolate:

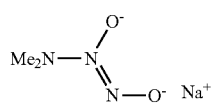

(Z)-1-{N-methyl-N-[6-(N-methylammoniohexyl)amino]}diazene-1-ium-1,2-diolate (NOC-9):

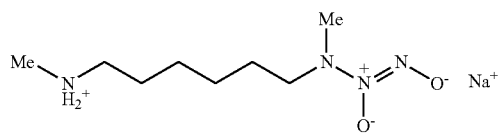

Disodium 1-[(2-carboxylato)pyrrolidine-1-yl]diazene-1-ium-1,2-diolate:

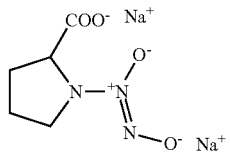

$O^2$-vinyl 1-(pyrrolidone-1-yl)diazene-1-ium-1,2-diolate:

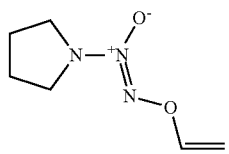

Sodium-1-[4-(5-dimethylamino-1-naphthalenesulfonyl)piperazine-1-yl]diazene-1-ium-1,2-diolate:

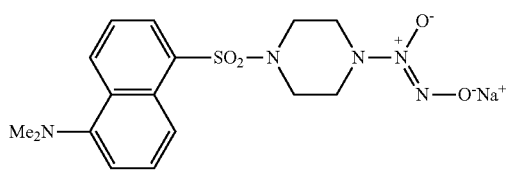

$O^2$-(sodium-1-(isopropylamino)diazene-1-ium-1,2-diolate:

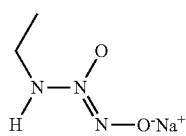

Sodium-1-[4-(pyrimidine-2-yl)piperazine-1-yl]diazene-1-ium-1,2-diolate:

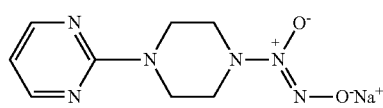

Sodium-1-[4-(phenylpiperazine-1-yl]diazene-1-ium-1,2-diolate:

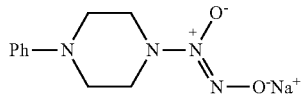

Sodium-1-[4-(ethoxycarbonylpiperazine-1-yl]diazene-1-ium-1,2-diolate:

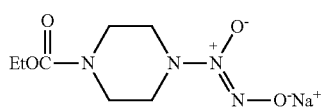

(Z)-1-{N-methyl-N-[6-(N-methylammoniohexyl)amino]}diazene-1-ium-1,2-diolate:

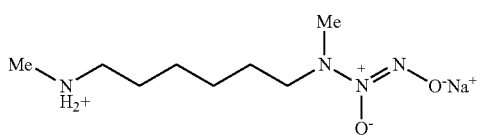

Sodium-1-(pyrrolidine-1-yl]diazene-1-ium-1,2-diolate:

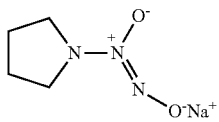

1-hydroxy-2-oxo-3-(3-aminopropyl)-3-isopropyl-1-triazene (NOC-5):

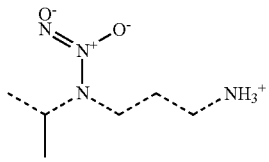

1-hydroxy-2-oxo-3-(N-methyl-3-aminopropyl)-3-methyl-1-triazene (NOC-7):

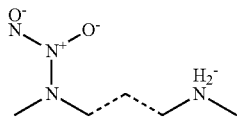

and also as an example for the covalent binding of NO-releasing compounds on biocompatible polymers, or representatively for the group of polysacchsarides a diazeniumdiolate heparin:

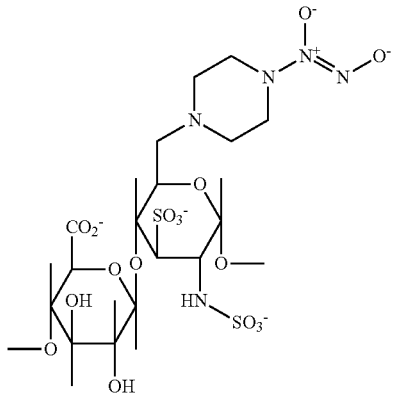

Particularly the NO-releasing compounds as PETN having even four nitro groups to be released are excellently suitable for the covalent binding to for example an active agent, matrix or other low molecular compounds increasing the rapid availability of NO or, if necessary, also lowering it. For example the aforementioned diazeniumdiolate heparin has under physiological conditions (pH 7.4, 37° C.) a half-life time of 8.4 min.

For example, molecular designers currently couple NO to non-steroidal antirheumatics in order to improve their tolerance and effectiveness. At the University of Jena also solid NO compounds are used. Some of them have very low half-life times. After injection they release NO during two seconds. Such active agents may be useful in spasmolysis of cerebral vasospasms, in coating stents and in an ideal manner for short-term implants such as balloon catheters.

Apart of the aforementioned substances suitable substances for transport mediation are: Carbocromen-HCl, cinnarizine, dihydralazine sulphate, dipyridamole, etofylline, isosorbide dinitrate (Lactosever), nicotinic acid, propanolol, nifedipine, pentoxyfylline, prenylamine lactate, tolazoline-HCl, acetylcholine, phosphatidylcholine, insulin glargine, gentiacaulein and gentiakochianin, thieno[3,2-c]pyridine and derivatives, benzothiadiazines as e.g. hydrochlorothiazide, euxanthone, garcinone E, gentisin, euxanthinic acid, isogentisin, gentisein, mangiferin and homomangiferin, 2-pyrrolidone, citrates as acetyltributyl and acetyltriethyl citrate, tributyl and triethyl citrate, benzoic acid benzylester, phtalates as dibutyl and triethyl phtalate, fatty acid esters as isopropyl myristate and palmitate, triacetine, anthocyans as pelargonidine, cyanidine, delphidine, paeonidine, petunidine, malvidine, catechines as well as their derivatives and metabolites.

The combination of a transmembranous transport mediator and active agent may be realized in different embodiments:
1. transport mediator and active agent are identical
2. transport mediator and active agent are not identical, but support the other in its action
3. the transport mediator has no influence on the effect of the added active agent and serves exclusively as a transport vehicle Particularly citrates and citrate esters are excellent components for a coating, respectively the dissolution of a coating. It has been shown that citrates and citrate esters favour the adhesion of the coating released to the tissue and foster the uptake of one or more active agents into the tissue and the cells.

Citrates have the following structure:

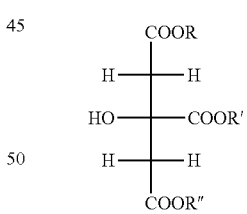

wherein
R, R' and R" are independently from one another hydrogen or an alkyl, arylalkyl or cycloalkyl group which can be linear or branched, saturated or unsaturated, substituted with at least one functional moiety or unsubstituted.

As functional groups the following moieties are eligible:
—H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —SH, —SCH$_3$, —SC$_2$H$_5$, —NO$_2$, —F, —Cl, —Br, —I, —COCH$_3$, —COC$_2$H$_5$, —COC$_3$H$_7$, —CO-cyclo-C$_3$H$_5$, —COCH(CH$_3$)$_2$, —COOH, —COOCH$_3$, —COOC$_2$H$_5$, —COOC$_3$H$_7$, —COO-cyclo-C$_3$H$_5$, —COOCH(CH$_3$)$_2$, —OOC—CH$_3$, —OOC—C$_2$H$_5$, —OOC—C$_3$H$_7$, —OOC-cyclo-C$_3$H$_5$, —OOC—CH(CH$_3$)$_2$, —CONH$_2$, —CONHCH₃, —CONHC₂H₅, —CONHC₃H₇, —CONH-cyclo-C₃H₅, —CONH[CH(CH₃)₂], —CON(CH₃)₂, —CON(C₂H₅)₂, —CON(C₃H₇)₂, —CON(cyclo-C₃H₅)₂, —CON[CH(CH₃)₂]₂, —NHCOCH₃, —NHCOC₂H₅, —NHCOC₃H₇, —NHCO-cyclo-C₃H₅, —NHCO—CH(CH₃)₂, —NHCO—OCH₃, —NHCO—OC₂H₅, —NHCO—OC₃H₇, —NHCO—O-cyclo-C₃H₅, —NHCO—OCH(CH₃)₂, —NHCO—OC(CH₃)₃, —NH₂, —NHCH₃, —NHC₂H₅, —NHC₃H₇, —NH-cyclo-C₃H₅, —NHCH(CH₃)₂, —NHC(CH₃)₃, —N(CH₃)₂, —N(C₂H₅)₂, —N(C₃H₇)₂, —N(cyclo-C₃H₅)₂, —N[CH(CH₃)₂]₂, —SO₂CH₃, —SO₂C₂H₅, —SO₃H, —SO₃CH₃, —SO₃C₂H₅, —OCF₃, —OC₂F₅, —NH—CO—NH₂, —NH—C(=NH)—NH₂, —O—CO—NH₂, —O—CO—NHCH₃, —O—CO—N(CH₃)₂, —O—CO—N(C₂H₅)₂, —CH₂F, —CHF₂, —CF₃, —CH₂Cl, —CH₂Br, —CH₂—CH₂F, —CH₂—CF₃, —CH₂—CH₂Cl, —CH₂—CH₂Br, —CH₃, —C₂H₅, —C₃H₇, —CH(CH₃)₂, —C(CH₃)₃, —C₄H₉, —CH₂—CH(CH₃)₂, —CH(CH₃)—C₂H₅, —C₅H₁₁, —C₇H₅, —C₈H₁₇, -cyclo-C₃H₅, -cyclo-C₄H₇, -cyclo-C₅H₉, -cyclo-C₆H₁₁, —Ph, —CH₂—Ph, —CH=CH₂, —CH₂—CH=CH₂, —C(CH₃)=CH₂, —CH=CH—CH₃, —C₂H₄—CH=CH₂, —CH=C(CH₃)₂, —C≡CH, —C≡C—CH₃, —CH₂—C≡CH.

Preferred are the aforementioned alkyl groups, substituted alkyl groups as well as diesters and especially triesters of citric acid.

Contrast Media

Another group of substances preferred for use are contrast media and/or contrast media analogues. Contrast media and contrast media analogues may partially also serve as transport mediators, having the property that they are not polymeric compounds. Moreover, they are often have a clinical authorization, are mostly physiologically not critical and can be used in such cases when polymeric carrier systems and substances should be avoided.

Contrast media and/or contrast media analogues contain additionally barium, iodine, manganese, iron, lanthanum, cerium, praseodymium, neodymium, samarium, europium, gadolinium, terbium, dysprosium, holmium, erbium, thulium, ytterbium and/or lutetium preferably as ions in the bound and/or complex form.

In principle, contrast media are to be distinguished for different imaging methods. On the one hand, there are contrast media which are used in x-ray examinations (x-ray contrast media) or contrast media which are used in magnetic resonance tomography examinations (MR contrast media).

In the case of x-ray contrast media substances are concerned which result in an increased absorption of penetrating x-rays with respect to the surrounding structure (so-called positive contrast media) or which let pass penetrating x-rays unhindered (so-called negative contrast media).

Preferred x-ray contrast media are those which are used for imaging of joints (arthrography) and in CT (computer tomography). The computer tomograph is a device for generating sectional images of the human body by means of x-rays.

Although according to the invention also x-rays can be used for detection in the imaging methods this radiation is not preferred due to its harmfulness. Preferably the penetrating radiation is not an ionizing radiation.

As imaging methods are used x-ray images, computer tomography (CT), nuclear spin tomography, magnetic resonance tomography (MRT) and ultrasound, wherein nuclear spin tomography and magnetic resonance tomography (MRT) are preferred.

Thus, as substances which due to their ability of being excited by penetrating radiation allow for the detection of the medical device in in-vivo events by imaging methods especially those contrast media are preferred which are used in computer tomography (CT), nuclear spin tomography, magnetic resonance tomography (MRT) or ultrasound. The mechanism of action of contrast media in MRT is based in effecting a change in the magnetic behavior of the structures to be differentiated.

Moreover, iodine-containing contrast media are preferred which are used in the imaging of vessels (angiography or phlebography) and in computer tomography (CT).

As iodine-containing contrast media the following examples can be mentioned:

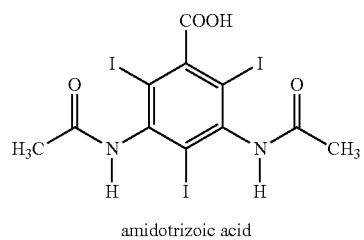

amidotrizoic acid

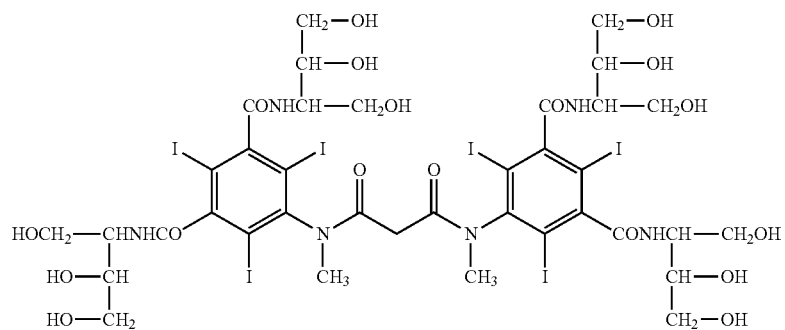

iotrolan

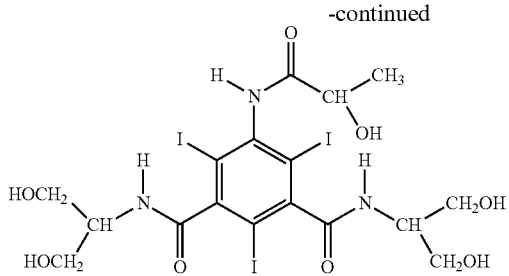
iopamidol

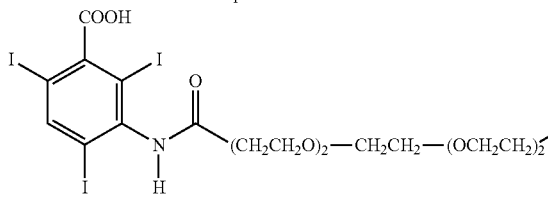
iodoxaminic acid

Another example is Jod-Lipiodol®, a iodinated Oleum papaveris, a poppy seed oil. The mother substance of iodinated contrast media, amidotrizoate, is commercially available in the form of sodium and meglumine salts under the trademarks Gastrografin® and Gastrolux®.

Also gadolinium-containing or superparamagnetic iron oxide particles as well as ferrimagnetic or ferromagnetic iron particles such as nanoparticles are preferred.

Another class of preferred contrast media is represented by the paramagnetic contrast media which mostly contain a lanthanoid.

One of the paramagnetic substances with unpaired electrons is e.g. gadolinium ($Gd^{3+}$) having in total seven unpaired electrons. Furthermore to this group belong europium ($Eu^{2+}$, $Eu^{3+}$), dysprosium ($Dy^{3+}$) and holmium ($Ho^{3+}$). These lanthanoids can be used also in chelated form by using for example hemoglobin, chlorophyll, polyaza acids, polycarboxylic acids and especially EDTA, DTPA, DMSA, DMPS as well as DOTA as chelator.

Examples of gadolinium-containing contrast media are gadolinium diethylenetriaminepentaacetic acid

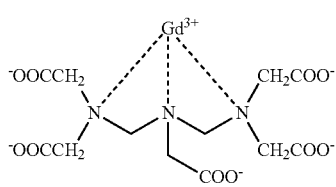
gadopentetic acid (GaDPTA)

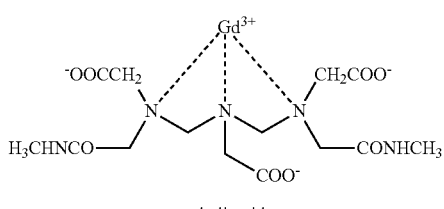
gadodiamide

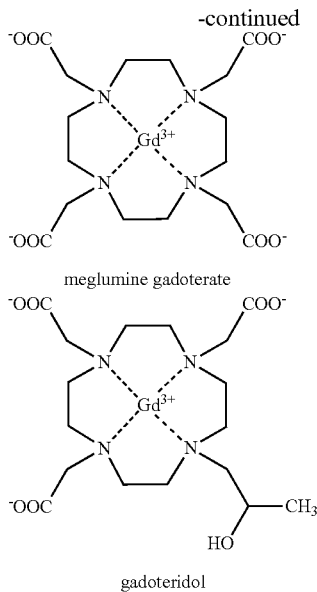
meglumine gadoterate gadoteridol

Further paramagnetic substances which can be used according to the invention are ions of so-called transition metals such as copper ($Cu^{2+}$), nickel ($Ni^{2+}$), chromium ($Cr^{2+}$, $Cr^{3+}$), manganese ($Mn^{2+}$, $Mn^{3+}$) and iron ($Fe^{2+}$, $Fe^{3+}$). Also these ions can be used in chelated form.

The at least one substance which due to its ability of being excited by penetrating radiation allows for the detection of the basic body in in-vivo events by imaging methods is either on the surface of the basic body or inside the basic body.

In one preferred embodiment the inside of the balloon of the catheter in its compressed form is filled with a contrast medium and/or contrast medium analogue. The contrast medium is preferably present as a solution. Besides the properties of the contrast medium or contrast medium analogue as carrier or matrix for the active agent such coatings have the additional advantage of the catheter balloon being better visible, i.e. detectable, in the imaging methods. The expansion of the balloon takes place by expanding the balloon through further filling with a contrast medium solution.

An advantage of this embodiment is that the contrast medium or contrast medium analogue can be reused any times without entering the body and thus does not lead to hazardous side effects.

As contrast medium analogues contrast agent-like compounds are referred to which have the properties of contrast media, i.e. can be made visible with imaging methods to be used during surgery.

A visualization of PCTA associated with these substances can be regarded as advantageous so that a systemic application of contrast medium can be waived. This can be the transport accelerator itself or an additional colorant.

For example, such contrast media or contrast media analogues are used for the absorption of the at least one active agent, and in particular paclitaxel or rapamycin. The catheter balloon (with or without a stent) pr the folds of the catheter balloon can be coated with such a composition. Furthermore, such a liquid solution can escape preferably under pressure from the inside of the catheter balloon through a plurality of micro- and/or nano-pores thus supporting the detachment of a coating located on the balloon surface. The advantage is that the section of the vessel is provided with a sufficient amount of the active agent during short-term dilation, and that the coating of the catheter balloon is detached and pressed to the vascular wall in a steady manner where it remains and is degraded respectively absorbed from the cells.

On the other hand, systems of contrast medium and active agent, especially paclitaxel and rapamycin, are particularly suitable for being applied to micro raw surfaces or into micro cavities wherein such a coating generally has to be covered with a barrier layer which is to burst or to be torn open, until then protecting the mixture of contrast medium and active agent from premature erosion or premature dissolution.

In order to protect such mixtures of contrast medium and active agent from premature release the mixture is applied in or under the folds of the fold balloon or on the surface of the catheter balloon having structural patterns or micro-needles or other fillable cavities, and then coated with a barrier layer. As a barrier layer a polymeric layer can be used, as disclosed for example in WO 2004/052420 A2 or EP 1150622 A1.

Such a barrier layer may consist of polylactides, polyglycolides, polyanhydrides, poyphosphazenes, polyorthoesters, polysaccharides, polynucleotides, polypeptides, polyolefins, vynylchloride polymers, fluorine-containing polymers, teflon, polyvinylacetates, polyvinylalcohols, polyvinylacetals, polyacrylates, polymethacrylates, polystyrene, polyamides, polyimides, polyacetals, polycarbonates, polyesters, polyurethanes, polyisocyanates, polysilicones as well as co-polymers and mixtures of these polymers.

A further option of protecting the coating on the catheter balloon consists in using expandable catheter balloons and in providing them with a wrapper as used in the implantation of self-expanding stents. This wrapper protects the balloon coating from premature detachment and is not removed before the balloon is at the stenotic section of the vessel where it is to be expanded.

Polymeric Matrix

Besides non-polymeric substances for a matrix in which one or more active agents shall be embedded of course the known polymeric substances can be used. As a matrix biocompatible substances can be used which—as a minimal requirement—do not negatively bias the properties and the use of the implant in comparison with the uncoated implant. The matrix is also referred to herein as carrier, carrier system, polymeric carrier or substance-containing coating.

The following biocompatible biodegradable and/or biostable polymers can be used preferably for the coating of the short-term implant:

As biologically stable and only slowly biologically degradable polymers can be mentioned: polyacrylic acid and polyacrylates such as polymethylmethacrylate, polybutylmethacrylate, polyacrylamide, polyacrylonitriles, polyamides, polyetheramides, polyethylenamine, polyimides, polycarbonates, polycarbourethanes, polyvinylketones, polyvinylhalogenides, polyvinyl idenhalogenides, polyvinylethers, polyvinylaromates, polyvinylesters, polyvinylpyrrolidones, polyoxymethylenes, polyethylene, polypropylene, polytetrafluoroethylene, polyurethanes, polyolefine elastomers, polyisobutylenes, EPDM gums, fluorosilicones, carboxymethylchitosane, polyethylenterephthalate, polyvalerates, carboxymethylcellulose, cellulose, rayon, rayontriacetates, cellulose nitrates, cellulose acetates, hydroxyethylcellulose, cellulose butyrates, cellulose acetate-butyrates, ethylvinylacetate copolymers, polysulfones, polyethersulfones, epoxy resins, ABS resins, EPDM gums, silicon prepolymers, silicones such as polysiloxanes, polyvinylhalogenes and copolymers, cellulose ethers, cellulose triacetates, chitosane, chitosane derivatives, polymerizable oils such as linseed oil and copolymers and/or mixtures thereof.

Furthermore, in an upstream step before the coating step a hemocompatible layer can be applied adhesively or preferably covalently on the uncoated surface of the medical device or can be immobilized on the surface of the medical device through cross-linkage, for example with glutardialdehyde. Such a layer which does not activate blood coagulation makes sense because the hemocompatibility of the surface of the medical device is thus enhanced and the thrombosis risk reduced. This coating step is particularly useful when the short-term implant shall be only partially coated. The section not coated with an active agent thus advantageously has a surface which does not activate blood coagulation and is athrombogenic and thus provides much higher safety during and after the exposure of the medical device with the blood.

The preferably hemocompatible layer is produced from the following preferred substances: heparin of native origin as well as regioselectively produced derivatives of differing sulfatation and acetylation degrees in the molecular weight range from the pentasaccharide responsible for the antithrombotic effect to the standard molecular weight of commercially available heparin of about 13 kD, heparan sulfates and their derivatives, oligo- and polysaccharides of the erythrocyte glycocalix, oligosaccharides, polysaccharides, completely desulfated and N-reacetylated heparin, desulfated and N-reacetylated heparin, N-carboxylated and/or partially N-acetylated chitosan, polyacrylic acid, polyetherketones, polyvinylpyrrolidone and/or polyethylene glycol as well as compositions of these substances.

As biologically degradable or resorbable polymers can be used e.g.: polyvalerolactones, poly-ε-decalactones, polylactides, polyglycolides, copolymers of the polylactides and polyglycolides, poly-c-caprolactone, polyhydroxybutyric acid, polyhydroxybutyrates, polyhydroxyvalerates, polyhydroxybutyrate-co-valerates, poly(1,4-dioxane-2,3-diones), poly(1,3-dioxane-2-one), poly-para-dioxanones, polyanhydrides such as polymaleic anhydrides, polyhydroxymethacrylates, fibrin, polycyanoacrylates, polycaprolactonedimethylacrylates, poly-β-maleic acid, polycaprolactonebutyl-acrylates, multiblock polymers such as from oligocaprolactonedioles and oligodioxanonedioles, polyetherester multiblock polymers such as PEG and polybutyleneterephtalate, polypivotolactones, polyglycolic acid trimethyl-carbonates, polycaprolactone-glycolides, poly(g- ethylglutamate), poly(DTH-iminocarbonate), poly(DTE-co-DT-carbonate), poly(bisphenol-A-iminocarbonate), polyorthoesters, polyglycolic acid trimethyl-carbonates, polytrimethylcarbonates, polyiminocarbonates, poly(N-vinyl)-pyrrolidone, polyvinyl alcohols, polyesteramides, glycolated polyesters, polyphosphoesters, polyphosphazenes, poly[p-carboxyphenoxy)propane], polyhydroxypentanoic acid, polyanhydrides, polyethyleneoxide-propyleneoxide, soft polyurethanes, polyurethanes having amino acid residues in the backbone, polyether esters such as polyethyleneoxide, polyalkeneoxalates, polyorthoesters as well as their copolymers, carrageenanes, fibrinogen, starch, collagen, protein based polymers, polyamino acids, synthetic polyamino acids, zein, modified zein, polyhydroxyalkanoates, pectic acid, actinic acid, modified and non modified fibrin and casein, carboxymethylsulfate, albumin, furthermore hyaluronic acid, heparan sulfates, heparin, chondroitine sulfate, dextran, β-cyclodextrines, copolymers with PEG and polypropylene glycol, gummi arabicum, guar, gelatine, collagen, collagen-N-hydroxysuccinimide, modifications and copolymers and/or mixtures of the afore mentioned substances.

Additionally, the surface of the balloon with or without a stent can be provided with an athrombogenic or inert or biocompatible surface, or generally with a coating and particularly with a polymeric or non-polymeric coating. For generating a hemocompatible, respectively blood-friendly, surface on the catheter balloon the aforementioned oligosaccharides, polysaccharides and particularly the described heparin and chitosan derivatives can be preferably used according to general formula Ia and Ib.

Particularly preferred polymers are polysulfones, polyethersulfones, silicones, chitosan, polyacrylates, polyamides, polyetheramides, polyurethanes, polylactides, polyglycolides, copolymers of polylactides and polyglycolides, polyhydroxybutyric acid, polyhydroxybutyrates, polyhydroxyvalerates, polyhydroxybutyrate-co-valerates, poly(1,4-dioxane-2,3-diones), poly(1,3-dioxane-2-one), poly-para-dioxanones, polyanhydrides, polyester, PEG, hyaluronic acid, heparan sulfate, heparin, chondroitin sulfate, dextram and □-cyclodextrins.

Balloon with a Crimped Stent

A further preferred embodiment of the present invention comprises a catheter balloon with a crimped stent.

In this embodiment there are 4 variants to be selected and used corresponding to the vessel stenosis that needs treatment.

Variant [A] is a catheter balloon with a crimped non-resorbable and uncoated stent.

In variant [B] the non-resorbable stent is coated with a substance-releasing carrier system.

Variant [C] comprises a resorbable uncoated stent and variant [D] is a catheter balloon with a resorbable substance-releasing stent.

Variant [A]:

As a substance-releasing system, generally a substance-releasing coating, on the stent is not always desirable and in some cases the problem of late thrombosis may occur variant [A] offers an ideal system for keeping open a severely occluded corporal lumen as for example the bile duct, oesophagus, unitary tract, pancreas, renal tract, pulmonary tract, trachea, small intestine and large intestine and particularly blood vessels with a permanent stent without a coating, wherein nevertheless the application of an active agent is optional.

The catheter balloon according to variant [A] is coated with a pure substance layer or a carrier containing an active agent, and during dilation on the one hand the stent is placed and on the other hand an active agent is applied at least along the whole length of the stent, and preferably beyond, which enables a controlled incorporation and prevents an overgrowing of the stent with mostly smooth muscle cells. As an active agent or composition of active agents the aforementioned active agents and especially paclitaxel and/or rapamycin can be used.

Preferably the catheter balloon is coated with an active agent with or without a carrier system in such away that the balloon coating extends both stent ends, preferably by 10-20% of total stent length over an end of the stent. Thus the active agent is transferred during dilation also to the section of the vessel at both ends of the stent where the stent doesn't reach, and the active agent is transferred all over the vascular wall located between the expanding, respectively expanded, stent struts.

This embodiment has the advantage that the stent surface doesn't have an active agent inhibiting or killing cells, particularly smooth muscle cells, which contact directly the stent surface. In contrast, a sufficient amount of the active agent is applied in the recesses between the stent struts so that the rapid overgrowth of the stent starting from the recesses and continuing to the inside of the stent which eventually leads to in-stent restenosis is contained respectively reduced to a tolerable degree.

As a substance-coated stent releases the active agent only from its surface and not from the recesses of the stent struts or from the end of the stent respectively the area extending it and moreover releases it to the adjacent tissue which should not be inhibited or killed, according to variant [A] the active agent is exactly applied where it is needed. It is preferred further that when the catheter balloon is coated at its distal and proximal end for some mm over the end of the stent the covering of the vascular wall with the active agent extends the end of the stent by some mm for providing a sufficient amount of the active agent also the terminal sections of the stent being incorporated in the vessel.

Thus the catheter balloon is preferably coated with the active agent with or without a carrier and subsequently an uncoated stent is crimped onto the balloon.

Variant [B] can be achieved when a non-resorbable stent as in variant [A] is crimped onto a balloon and subsequently the stent and the balloon are coated with an active agent.

The term "non-resorbable" means that the stent is a permanent implant which will not or only gradually be dissolved under physiological conditions. Such stents are made for example of stainless steel, titanium, chrome, vanadium, tungsten, molybdenum, gold, Nitinol, magnesium, zinc, iron, alloys of the aforementioned metals as well as ceramics or also biostable polymers.

If a catheter balloon with a crimped stent is coated concomitantly a solution of the pure active agent is preferably used in a solvent that affects the catheter balloon as little as possible but nevertheless preferably is wetting and additionally sufficiently fluid to flow between the struts of the crimped stent when being compressed.

This embodiment is suitable for a spontaneous release of a relatively huge amount of the active agent, since the recesses of the stent struts and the recesses between the inner surface of the stent and the surface of the catheter balloon serve as a pool for the active agent.

The difference to variant [A] consists mainly in the applicable amount of the active agent, as according to the aforementioned method a considerably higher amount of an active agent or composition of active agents can be applied to the stent and the catheter balloon.

For a coating solution hydrophobic active agents as e.g. paclitaxel solutions in e.g. dimethyl sulfoxide (DMSO), chloroform, ethanol, acetone, methyl acetate and hexane and their mixtures or e.g. of rapamycin in acetic acid ethyl ester, methanol/ethanol mixtures, ethanol/water mixtures or ethanol are suitable. Of course also other active agents can be used.

It is also possible to add a carrier to the solution with the active agent wherein polymeric carriers, however, are rather seldom used when the catheter balloon is coated together with the crimped stent. If a carrier system shall be used rather non-polymeric carriers as for example contrast media or contrast media analogues as well as biocompatible organic substances are suitable which improve the coating properties and enhance the uptake of the active agent into the vessel, as for example amino acids, sugars, vitamins, saccharides, 2-pyrrolidone, acetyltributyl and acetyltriethyl citrate, tributyl and triethyl citrate, benzoic acid benzyl ester, triethyl and dimethyl phthalate, fatty acid esters such as isopropyl myristate and palmitate, triacetine and the like. Equally suitable are mixtures of these substances. For example the mixture of the polysaccharides carrageenan, lecithin and glycerine proves to be extremely suitable. Also physiologically acceptable salts can be used as a matrix for embedding the active agent.

Also in this variant the balloon is preferably coated beyond the surface covered by the stent. Preferably the coated area of the balloon extending beyond the stent ends not exceed 20% of total stent length, more preferred not more than 15% and particularly preferred not more than 10% of total stent length.

Generally a thorough coating is advantageous in variant [A] as in variant [B], i.e. the catheter balloon according to variant [A] or the stent and the catheter balloon according to variant [B] are thoroughly provided with a coating.

The variants [A] and [B] can additionally be modified by providing an uneven coating by using a gradient, i.e. a concentration gradient of the active agent on the balloon, respectively balloon and stent, surface is generated. For example, a higher concentration of the active agent can be applied on the middle section of the balloon, or on one or both ends of the catheter balloon, or on the middle section and on one or both ends of the catheter balloon.

Furthermore, only on one position or section of the catheter balloon a higher concentration of the active agent can be applied than on the rest of the surface. For example, the ends of the stent need special attention particularly in the early phase after the implantation since these transitional sections have a higher risk. Here, any combination is conceivable.

Variants [C] and [D] arguably will become ever the more important embodiments since both embodiments are no permanent implants.

Both variants use biodegradable, i.e. bioresorbable stents. Such stents degradable under physiological conditions will be completely degraded in the patient's body during a few weeks up to one or two years.

Biodegradable stents consist of metals as for example magnesium, calcium or zinc, or also of organic compounds as for example polyhydroxybutyrate, chitosan or collagen.

A bioresorbable metal stent mainly made of magnesium is disclosed in the European patent EP 1 419 793 B1. The German disclosure describes stents made of magnesium alloys and zinc alloys. Bioresorable stents made of magnesium, calcium, titanium, zirconium, niobium, tantalum, zinc or silicon or of alloys or mixtures of the aforementioned substances are disclosed in the German patent application DE 198 56 983 A1. Explicit examples for stents made of a zinc-calcium alloy are disclosed.

Further bioresorbable stents made of magnesium, titanium, zirconium, niobium, tantalum, zinc and/or silicon as component A and lithium, potassium, calcium, manganese and/or iron as component B are described in the European patent application EP 0 966 979 A2. Explicit examples are disclosed for stents made of a zinc-titanium alloy with a titanium percentage by weight of 0.1 to 1% and a zinc-calcium alloy with a zinc percentage per weight of 21:1.

A biodegradable stent made of the organic compound polyhydroxybutyrate (PHB) and other polyhydroxyalkanoates is disclosed in U.S. Pat. Nos. 6,548,569 B1, 5,935,506, 6,623, 749 B2, 6,838,493 B2 and 6,867,247 B2.

U.S. Pat. No. 6,245,103 B1 further mentions polydioxanones, polycaprolactones, polygluconates, poly(lactic acid)-polyethylene oxide-copolymers, modified cellulose, collagen, poly(hydroxybutyrate), polyanhydrides, polyphosphoesters and polyamino acids as other suitable biodegradable material for stents.

U.S. Pat. No. 6,991,647 B2 further lists polyglycolic acid, polylactides, polyphosphate esters and poly-□-caprolactone as eligible biodegradable organic polymers.

Basically all biodegradable stents can be produced from the following substances or mixtures of the following substances:

polyvalerolactones, poly-ϵ-decalactones, polylactides, polyglycolides, copolymers of the polylactides and polyglycolides, poly-ϵ-caprolactone, polyhydroxybutyric acid, polyhydroxybutyrates, polyhydroxyvalerates, polyhydroxybutyrate-co-valerates, poly(1,4-dioxane-2,3-diones), poly(1,3-dioxane-2-one), poly-para-dioxanones, polyanhydrides such as polymaleic anhydrides, polyhydroxymethacrylates, fibrin, polycyanoacrylates, polycaprolactonedimethylacrylates, poly-β-maleic acid, polycaprolactonebutylacrylates, multiblock polymers such as from oligocaprolactondioles and oligodioxanonedioles, polyetherester multiblock polymers such as PEG and poly(butyleneterephtalates), polypivotolactones, polyglycolic acid trimethyl-carbonates, polycaprolactone-glycolides, poly(g-ethylglutamate), poly(DTH-iminocarbonate), poly(DTE-co-DT-carbonate), poly(bisphenol-A-iminocarbonate), polyorthoesters, polyglycolic acid trimethyl-carbonates, polytrimethylcarbonates, polyiminocarbonates, poly(N-vinyl)-pyrrolidone, polyvinylalcoholes, polyesteramides, glycolated polyesters, polyphosphoesters, polyphosphazenes, poly[p-carboxyphenoxy)propane], polyhydroxypentanoic acid, polyethyleneoxide-propyleneoxide, soft polyurethanes, polyurethanes having amino acid residues in the backbone, polyether esters such as polyethyleneoxide, polyalkeneoxalates, polyorthoesters as well as their copolymers, carrageenanes, fibrinogen, starch, collagen, protein based polymers, polyamino acids, synthetic polyamino acids, zein, modified zein, polyhydroxyalkanoates, pectic acid, actinic acid, modified and non-modified fibrin and casein, carboxymethyl sulfate, albumin, hyaluronic acid, heparan sulfates, heparin, chondroitine sulfate, dextran, β-cyclodextrines, and copolymers with PEG and polypropyleneglycol, gummi arabicum, guar, gelatine, collagen, collagen-N-hydroxysuccinimide, modifications and copolymers of the aforementioned substances.

In variant [C] such a bioresorbable stent made of metal or organic polymers is criped onto the coated catheter balloon.

The coating of the catheter balloon is carried out similar to variant [A]. Variants [C] and [D] have the advantage that the stent dissolves itself completely after a period of a few weeks up to ca. 18 months and thus no permanent exogenous material remains in the patient that might cause chronic inflammations. Via the coated stent a sufficient amount of active agent is applied during dilation so that the stent in the first place can be incorporated in a controlled manner and only after the incorporation starts disintegrating in such a way that no fragments can be washed away through the vessel respectively the bloodstream.

In variant [D] the active agent or the combination of active agents can be applied to the surface of the stent as a pure substance layer, or can be embedded on the surface of the stent in a non-polymeric matrix as for example a contrast medium, composition of contrast media or contrast medium analogue, or be present in a polymeric carrier on the surface of the stent as for example one of the aforementioned biodegradable polymers, and/or be embedded into the biodegradable stent material itself.

Thereby, especially in variant [D] a plethora of options is given for applying or embedding one or more active agents on or into a biodegradable stent. Of course there is also the option to embed one or more active agents into the biodegradable material, i.e. into the stent itself, and to cover the stent additionally with an active agent or with a polymeric or non-polymeric carrier containing one or more active agents. Moreover, the stent or the coating containing the active agent can be provided with a biodegradable barrier layer or a hemocompatible layer so that two-layer systems or also multi-layer systems are possible embodiments.

Furthermore, also combinations of active agents are conceivable in which a combination of active agents is applied into or onto the stent, or a combination of active agents is generated when another active agent is in the stent than on the stent.

Moreover, variants [B] and [D] offer an option of applying a combination of active agents when another active agent is on the catheter balloon than on the stent.

On the catheter balloon an active agent is preferably applied which becomes effective during a few hours or days after dilation, wherein on the stent or in the biodegradable stent a second active agent can be applied or embedded in another concentration which yields long-term effects and is released during the time of biodegradation of the stent.

It is particularly preferred that there is a cytotoxic dosage of an active agent on the catheter balloon and on the stent and/or in the biodegradable stent a cytostatic dosage of the same or of another active agent.

A particularly preferred embodiment contains paclitaxel on the catheter balloon in a cytotoxic dosage and in a polymeric coating of a metal stent or in a biodegradable coating of the bioresorbable stent in a cytostatic concentration.

A further particularly preferred embodiment is a combination of paclitaxel in a cytotoxic or a cytostatic dosage on the catheter balloon and a preferably cytostatic dosage of rapamycin on or in the biodegradable stent.

The last combinations allow for a combinational therapy with a rapidly released active agent in a preferably high and/or cytotoxic concentration and a gradually released active agent in a preferably lower and/or cytostatic concentration.

In the used biostable (non-resorbable) as well as in the biodegradable stents it is preferred to provide a hemocompatible base coating. This is particularly advantageous in non-resorbable stents since these long-term implants should be permanently hemocompatible. This hemocompatible coating ensures that with the fading out of the effect of the active agent and the degradation of the matrix no reactions directed to the subsisting exogenous surface occur that in the long run may also lead to a re-occlusion of the blood vessel. The hemocompatible coating directly covering the stent consists preferably of heparin of native origin and also of synthetically produced derivatives with different degrees of sulfation and acetylation in the molecular weight range from the pentasaccharide responsible for the antithrombotic effect up to the standard molecular weight of commercially available heparin, heparan sulfates and their derivatives, oligo- and polysaccharides of the erythrocyte glycocalix reproducing perfectly the athrombogenic surface of erythrocytes, since here in contrast to phosphorylcholine the real contact between blood and erythrocyte surface takes place, oligosaccharides, polysaccharides, completely desulfated and N-reacetylated heparin, desulfated and N-reacetylated heparin, N-carboxymethylated and/or partially N-acetylated chitosan, polyacrylic acid, polyvinylpyrrolidone and/or polyethylene glycol as well as compositions of these substances. These stents are produced with a hemocompatible coating by providing conventional generally uncoated stents and preferably applying covalently a hemocompatible layer which masks permanently the surface of the implant after the release of the active agent and thus after the fading out of the actions of the active agent and the degradation of the matrix. Therefore this hemocompatible coating is applied directly to the surface of the stent.

Thus a preferred embodiment of the present invention relates to a stent of any material the surface of which is masked by the application of glycocalix components from blood cells, esothelial cells and mesothelial cells. The glycocalix is the outmost layer of for example blood cells, esothelial cells and mesothelial cells by which these cells become blood-friendly (hemocompatible). The components of this outmost layer (glycocalix) of blood cells, esothelial cells and/or mesothelial cells are preferably enzymatically severed from the cell surface, separated from the cells and used as a coating material for the stents. Among these glycocalix components are oligosaccharide, polysaccharide and lipid components of glycoproteins, glycolipids and proteoglycans such as glycophorins, glycosphingolipids, hyaluronic acids, chondroitin sulfates, dermatan sulfates, heparan sulfates and also keratan sulfates. Methods for isolation and use of these substances as a coating material are described in detail in the European patent EP 1 152 778 B1 by the company founders of Hemoteq AG, Mr. Michael Hoffmann, PhD, and Mr. Roland Horres, MSc.

The covalent binding is the same as in hemoparin (see Examples No. 9, 14).

Further preferred embodiments have an undermost coating applied directly on the balloon surface of desulfated and N-reacetylated heparin and/or N-carboxymethylated and/or partially N-acetylated chitosan. These compounds as well as the glycocalix components have been shown in a variety of studies as an excellent hemocompatible coating and render the surface blood-friendly after the superior active agent- and/or carrier-containing layers have been eliminated or biologically degraded. Such particularly preferred materials for the coating of the stent surface are disclosed in European patent No. EP 1 501 565 B1 of the company Hemoteq AG. On this inferior hemocompatible layer one or more active agent-containing layers and/or carrier or polymeric layers with or without an active agent are applied.

These heparin or chitosan derivatives are polysaccharides according to the general formula Ia

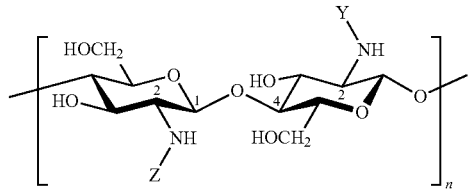

as well as structurally related polysaccharides of the general formula Ib

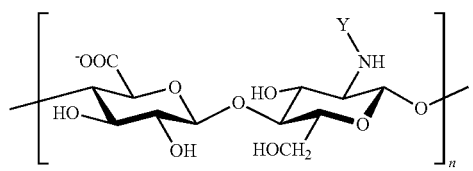

The polysaccharides according to formula Ia have molecular weights from 2 kD to 400 kD, preferably from 5 kD to 150 kD, more preferably from 10 kD to 100 kD, and particularly preferably from 30 kD to 80 kD. The polysaccharides according to formula Ib have molecular weights from 2 kD to 15 kD, preferably from 4 kD to 13 kD, more preferably from 6 kD to 12 kD, and particularly preferably from 8 kD to 11 kD. The variable n is an integer ranging from 4 to 1050. Preferably, n is an integer from 9 to 400, more preferably from 14 to 260, and particularly preferably an integer between 19 and 210.

The general formulas Ia and Ib represent a disaccharide, which is to be seen as a basic unit of the polysaccharide according to invention and forms the polysaccharide by stringing together said basic unit n times. Said basic unit comprising two sugar molecules does not intend to suggest that the general formulas Ia and Ib only relate to polysaccharides having an even number of sugar molecules. Of course, the general formula Ia and the formula Ib also comprise polysaccharides having an odd number of sugar units. Hydroxy groups are present as terminal groups of the oligosaccharides and polysaccharides, respectively.

The groups Y and Z, independently of each other, represent the following chemical acyl or carboxyalkyl groups: —CHO, —COCH$_3$, —COC$_2$H$_5$, —COC$_3$H$_7$, —COC$_4$H$_9$, —COC$_5$H$_{11}$, —COCH(CH$_3$)$_2$, —COCH$_2$CH(CH$_3$)$_2$, —COCH(CH$_3$)C$_2$H$_5$, —COC(CH$_3$)$_3$, —CH$_2$COO$^-$, —C$_2$H$_4$COO$^-$, —C$_3$H$_6$COO$^-$, —C$_4$H$_8$COO$^-$.

Preferred are the acyl groups —COCH$_3$, —COC$_2$H$_5$, —COC$_3$H$_7$ and the carboxyalkyl groups —CH$_2$COO$^-$, —C$_2$H$_4$COO$^-$, —C$_3$H$_6$COO$^-$. More preferred are the acetyl and propanoyl groups and the carboxymethyl and carboxyethyl groups. Particularly preferred are the acetyl group and the carboxymethyl group.

In addition, it is preferred that the group Y represents an acyl group, and the group Z represents a carboxyalkyl group. It is more preferred if Y is a group —COCH$_3$, —COC$_2$H$_5$ or —COC$_3$H$_7$ and in particular —COCH$_3$. Moreover, it is further preferred if Z is a carboxyethyl or carboxymethyl group, the carboxymethyl group being particularly preferred.

The disaccharide basic unit shown by formula Ia comprises each a substituent Y and a further group Z. This is to make clear that the polysaccharide of the invention comprises two different groups, namely Y and Z. Herein, the general formula Ia should not only comprise polysaccharides containing the groups Y and Z in a strictly alternating sequence, which would result from stringing together the disaccharide basic unit, but also polysaccharides carrying the groups Y and Z in a completely random sequence at the amino groups. Further, the general formula Ia should also comprise polysaccharides containing the groups Y and Z in different numbers. The ratios of the number of Y groups to the number of X groups can be between 70%:30%, preferably between 60%:40%, and particularly preferably 45%:55%. Especially preferred are polysaccharides of the general formula Ia carrying on substantially half of the amino groups the Y residue and on the other half of the amino groups the Z residue in a merely random distribution. The term "substantially half" means exactly 50% in the most suitable case but should also comprise the range from 45% to 55% and especially from 48% to 52% as well.

Preferred are the compounds of the general formula Ia, wherein the groups Y and Z have the following meanings:
Y=—CHO and Z=—C$_2$H$_4$COO$^-$
Y=—CHO and Z=—CH$_2$COO$^-$
Y=—COCH$_3$ and Z=—C$_2$H$_4$COO$^-$
Y=—COCH$_3$ and Z=—CH$_2$COO$^-$
Y=—COC$_2$H$_5$ and Z=—C$_2$H$_4$COO$^-$
Y=—COC$_2$H$_5$ and Z=—CH$_2$COO$^-$ Especially preferred are the compounds of the general formula Ia, wherein the groups Y and Z have the following meanings:
Y=—CHO and Z=—C$_2$H$_4$COO$^-$
Y=—COCH$_3$ and Z=—CH$_2$COO$^-$ Especially preferred are the compounds of the general formula Ib, wherein Y is one of the following groups: —CHO, —COCH$_3$, —COC$_2$H$_5$ or —COC$_3$H$_7$. Further preferred are the groups —CHO, —COCH$_3$, —COC$_2$H$_5$ and especially preferred is the group —COCH$_3$.

The compounds of the general formula Ib contain only a minor amount of free amino groups. As with the ninhydrin test free amino groups could not be detected anymore, it can be concluded due to the sensitivity of this test, that less than 2%, preferred less than 1% and especially preferred less than 0.5% of all of —NH—Y groups are present as free amino groups, i.e. at this low percentage of the groups —NH—Y that Y represents hydrogen.

As the polysaccharides of the general formula Ia and Ib contain carboxylate groups and amino groups, the general formulas Ia and Ib also comprise alkali and alkaline earth metal salts of the respective polysaccharides. Thus, alkali metal salts such as the sodium salt, potassium salt, lithium salt or alkaline earth metal salts such as the magnesium salt or calcium salt can be mentioned. Further, with ammonia, primary, secondary, tertiary and quaternary amines, pyridine and pyridine derivatives, ammonium salts, preferably alkyl ammonium salts and pyridinium salts can be generated. The bases forming salts with the polysaccharides include inorganic and organic bases such as NaOH, KOH, LiOH, CaCO$_3$, Fe(OH)$_3$, NH$_4$OH, tetraalkyl ammonium hydroxides and similar compounds.

The compounds according to the invention of the general formula Ib can be prepared from heparin or heparan sulfates by first substantially complete desulfation of the polysaccharide and subsequently substantially complete N-acylation. The term "substantially completely desulfated" refers to a desulfation degree of above 90%, preferred above 95% and especially preferred above 98%. The desulfation degree can be determined according to the so called ninhydrin test which detects free amino groups. The desulfation takes place to the extent that with DMMB (dimethylmethylene blue) no color reaction is obtained. This color test is suitable for the detection of sulfated polysaccharides but its detection limit is not known in technical literature. The desulfation can be carried out for example by pyrolysis of the pyridinium salt in a solvent mixture. Especially a mixture of DMSO, 1,4-dioxane and methanol has proven of value.

Heparan sulfates as well as heparin were desulfated via total hydrolysis and subsequently reacylated. Thereafter the number of sulfate groups per disaccharide unit (S/D) was determined by $^{13}$C-NMR. The following table 1 shows these results on the example of heparin and desulfated, reacetylated heparin (Ac-heparin).

TABLE 1

Distribution of functional groups per disaccharide unit on the example of heparin and Ac-heparin as determined by $^{13}$C-NMR-measurements.

|  | 2-S | 6-S | 3-S | NS | N—Ac | NH$_2$ | S/D |
|---|---|---|---|---|---|---|---|
| Heparin | 0.63 | 0.88 | 0.05 | 0.90 | 0.08 | 0.02 | 2.47 |
| Ac-heparin | 0.03 | 0 | 0 | 0 | 1.00 | — | 0.03 |

2-S, 3-S, 6-S: sulfate groups in position 2, 3 or 6
NS: sulfate groups on the amino groups
N—Ac: acetyl groups on the amino groups
NH$_2$: free amino groups
S/D: sulfate groups per disaccharide unit A sulfate content of about 0.03 sulfate groups/disaccharide unit (S/D) in the case of Ac-heparin in comparison with about 2.5 sulfate groups/disaccharide unit in the case of heparin was reproducibly obtained.

These compounds of the general formulas Ia and Ib have a content of sulfate groups per disaccharide unit of less than 0.2, preferred less than 0.07, more preferred less than 0.05 and especially preferred less than 0.03 sulfate groups per disaccharide unit.

Substantially completely N-acylated refers to a degree of N-acylation of above 94%, preferred above 97% and especially preferred above 98%. The acylation runs completely in such a way that with the ninhydrin reaction for detection of free amino groups no colour reaction is obtained anymore. As acylation agents carboxylic acid chlorides, —bromides or —anhydrides are preferably used. For example, acetic anhydride, propionic anhydride, butyric anhydride, acetic acid chloride, propionic acid chloride or butyric acid chloride are suitable for the synthesis of the compounds according to the invention. Especially suitable are carboxylic anhydrides as acylation agents.

Peptides, Nucleotides, Saccharides

Furthermore, peptides, proteins, nucleotides and saccharides are very suitable matrix materials which on the one hand can embed active agents and on the other hand show a certain affinity to the cell wall and can be biologically degraded after the transfer onto the cell wall.

Examples for such compounds can be chitosan, chitin, glycosamino glycans as heparin, dermatan sulfates, heparan sulfates, chondroitin sulfate and hyaluronic acid, collagen, carrageenan, agar-agar, carob gum, fibrin, cellulose, rayon, peptides with 50 to 500 amino acids, nucleotides with 20 to 300 bases and saccharides with 20 to 400 sugar molecules. Such carriers have a certain affinity to biological tissue and can provide a sufficient transfer of the active agent onto the vascular wall during short-term dilation.

Preferred are polysaccharides with a molecular weight from 2 kD to 400 kD, preferably from 5 kD to 150 kD, more preferably from 10 kD to 100 kD and particularly preferably from 30 kD to 80 kD. The preferred oligo- and/or polysaccharides are characterized in that they contain a great number of N-acylglucosamine or N-acylgalactosamine molecules as monomers. This means that 40 to 60%, preferably 45-55% and particularly preferably 48-52% of the monomers are N-acylglucosamine or N-acylgalactosamine and that substantially the rest of the sugar monomers each have a carboxyl residue. The oligo- and/or polysaccharides usually thus consist to over 95%, preferably over 98% of only two sugar monomers wherein one monomer carries a carboxyl residue and the other one a N-acyl residue.

A sugar monomer of the preferred oligo- and/or polysaccharides is N-acylglucosamine or N-acylgalactosamine, preferably N-acetylglucosamine or N-acetylgalactosamine, and the other one is an uronic acid, preferably glucuronic acid and iduronic acid.

Preferred are oligosaccharides and/or polysaccharides substantially consisting of the sugar glucosamine resp. galactosamine, substantially the half of the sugar units carrying an N-acyl group, preferably an N-acetyl group; and the other half of the glucosamine units carrying a carboxyl group directly bonded via the amino group or bonded via one or more methylenyl groups. These carboxylic acid groups bonded to the amino group are preferably carboxymethyl or carboxyethyl groups. Further are preferred oligosaccharides and/or polysaccharides, wherein substantially the half, i.e. 48-52%, preferred 49-51% and especially preferred 49.5-50.5%, consists of N-acylglucosamine resp. N-acylgalactosamine, preferably of N-acetylglucosamine or N-acetylgalactosamine, and substantially the other half thereof consists of an uronic acid, preferably glucuronic acid and iduronic acid. Particularly preferred are oligosaccharides and/or polysaccharides showing a substantially alternating sequence (i.e. despite of the statistic deviation ratio in the case of the alternating connection) of the two sugar units. The ratio of the deviated connections should be under 1%, preferred under 0.1%.

Surprisingly, it has been shown that for the uses according to the invention in particular substantially desulfated and substantially N-acylated heparin as well as partially N-carboxyalkylated and N-acylated chitosan as well as desulfated and substantially N-acylated dermatan sulfate, chondroitin sulfate and also chain length reduced hyaluronic acid are especially suitable. In particular, N-acetylated heparin as well as partially N-carboxymethylated and N-acetylated chitosan are suitable for the hemocompatible coating.

The desulfation and acylation degrees defined by "substantially" were already defined more above. The term "substantially" is intended to make clear that statistic deviations have to be taken into consideration. A substantially alternating sequence of the sugar monomers means that as a rule two equal sugar monomers are not bonded to each other, but does not completely exclude such an erroneous linkage. Correspondingly, "substantially the half" means nearly 50%, but permits slight variations, because especially with biosynthetically produced macromolecules, the most suitable case is never achieved, and certain deviations have always to be taken into consideration as enzymes do not work perfectly and catalysis usually involves a certain rate of errors. In the case of natural heparin, however, there is a strictly alternating sequence of N-acetylglucosamine and uronic acid monomers.

For example, it was found that a mixture of carrageenan with phosphatidylcholine and glycerine is particularly adhesive to the cell wall. As a matrix for the active agent or the combination of active agents adhesive to the outer cell membrane such mixtures of polysaccharides with membrane-permeable substances can provide a controlled transfer of the active agent into the cytosol over a considerably longer period than the short-term contact of the medical device with the vascular wall would allow for.

Furthermore, a process for the hemocompatible coating of surfaces is disclosed, which are intended for direct blood contact. In said process, a natural and/or artificial surface is provided, and the oligosaccharides and/or polysaccharides described above are immobilized on said surface.

The immobilisation of the oligosaccharides and/or polysaccharides on these surfaces can be achieved via hydrophobic interactions, van der Waals forces, electrostatic interactions, hydrogen bonds, ionic interactions, cross-linking of the oligosaccharides and/or polysaccharides and/or by covalent bonding onto the surface. Preferred is the covalent linkage of the oligosaccharides and/or polysaccharides, more preferred the covalent single-point linkage (side-on bonding), and especially preferred the covalent end-point linkage (end-on bonding).

The term "substantially the rest of the sugar monomers" means that 93% of the remaining sugar monomers, preferably 96% and particularly preferably 98% of the remaining 60%-40% of the sugar monomers carry a carboxyl residue.

Thus particularly short-term implants are preferred which are provided with this hemocompatible coating of the aforementioned heparin derivatives, chitosan derivatives and/or oligo- and polypeptides from which an enhanced biocompatibility may be required during the time of exposure, as for example it is advantageous in a short-term implant that not completely, but partially coated with an active agent if the surface not coated with an active agent displays an improved biocompatibility. The hemocompatible layer is equally useful if during the short-term stay of the implant in the organism the uncoated metal surface is partially or completely exposed.

In order to improve the adhesion of such carrier substances peptides, proteins, pronucleotides, nucleotides and saccharides can be cross-linked what can be achieved for example with glutaraldehyde.

Oils and Fats as Carrier Substances

Besides the above mentioned biostable and biodegradable polymers as carrier matrix for transport mediators and active agents also physiologically acceptable oils, fats, lipids, lipoids and waxes can be used. WO 03/022265 A1 describes oily formulations of paclitaxel which can be used also. Particularly preferred are, however, oils and fats that can be cured, respectively autopolymerized.

As such oils, fats and waxes which can be used as carrier substances or layers without an active agent, especially top layers, substances are suitable which can be represented by the following general formulas:

—COOCH($CH_3$)$_2$, —COOC($CH_3$)$_3$, —OOC—$CH_3$, —OOC—$C_2H_5$, —OOC—$C_3H_7$, —OOC-cyclo-$C_3H_5$, —OOC—CH($CH_3$)$_2$, —OOC—C($CH_3$)$_3$, —$CONH_2$, —$CONHCH_3$, —$CONHC_2H_5$, —$CONHC_3H_7$, —CON($CH_3$)$_2$, —CON($C_2H_5$)$_2$, —CON($C_3H_7$)$_2$, —$NH_2$, —$NHCH_3$, —$NHC_2H_5$, —$NHC_3H_7$, —NH-cyclo-$C_3H_5$, —NHCH($CH_3$)$_2$, —NHC($CH_3$)$_3$, —N($CH_3$)$_2$, —N($C_2H_5$)$_2$, —N($C_3H_7$)$_2$, —N(cyclo-$C_3H_5$)$_2$, —N[CH($CH_3$)$_2$]$_2$, —N[C($CH_3$)$_3$]$_2$, —$SOCH_3$, —$SOC_2H_5$, —$SOC_3H_7$, —$SO_2CH_3$, —$SO_2C_2H_5$, —$SO_2C_3H_7$, —$SO_3H$, —$SO_3CH_3$, —$SO_3C_2H_5$, —$SO_3C_3H_7$, —$OCF_3$, —$OC_2F_5$, —O—$COOCH_3$, —O—$COOC_2H_5$, —O—$COOC_3H_7$, —O—COO-cyclo-$C_3H_5$, —O—COOCH($CH_3$)$_2$, —O—COOC($CH_3$)$_3$, —NH—CO—$NH_2$, —NH—CO—$NHCH_3$, —NH—CO—$NHC_2H_5$, —NH—CO—N($CH_3$)$_2$, —NH—CO—N($C_2H_5$)$_2$, —O—CO—$NH_2$, —O—CO—$NHCH_3$, —O—CO—$NHC_2H_5$, —O—CO—$NHC_3H_7$, —O—CO—N($CH_3$)$_2$, —O—CO—N($C_2H_5$)$_2$; —O—CO—$OCH_3$, —O—CO—$OC_2H_5$, —O—CO—$OC_3H_7$, —O—CO—O-cyclo-$C_3H_5$, —O—CO—OCH($CH_3$)$_2$, —O—CO—OC($CH_3$)$_3$, —$CH_2F$, —$CHF_2$, —$CF_3$, —$CH_2Cl$, —$CH_2Br$, —$CH_2I$, —$CH_2$—$CH_2F$, —$CH_2$—$CHF_2$, —$CH_2$—$CF_3$, —$CH_2$—$CH_2Cl$; —$CH_2$—$CH_2Br$, —$CH_2$—$CH_2I$, —$CH_3$, —$C_2H_5$, —$C_3H_7$, -cyclo-$C_3H_5$, —CH($CH_3$)$_2$, —C($CH_3$)$_3$, —$CH_2$—CH($CH_3$)$_2$, —CH($CH_3$)—$C_2H_5$, —Ph, —$CH_2$—Ph, —$CPh_3$, —CH=$CH_2$, —$CH_2$—CH=$CH_2$, —C($CH_3$)=$CH_2$, —CH=CH—$CH_3$, —$C_2H_4$—CH=$CH_2$, —CH=C($CH_3$)$_2$, —C≡CH, —C≡C—$CH_3$, —$CH_2$—C≡CH; X is an ester group or amide group and especially —O-alkyl, —O—CO-alkyl, —O—CO—O-alkyl, —O—CO—N-dialkyl, —CO—NH-alkyl, —CO—N-dialkyl, —CO—O-alkyl, —CO—OH, —OH; m, n, p, q, r, s and t are independently of each other integers from 0 to 20, preferred from 0 to 10.

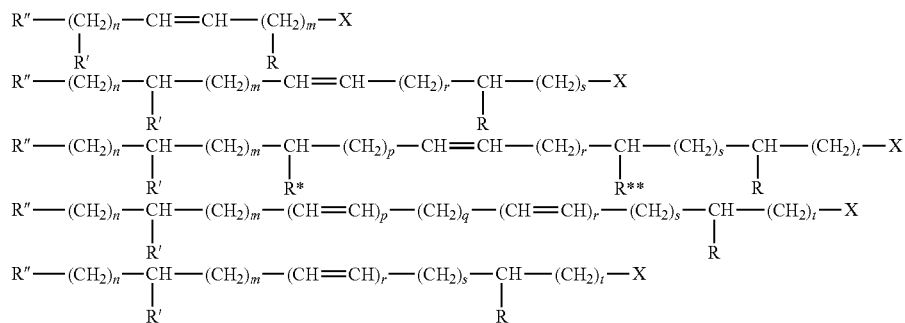

wherein
R, R', R", R* and R** are independently of each other alkyl, alkenyl, alkinyl, heteroalkyl, cycloalkyl, heterocyclyl groups having 1 to 20 carbon atoms, aryl, arylalkyl, alkylaryl, heteroaryl groups having 3 to 20 carbon atoms or functional groups and preferably represent the following groups: —H, —OH, —$OCH_3$, —$OC_2H_5$, —$OC_3H_7$, —O-cyclo-$C_3H_5$, —OCH($CH_3$)$_2$, —OC($CH_3$)$_3$, —$OC_4H_9$, —OPh, —$OCH_2$-Ph, —$OCPh_3$, —SH, —$SCH_3$, —$SC_2H_5$, —$NO_2$, —F, —Cl, —Br, —I, —CN, —OCN, —NCO, —SCN, —NCS, —CHO, —$COCH_3$, —$COC_2H_5$, —$COC_3H_7$, —CO-cyclo-$C_3H_5$, —COCH($CH_3$)$_2$, —COC($CH_3$)$_3$, —COOH, —$COOCH_3$, —$COOC_2H_5$, —$COOC_3H_7$, —COO-cyclo-$C_3H_5$, The term "alkyl" for example in —CO—O-alkyl is preferably one of the alkyl groups mentioned for the aforesaid groups R, R' etc., such as —$CH_2$—Ph. The compounds of the aforesaid general formulas can be present also in the form of their salts as racemates or diastereomeric mixtures, as pure enantiomers or diastereomers as well as mixtures or oligomers or copolymers or block copolymers. Moreover, the aforesaid substances can be used in mixture with other substances such as biostable and biodegradable polymers and especially in mixture with the herein mentioned oils and/or fatty acids. Preferred are such mixtures and individual substances which are suitable for polymerization, especially for autopolymerization.

The substances suitable for polymerization, especially autopolymerization, comprise i.a. oils, fats, lipids, fatty acids as well as fatty acid esters, which are described in more detail below. The lipids are preferably mono- or poly-unsaturated fatty acids and/or mixtures of these unsaturated fatty acids in the form of their tri-glycerides and/or in non-glycerin bound, free form.

Preferably the unsaturated fatty acids are chosen from the group, which comprises oleic acid, eicosapentaenoic, acid, timnodonic acid, docosahexaenoic acid, arachidonic acid, linoleic acid, α-linolenic acid, γ-linolenic acid as well as mixtures of the aforementioned fatty acids. These mixtures comprise especially mixtures of the pure unsaturated compounds.

As oils are preferably used linseed oil, hempseed oil, corn oil, walnut oil, rape oil, soy bean oil, sun flower oil, poppyseed oil, safflower oil, wheat germ oil, thistle oil, grape-seed oil, evening primrose oil, borage oil, black cumin oil, algae oil, fish oil, cod-liver oil and/or mixtures of the aforementioned oils. Especially suitable are mixtures of the pure unsaturated compounds.

Fish oil and cod-liver oil mainly contain eicosapentaenoic acid (EPA C20:5) and docosahexaenoic acid (DHA C22:6) besides of little ☐-linolenic acid (ALA C18:3). All these three fatty acids are omega-3 fatty acids which are required in the organism as an important biochemical constituting substance for numerous cell structures (DHA and EPA), for example, as already mentioned, they are fundamental for the build up and continuance of the cell membrane (sphingolipids, ceramides, gangliosides). Omega-3 fatty acids can be found not only in fish oil, but also in vegetable oils. Further unsaturated fatty acids, such as the omega-6 fatty acids, are present in oils of herbal origin, which here partly constitute a higher proportion than in animal fats. Hence different vegetable oils such as linseed oil, walnut oil, flax oil, evening primrose oil with accordingly high content of essential fatty acids are recommended as especially high-quality and valuable edible oils. Especially linseed oil represents a valuable supplier of omega-3 and omega-6 fatty acids and is known for decades as high-quality edible oil.

As substances participating in the polymerization reaction omega-3 as well as omega-6 fatty acids are preferred as well as all of the substances which have at least one omega-3 and/or omega-6 fatty acid moiety. Such substances demonstrate also a good capability for autopolymerization. The ability of curing, i.e. the ability for autopolymerization, is based in the composition of the oils, also referred to as toweling oils, and goes back to the high content of essential fatty acids, more precisely to the double bonds of the unsaturated fatty acids. When exposed to air by means of oxygen radicals are generated on the double bond sites of the fatty acid molecules, which initiate and propagate the radical polymerization, such that the fatty acids cross-link among themselves under loss of the double bonds. With the clearing of the double bond in the fat molecule the melting point increases and the cross-linking of the fatty acid molecules causes an additional curing. A high molecular resin results, covering the medical surface homogeneously as flexible polymer film.

The auto-polymerization is also referred to as self-polymerization and can be initiated for example by oxygen, especially by aerial oxygen. This auto-polymerization can also be carried out under exclusion of light. Another possibility exists in the initiation of the auto-polymerization by electromagnetic radiation, especially by light. Still another but less preferred variant is represented by the auto-polymerization initiated by chemical decomposition reactions, especially by decomposition reactions of the substances to be polymerized.

The more multiple bonds are present in the fatty acid moiety, the higher is the degree of cross-linking. Thus, the higher the density of multiple bonds is in an alkyl moiety (fatty acid moiety) as well as in one molecule, the smaller is the amount of substances, which participate actively in the polymerization reaction.

The content of substances participating actively in the polymerization reaction in respect to the total amount of all of the substances deposited on the surface of the medical product is at least 25% by weight, preferred 35% by weight, more preferred 45% by weight and especially preferred 55% by weight.

The following table 1 shows a listing of the fatty acid constituents in different oils, which are preferably used in the present invention.

TABLE 1

| Oil species | Oleic acid (C 18:1) omega-9 | Linoleic acid (C 18:2) omega-6 | Linolenic acid (C 18:3) omega-3 | Eicosapentaenoic acid (C 20:5) omega-3 | Docosahexaenoic acid (C 22:6) omega-3 |
|---|---|---|---|---|---|
| Olive oil | 70 | 10 | 0 | 0 | 0 |
| Corn oil | 30 | 60 | 1 | 0 | 0 |
| Linseed oil | 20 | 20 | 60 | 0 | 0 |
| Cod-liver oil | 25 | 2 | 1 | 12 | 8 |
| Fish oil | 15 | 2 | 1 | 18 | 12 |

The oils and mixtures of the oils, respectively, used in the coating according to the invention contain an amount of unsaturated fatty acids of at least 40% by weight, preferred an amount of 50% by weight, more preferred an amount of 60% by weight, further preferred an amount of 70% by weight and especially preferred an amount of 75% by weight of unsaturated fatty acids. Should commercially available oils, fats or waxes be used which contain a lower amount of compounds with at least one multiple bond than 40% by weight, unsaturated compounds can be added in such a quantity that the amount of unsaturated compounds increases to over 40% by weight. In the case of an amount of less than 40% by weight the polymerization rate decreases too much so that homogeneous coatings cannot be guaranteed anymore.

The property to polymerize empowers especially lipids with high amounts of poly-unsaturated fatty acids as excellent substances for the present invention.

So the linoleic acid (octadecadienoic acid) has two double bonds and the linolenic acid (octadecatrienoic acid) has three double bonds. Eicosapentaenoic acid (EPA C20:5) has five double bonds and docosahexaenoic acid (DHA C22:6) has six double bonds in one molecule. With the number of double bonds also the readiness for polymerization increases. These properties of unsaturated fatty acids and of their mixtures as well as their tendency for auto-polymerization can be used for the biocompatible and flexible coating of medical surfaces, especially of stents with e.g. fish oil, cod-liver oil or linseed oil (see examples 13-18).

Linoleic acid is also referred to as cis-9, cis-12-octadecadienoic acid (chemical nomenclature) or as ☐9,12-octadecadienoic acid or as octadecadienoic acid (18:2) and octadecadienoic acid 18:2 (n-6), respectively, (biochemical and physiological nomenclature, respectively). In the case of octadecadienoic acid 18:2 (n-6) n represents the number of carbon atoms and the number "6" indicates the position of the final double bond. Thus, 18:2 (n-6) is a fatty acid with 18 carbon atoms, two double bonds and with a distance of 6 carbon atoms from the final double bond to the external methyl group.

For the present invention the following unsaturated fatty acids are preferably used as substances, which participate in the polymerization reaction and substances, respectively, which contain these fatty acids, or substances, which contain the alkyl moiety of these fatty acids, i.e. without the carboxylate group (—COOH).

TABLE 1

Monoolefinic fatty acids

| Systematic name | Trivial name | Short form |
|---|---|---|
| cis-9-tetradecenoic acid | myristoleic acid | 14:1(n-5) |
| cis-9-hexadecenoic acid | palmitoleic acid | 16:1(n-7) |
| cis-6-octadecenoic acid | petroselinic acid | 18:1(n-12) |
| cis-9-octadecenoic acid | oleic acid | 18:1(n-9) |
| cis-11-octadecenoic acid | vaccenic acid | 18:1(n-7) |
| cis-9-eicosenoic acid | gadoleinic acid | 20:1(n-11) |
| cis-11-eicosenoic acid | gondoinic acid | 20:1(n-9) |
| cis-13-docosenoic acid | erucinic acid | 22:1(n-9) |
| cis-15-tetracosenoic acid | nervonic acid | 24:1(n-9) |
| t9-octadecenoic acid | elaidinic acid | |
| t11-octadecenoic acid | t-vaccenic acid | |
| t3-hexadecenoic acid | | trans-16:1 (n-13) |

TABLE 2

Poly-unsaturated fatty acids

| Systematic name | Trivial name | Short form |
|---|---|---|
| 9,12-octadecadienoic acid | linoleic acid | 18:2(n-6) |
| 6,9,12-octadecatrienoic acid | γ-linolenic acid | 18:3(n-6) |
| 8,11,14-eicosatrienoic acid | dihomo-γ-linolenic acid | 20:3(n-6) |
| 5,8,11,14-eicosatetraenoic acid | arachidonic acid | 20:4(n-6) |
| 7,10,13,16-docosatetraenoic acid | — | 22:4(n-6) |
| 4,7,10,13,16-docosapentaenoic acid | — | 22:5(n-6) |
| 9,12,15-octadecatrienoic acid | α-linolenic acid | 18:3(n-3) |
| 6,9,12,15-octadecatetraenoic acid | stearidonic acid | 18:4(n-3) |
| 8,11,14,17-eicosatetraenoic acid | — | 20:4(n-3) |
| 5,8,11,14,17-eicosapentaenoic acid | EPA | 20:5(n-3) |
| 7,10,13,16,19-docosapentaenoic acid | DPA | 22:5(n-3) |
| 4,7,10,13,16,19-docosahexaenoic acid | DHA | 22:6(n-3) |
| 5,8,11-eicosatrienoic acid | meadic acid | 20:3(n-9) |
| 9c,11t,13t-eleostearinoic acid | | |
| 8t,10t,12c-calendinoic acid | | |
| 9c,11t,13c-catalpicoic acid | | |
| 4,7,9,11,13,16,19-docosahepta-decanoic acid | stellaheptaenic acid | |
| | taxolic acid | all-cis-5,9-18:2 |
| | pinolenic acid | all-cis-5,9,12-18:3 |
| | sciadonic acid | all-cis-5,11,14-20:3 |

TABLE 3

Acetylenic fatty acids

| Systematic name | Trivial name |
|---|---|
| 6-octadecynoic acid | tariinic acid |
| t11-octadecen-9-ynoic acid | santalbinic or ximeninic acid |
| 9-octadecynoic acid | stearolinic acid |
| 6-octadecen-9-ynoic acid | 6,9-octadeceninic acid |
| t10-heptadecen-8-ynoic acid | pyrulinic acid |
| 9-octadecen-12-ynoic acid | crepenynic acid |
| t7,t11-octadecadiene-9-ynoic acid | heisterinic acid |
| t8,t10-octadecadiene-12-ynoic acid | — |
| 5,8,11,14-eicosatetraynoic acid | ETYA |

After accomplishing the described polymerization of the substances containing one linear or branched and one substituted or non-substituted alkyl moiety with at least one multiple bond a surface of a medical product is obtained which is at least partially provided with a polymer layer. In the ideal case a homogeneous continuously thick polymer layer is formed on the total external surface of the stent or a catheter balloon with or without a crimped stent. This polymer layer on the surface of the stent or the catheter balloon with or without stent consists of the substances participating in the polymerization reaction and includes the substances in the polymer matrix participating not actively in the polymerization reaction and/or active agents and/or rapamycin. Preferably the inclusion is adapted to allow the substances not participating in the polymerization, especially rapamycin and additional active agents, to diffuse out from the polymer matrix.

The biocompatible coating of the polymerized substances provides for the necessary blood compatibility of the stent or catheter balloon with or without stent and represents at the same time a suitable carrier for an active agent such as paclitaxel and rapamycin. An added active agent (or active agent combination), which is homogeneously distributed over the total surface of the stent and/or catheter balloon effects that the population of the surface with cells, especially with smooth muscle and endothelial cells, takes place in a controlled way. Thus, rapid population and overgrowth with cells on the stent surface does not occur, which could result in restenosis. However, the population with cells on the stent surface is not completely prevented by a high concentration of a medicament, which would entail the danger of thrombosis. This combination of both effects awards the ability to the surface of a medical product according to the invention, especially to the surface of a stent, to grow rapidly into the vessel wall, and reduces both the risk of restenosis and of thrombosis. The release of the active agent or of the active agents spans over a period of 1 to 12 months, preferably 1 to 2 months after implantation.

A conventional catheter balloon is preferably coated in a first step with a lubricant as e.g. graphite or a stearate and subsequently coated preferably through spray coating with a viscid mixture of an oil or fat and an active agent as e.g. rapamycin or paclitaxel. If necessary, subsequently less curing through auto-polymerization initiated by oxygen molecules or by radiation and/or radical former can occur. Thus a smooth surface results on the surface of the catheter balloon which in general doesn't require a further protection from premature detachment. The catheter balloon in its present form can be pushed forward to the stenotic section of the vessel, and there the transfer of the coating onto the vascular wall can take place by dilating the balloon, wherein the lubricant supports the detachment of the oily coating directly on the surface of the balloon.

Liposomal Formulations

Further preferred embodiments of the present invention relate to liposomal formulations of active agents for the coating of catheter balloons with or without stents.

The liposomal formulations are preferably produced by solving in a first step the active agent (e.g. paclitaxel or rapamycin) or the combination of active agents in an aqueous medium or buffer medium and subsequently contacting them with solutions containing membrane-forming substances. This method yields high inclusion rates of at least 30% up to 95%.

Membrane-forming substances are loaded amphiphilic compounds, preferably alkylcarbonic acids, alkylsulfonic acids, alkylamines, alkylammonium salts, phosphoric acid alcohol esters, naturally occurring and synthetic lipids such as phosphatidylglycerol (PG), phosphatidylserine (PS), derivatives of phophatidylethanolamines (PE derivatives) and those of cholesterol, phosphatidic acid, phosphatidyl inositol, cardiolipin, sphingomyelin, ceramide in its natural, half-synthetic or synthetic forms, stearylamine and stearinic acid, palmitoyl-D-glucuronide and/or loaded sphingolipids as e.g. sulfatide.

Neutral membrane-forming substances are known components as e.g. phosphatidylcholine (PC), phophatidylethanolamine (PE), steroids, preferably cholesterol, complex lipids and/or neutral sphingolipids.

The extraction of liposomes from an aqueous solution is achieved also by using known techniques as e.g. dialysis, ultrafiltration, gel filtration, sedimentation or flotation. The liposomes have a mean diameter of 10 to 400 nm.

Preferably, such liposomal formulations can also be applied into the folds of a fold balloon.

Coating Containing Magnetic Particles

A further coating of catheter balloons according to the invention includes magnetic and/or endocytosis-enabled particles, preferably with a mean particle diameter in the nano-to micro-range, as disclosed e.g. in DE 197 26 282 A.

It is known that nanoparticles can be incorporated from cells via endocytosis. A method for producing such cell-permeable nanoparticles is named in DE 197 26 282.1. The uptake of the nanoparticles can be investigated in in vitro studies in highly purified cell material. In DE 199 12 798 C1 methods are listed by means of which any cell from a tissue can be taken into culture. These methods allow for chemically designing the particles in such a way that a high uptake rate occurs in certain cell types. Thus in DE 100 59 151 A. a coupling of substances such as paclitaxel and rapamycin, for example, to the particles is pursued through ionic interactions wherein the conjugate is enriched in tissue, For the magnetic particles a coating may preferably consist of monomeric aminosilanes as e.g. 3-aminopropyltriethoxysilane, 2-aminoethyl-3-aminopropyltrimethoxysilane, trimethoxysilylpropyldiethylentriamine or N-(6-aminohxyl)-3-aminopropyltrimethoxysilane, which are poly-condensed according to well-known procedures to reach the required stability. For example, a suitable method is described in DE 196 14 136 A or DE 195 15 820 A, It is known further that such magnetic particles can be enriched locally by means of an externally applied magnetic field (DE 109 59 151 A), or that the targeting properties can be enhanced chemically, foe example by coupling with antibodies (DE 44 28 851 A1, EP 0516252 A2). Multi-shell particles for bringing conjugates of particles and active agents into cells, especially tumor cells, are described in patent application WO 98/58673 A. Furthermore, by applying an external alternating magnetic field also a heating of the particles can be achieved, e.g. through hysteresis heat, on 45° C. and more, for example.

The nanoparticles themselves consist of a magnetic material, preferably a ferromagnetic, anti-ferromagnetic, ferrimagnetic, antiferrimagnetic or superparamagnetic material, particularly of superparamagnetic iron oxides or of pure iron, provided with an oxide layer. Preferably, the nanoparticles consist of iron oxides and particularly of magnetite ($Fe_3O_4$), maghemite ($\Box$-$Fe_2O_3$) or mixtures of both oxides. In general the preferred nanoparticles can be described with the formula $FeO_x$, wherein x is a number from 1 to 2. The nanoparticles preferably have a diameter of less than 500 nm. Preferably, the nanoparticles have a mean diameter of 15 nm, or are preferably in the range from 1-100 nm, and particularly preferably in the range from 10-20 nm.

Besides magnetic materials of the formula $FeO_x$, wherein x is a number from 1.0 to 2.0 also materials of the general formula $M(II)Fe_2O_4$ can be used according to the invention, wherein M=Co, Ni, Mn, Zn, Cu, Cd, Ba or other ferrites. The content of metal atoms different from iron atoms is preferably not more than 70% of metal atom, particularly not more than 35% of metal atoms. Preferably, however, the nanoparticles consist of iron oxide to more than 98 weight percent, containing Fe(III) as well as Fe(II) in a ratio of preferably 1:1 to 1:3. Moreover, also silica and polymeric particles are suitable in which magnetic materials as for example the magnetic materials listed herein are embedded and/or bonded.

The used nanoparticle cores may also consist of non-magnetic materials. They can be eligible from for example polymeric nanoparticles (e.g. PLGA, polyacrylamide, polybutylcyanoacrylate), metals as well as from all oxide materials (e.g. MgO, CaO, $TiO_2$, $ZrO_2$, $SiO_2$, $Al_2O_3$). According to the invention, any material is suitable that can be coated with tumor-specific shells by the aforementioned methods, since the ability for endocytosis doesn't depend from the particle but from the shell.

To these nanoparticles therapeutically active substances can be bound, wherein a covalent binding as well as adsorptive and ionic bindings are possible.

According to the invention, the inducible conjugates of nanoparticles and active agent are preferably based on magnetic iron-containing cores surrounded by one or more colloidal shells or coatings optionally to be coupled with active agents via functional groups. Herein, the core consists of magnetite or maghemite. The primary role of the shells is to attain a colloidal distribution in aqueous medium and to protect the nanoparticles from agglomeration. Multi-shell particles, as described in patent application WO 98/58673, are in principle suitable as a basis for inducible conjugates of nanoparticles and active agents, since the biological behaviour of such particles can be adjusted by the coatings with polymers and a coupling of the active agents to functional groups of the primary shell is possible.

A further coating of inducible conjugates of nanoparticles and active agents (e.g. with polymers), as described in WO 98/58673, is possible also and can be used for improving the biological properties of the conjugates of nanoparticles and active agents.

According to the invention catheter balloons are thus provides with a coating containing magnetic and/or endocytosis-enabled particles. Additionally, the coating can comprise preferably one or more polymers, wherein the magnetic and/ or endocytosis-enabled particle can be embedded together with the active agent such as paclitaxel or rapamycin or the combination of active agents. Moreover, it is also possible to apply a mixture of a contrast medium or contrast medium analogue together with an active agent and the magnetic and/or endocytosis-enabled particles on the surface of the balloon with or without a crimped stent. Furthermore, a solution or a dispersion of magnetic and/or endocytosis-enabled particles and the active agent in a preferably light volatile solvent such as acetone, methanol, ethanol, tetrahydrofuran (THF), methylene chloride, chloroform, ether, petrol ether, acetic acid ethyl and methyl ester, cyclohexane, hexane and other organic solvents with boiling points below 100° C. can be produced which subsequently is applied onto catheter balloons with or without a crimped stent, preferably by spray method.

As mentioned before, the active agent can be bound adhesively or also covalently to the outer shell of the magnetic and/or endocytosis-enabled particles, or the magnetic and/or endocytosis-enabled particles are enclosed together with an active agent or a composition of active agents (e.g. rapamycin and/or paclitaxel) into microcapsules or liposomal formulations and applied in this form on the surface of the balloon.

Such coatings of active agent and magnetic and/or endocytosis-enabled particles can be coated, of course, with another protective as well as a release-controlling layer.

Particularly suitable as outer shells for the coating of catheter balloons are layers or coatings with a crisp bursting during dilation providing a particular good lubrication to the balloon and displaying only few interactions respectively sliding friction with the vascular wall.

In a particularly preferred embodiment comprising the coating with magnetic and/or endocytosis-enabled particles the particles, respectively the coating containing these particles, are fixed on the surface of the balloon by means of an external magnetic field. In another embodiment a magnet with reversible polarity as e.g. an electromagnet is arranged inside the catheter balloon or in its outer layer which attracts the oppositely polarized particles during the placement of the catheter and thus binds them firmly to the surface of the balloon. On dilation of the balloon the magnet inside the balloon is reversed in its polarity and repulses the particles with the same polarity, respectively the equally polarized particles, thus pressing the magnetic particles into the vascular wall and the single cells, especially smooth muscle cells.

This embodiment ensures a firm adhesion of the magnetic particles during the placement of the catheter balloon on the basis of magnetism, either through an external local magnetic field or preferably through a magnetic field generated inside the catheter balloon, and additionally leads to a quantitative repulsion of the magnetic particles and transfer into the adjacent tissue on expanding the catheter balloon.

In this method very short dilation times of the catheter balloon of less than 30 seconds are sufficient, preferably 5-20 seconds, more preferably 5-10 seconds and particularly preferably 3-6 seconds.

As the active agent or the active agents are firmly connected to the surface of the magnetic particles, by means of adsorption or by means of a covalent bond possibly also via a linker, or by embedding into a superficial coating of the magnetic cores of the particles, the loss in active agent during the placement of the catheter is equally very low.

Furthermore, the magnetic particles can be provided with a coating having a particularly high affinity to smooth muscle cells and a lower affinity to endothelial cells, so that it can be controlled through the coating of the magnetic micro- or nanoparticles that preferably smooth muscle cells are killed or inhibited in their proliferation while endothelial cells are mostly spared, something very positive in the prophylaxis and treatment of restenosis. Moreover, it can be controlled through the amount of the applied active agent whether e.g. paclitaxel exerts rather cytotoxic or cytostatic actions.

Since the active agents are firmly, but in general not irreversibly bound to the magnetic particles the active agents are incorporated together with the magnetic particles into the cells, preferably smooth muscle cells, and exert their actions inside the cell, thus leading to a significantly enhanced effect of the active agent.

Hydrogel

In another embodiment according to the invention a hydrogel is applied onto the catheter balloon with or without a stent, containing at least one of the aforementioned active agents, preferably paclitaxel or rapamycin, or their derivatives.

Preferably such a hydrogel coating is protected from the contact with blood through an overcoat as used in self-expanding Nitinol stents for such a time until the catheter balloon is placed at the stenotic section of the vessel. There the protective overcoat is removed and the hydrogel starts bulging when contacted with blood. The expansion of the catheter balloon transfers the major part of the hydrogel layer onto the vascular wall and remains there as a short-term pool of active agent, continuously releasing the active agent, e.g. paclitaxel or rapamycin, to the vascular wall until the hydrogel layer is dissolved during a few days or weeks.

Salts with an Active Agent

A particularly preferred embodiment of the present invention is a coating of the catheter balloon preferably without a stent with a solution or dispersion of an active agent, preferably paclitaxel or rapamycin or their derivatives, and particularly paclitaxel, together with one or more physiologically acceptable salts.

As salts compounds containing sodium cations, calcium, magnesium, zinc, iron or lithium cations together with sulfate, chloride, bromide, iodide, phosphate, nitrate, citrate or acetate anions can be used.

The active agent or the combination of active agents is added to this solution, dispersion or suspension. Preferably water serves as a solvent, possibly also with co-solvents. The salt concentration should be relatively high.

The catheter balloon is coated via a dipping or a spraying method, or brush or squirting method with this salt solution containing an active agent and subsequently dried so that a firm salt crust results on the catheter balloon. Moreover, also ionic contrast media can be used as salts, or ionic contrast media can be added to the aforementioned salts.

The goal is to generate on the catheter balloon a mostly homogenous coating of a solid, i.e. a salt, in which the active agent is enclosed. This salt crust is then provided either with a protective cover layer or a removable wrapper, as it is used in self-expanding stents, in order to protect them from premature detachment. A third variant consists in using a fold balloon and applying this salt mixture specifically under the folds of the catheter balloon.

The salt coating is very hygroscopic and thus has a high affinity to the vascular tissue. On dilation the wrapper is removed or the outer protective barrier layer bursts or, when using a fold balloon, the folds unfold and press the salty coating against the vascular wall.

Then the salt coating downright sticks to the vascular wall where it fulfils several tasks. On the one hand the locally very high salt concentration leads to a high isotonic pressure which makes cells burst, and on the other hand the high salt concentration dissolves also hard plaques and other sedimentations in the vessel and additionally releases the active agent which particularly suppresses the proliferation of smooth muscle cells.

After a few hours up to some days, according to the amount, the salt coating transferred onto the vascular wall is completely dissolved.

Coating Methods

Furthermore the present invention is directed to methods for coating catheter balloons with or without a crimped stent.

The short-term implant is either completely or partially coated with a solution of the substances to be applied including the active agent or combination of active agents by a spraying, dipping, brushing, squirting, roll, drag, pipetting or electro-spinning method, or completely or partially coated with a matrix.

As solvents volatile organic compounds such as dichloromethane, chloroform, ethanol, acetone, heptane, n-hexane, DMF, DMSO, methanol, propanol, tetrahydrofuran (THF), methylenechloride, ether, benzine, acetonitrile, acetic acid ethyl and methyl ester, cyclohexane and corresponding mixtures thereof can be used. According to the coating material (e.g. hydrogels or water-soluble active agents) also the presence of water may be desirable.

When choosing the solvent it is in general of utmost importance that the material of the short-term implant is not dissolved or rendered useless, or the exposure time is so short that no damages can occur.

The matrix consists of a synthetic, semi-synthetic or natural, biostable or biodegradable, biocompatible polymer or polymer mixture, prepolymers, polymerizable substances such as unsaturated fatty acids, micelle or liposome-building substances encapsulating active agents, which should meet the requirements of the implant. Suitable polymers are mentioned above. Thereby an additional depot effect and dose enhancement can be achieved.

The catheter balloon can be coated either in the expanded or in the folded state, coated partially or completely, or coated together with a mounted stent. The coating can be done by a spraying, dipping, brushing, squirting, drag, roll and/or pipetting method. The pipetting, dragging, rolling or squirting methods are particularly suitable for the use in folded catheter balloons or fold balloons as with these methods the solution with the active agent or with the combination of active agents can be specifically applied into or under the folds. It is important thereby that no impairment in functionality occurs by this partial coating. For example, the folds may not stick together when being expanded and thus counteract the expansion. Likewise the nominal pressure on the balloon shouldn't be increased beyond the maximum value in order to counteract adhesive forces of the coating in the folds. Uneven expansion should be avoided also. The coating shall in no case impair the expansion characteristics of the balloon catheter.

Furthermore the catheter balloon can be coated together with a crimped stent, or a bare stent as well as an already coated stent can be crimped onto the coated catheter balloon thus achieving a system of for example an active agent rapidly released from the catheter balloon and an active agent slowly released from the coating of the stent.

In combination with a stent coated on his part and able to release an active agent a substance-releasing balloon catheter is particularly advantageous in the early phase of the healing process, as only that way the complete contact with the sector to be treated can be realized and the active agent enters the affected vascular wall in its entire dimension. The whole affected sector is provided with active agent when being exposed to the surface of the balloon catheter while the stent with a preferably small surface covers only a small portion of the surface of the vascular wall.

Equal advantages should be given for the marginal zones of the stent which continuously cause problems. A catheter balloon capable of releasing an active agent also in the marginal zones delivers an optimal provision for the vessel even in the problem zones of the stent.

The salt solutions and the compositions containing contrast medium or also the compositions of salts and contrast media are particularly suitable for coating fold balloons or catheter balloons with a rough, napped, porous or micro-structured surface, or to bring these mixtures into or under the folds of the fold balloons.

The catheter balloons with a special surface are preferably coated with the spraying or pipetting method. In the spraying method the catheter balloon is suspended in a revolving manner and the form of the catheter balloon is stabilized by a light vacuum. For example the folds of a fold balloon can be prevented from flipping or skidding and thus from performing the coating not specifically local.

The balloon catheter thus tethered is several times briefly sprayed while drying intermittently. If desired, the outer protective layer or barrier layer is also preferably applied by spraying. The same applies for the layers containing only an active agent such as paclitaxel or rapamycin which are also applied preferably by spraying.

The pipetting method is particularly suitable for the coating of a balloon catheter. Herein the revolvably tethered balloon catheter (with or without a stent) is coated by means of a fine nozzle prolonged with capillaries through which the coating solution passes out lengthwise the balloon catheter.

In the squirting or pipetting method a fine nozzle or cannula is moved under the folds for preferably filling the folds of a fold balloon, and the solution to be applied is squirted into the fold wherein the nozzle or cannula is preferably moved along the fold or, when the nozzle or cannula is stationary the fold balloon is moved lengthwise the fold. This method allows for a very precise and exact coating of each single fold, respectively of the whole balloon. A possibly used solvent evaporates or is removed under vacuum.

If the consistency of the mixture or solution to be applied allows for flowing into the folds the fold balloon is positioned horizontally with one fold upside, or preferentially inclined by 5 to 25 degrees, so that the syringe or nozzle can be set at the lower end of the fold balloon at the aperture of the fold and the mixture can flow on its own into the fold and fill it completely.

In these salt solutions preferably water is used as a solvent because water doesn't pit and damage the balloon material. Once the mixture has a consistency that it can't flow anymore out of the fold the fold balloon is turned and the next fold is filled until all, in general 4 to 6, folds of the balloon are filled. Fold balloons are preferably coated in the packed state, but some special embodiments of fold balloons can also be coated when being expanded.

Such a coating method comprises the steps
a) providing a fold balloon,
b) placing a fold of the balloon into a horizontal position or inclined up to 25 degrees,
c) setting the aperture of the syringe at the aperture of the fold which faces the top of the balloon,
d) making a relative movement of the aperture of the syringe and the fold balloon lengthwise the fold
e) filling the fold during the movement with a mixture of an active agent and a salt and/or a ionic contrast medium in a suitable solvent, f) if necessary, drying of the mixture inside the fold to such a degree that no leaking out of the mixture can occur, g) turning the balloon by 360° divided by the number of folds h) repeating steps b) to g) until all folds are filled, and i) drying of the mixtures inside the folds until the mixture hardens.

If more fluid solutions are used the aperture of the syringe is set in step c) at the bottom end and the fold is filled without a relative movement according to step d) mainly because of capillary forces.

The present invention is further directed to a method of keeping open stenotic vessel lumina, especially of cardiovascular vessels by means of short-term dilation. In this method a catheter balloon without a stent is expanded during maximally 50 seconds, preferably maximally 40 seconds, more preferably maximally 30 seconds and most preferably maximally 20 seconds and then repacked to a diameter less than the 1.5 fold initial diameter wherein the vessel is only overstretched by maximally 10% of its diameter in the non-stenotic state and at least 20% of the contained active agent per mm$^2$ surface of the balloon is released and mostly transferred onto the vascular wall.

Herein the transfer of the active agent does preferably not occur in its pure form but in a matrix which is active as a store for the active agent for at least one hour after dilation and releases further active agent to the vascular wall before being dissolved or degraded.

This method thus is characterized in transferring a preferably large amount of active agent locally and specifically onto the vascular wall of a stenotic section of a vessel during a preferably short time and in providing a local store of active agent during the ensuing 30 to 60 minutes up to maximally 3 days, then being dissolved or degraded.

In this method especially active agents combining anti-inflammatory and antiproliferative properties have been shown to be particularly suitable (see list of active agents p. 7-10). Among them are for example colchicine, angiopeptin, but above all rapamycin and its derivatives, furthermore other hydrophobic active agents, particularly paclitaxel and paclitaxel derivatives have been shown to be very suitable.

Another method according to the invention is directed to the coating of catheter balloons with oily polymerizable substances. This method comprises the steps:

a) providing a catheter balloon, b) providing a mixture consisting of at least 50% weight percentage of oily substances with at least one multiple bond and containing at least one active agent, c) applying a lubricant on the surface of the catheter balloon mostly preventing the adhesion of the oily substances on the surface of the catheter balloon, d) applying the oily mixture on the lubricant or the lubricant layer on the catheter balloon, e) rotating the catheter balloon during coating step d), f) initializing the polymerization by means of light, oxygen or radical starters until obtaining a non-hard but elastic polymeric layer, g) possibly repeating coating steps d) to f).

The fold coating or fold filling methods according to the invention are the pipetting method, also named capillary method, the squirting method and the spray method, also named fold spray method, in order to clarify the difference to the unselective spray method for the entire catheter balloon.

Thus the present invention relates to methods for coating or filling folds of a catheter fold balloon in which a) a composition containing an active agent is released at the distal or the proximal end of a fold of the catheter fold balloon and the folds are filled by capillary forces; or b) a syringe continuously releasing a continuous flow of a composition containing an active agent is moved lengthwise a fold relative to the catheter fold balloon; or c) a plurality of aligned release apertures is moved under the folds of a fold balloon and a composition containing an active agent is released concomitantly from the plurality of release apertures into the fold.

It is of advantage that this coating or filling method can be carried out preferably in the packed or deflated or maximally 10% inflated state of the catheter balloon. The term "10% inflated state" means that the catheter balloon has undergone a 10% inflation respectively expansion of the maximal expansion planned during dilation. If the expansion planned during dilation is referred to as 100% and the deflated state is set to 0% a 10% inflation results from the following formula:

$$\text{(diameter of the deflated catheter balloon)} + \text{(diameter of the inflated catheter balloon} - \text{diameter of the deflated catheter balloon)}/10$$

Furthermore, several or all folds can be coated or filled concomitantly according to the methods of the invention, or the coating and filling can be specific. A specific filling or coating of the folds means that only the folds are filled or coated and the surface of the catheter balloon outside the folds will not be coated.

A preferably used composition of active agent, solvent and matrix such as contrast medium has the consistency of a paste, gel of a viscous mass or a viscous dispersion or emulsion or a tough pap.

This composition has the advantage that it does not polymerize and maintains its consistency during the coating. This paste or (high) viscous mass or thick suspension is applied under pressure into the folds with a squirting device, preferably a nozzle as shown in FIG. 1.

If necessary, the nozzle can widen the folds of the balloon and specifically fill the cavities formed by the folds. Fold balloons usually have 4 or more folds which will be filled one after the other.

It showed to be particularly advantageous to rotate the fold balloon in the direction of the apertures of the folds after one or more or all folds have been filled. This rotation leads to a complete and even distribution of the viscous paste in the folds and to a release of possible air locks. After rotating the fold balloon a further filling of already filled or empty folds can be done.

During or after rotation the composition in the folds dries under atmospheric or slightly diminished pressure. The drying or hardening of the composition occurs by removing the at least one alcohol by evaporation. The dried composition has a porous consistency and can very easily be detached from the balloon surface during dilation. Alcohol as a solvent has been removed except for the usual residual and the contrast medium forms a porous matrix for the agent and additionally is capable to release the active agent rapidly and in a high amount after dilating the fold balloon. Moreover, the method according to the invention has the advantage to be very material-sparing since only the folds are coated or filled and thus no active agent is located on the outer surface of the balloon which could get lost during the introduction of the catheter.

General Description of the Coating Methods

Pipetting Method-Capillary Method

This method comprises the following steps:
a) providing a folded packed catheter balloon,
b) providing a coating device with an aperture capable for pointwise release of the coating solution,
c) setting the aperture capable for pointwise release of the coating solution to the proximal or distal end of a fold of the catheter balloon,
d) releasing a defined amount of the coating solution through the outlet at the proximal or distal end of a fold, and
e) filling the fold with the coating solution because of capillary effects.

Optionally, there can be still step f) for drying:
f) drying of the coating solution in the fold wherein the catheter balloon is rotated during drying about its longitudinal axis in direction of the aperture of the folds.

This method coats or fills specifically the folds and can be performed with any coating solution which is still so viscous that it is drawn because of capillary forces or by additionally using gravitation into the fold during 5 minutes, preferably 2 minutes, and thus mostly completely fills the fold.

Squirting Method or Syringe Method:

This method comprises the following steps:
a) providing a folded packed catheter balloon,
b) providing a coating device with at least one nozzle or at least a syringe-shaped outlet,
c) setting the nozzle or the outlet at the proximal or distal end of a fold of the catheter balloon,
d) moving the nozzle or the outlet along the fold relative to the fold, and
e) releasing a flow of coating solution defined in time and covered distance.

Optionally, there can be still step f) for drying:
f) drying of the coating solution in the fold or evenly distributing the coating in the fold wherein the catheter balloon is rotated about its longitudinal axis in direction of the aperture of the folds.

This method coats or fills specifically the folds and can be performed with any coating solution which is still so viscous that it can be filled into the fold by means of small nozzles or small outlets.

Spray Method or Fold Spray Method:

This method comprises the following steps:
a) providing a folded packed catheter balloon,
b) providing a coating device with a plurality of aligned releasing apertures,
c) inserting the plurality of aligned releasing apertures under the fold of a catheter balloon,
d) concomitant release of a defined amount of the coating solution from the releasing apertures into the fold; and
e) drying of the coating solution in the fold.

Optionally, there can be still step f) for drying:
f) drying of the coating solution in the fold or evenly distributing the coating in the fold wherein the catheter balloon is rotated about its longitudinal axis in direction of the aperture of the folds.

This method coats or fills specifically the folds and can be performed with any coating solution which is still so viscous that it can be filled into the fold by means of small nozzles or small outlets.

Drag Method or Drop-Drag Method:

This method comprises the following steps:
a) providing a catheter balloon in a folded, partially inflated or completely inflated state,
b) providing a coating device with a dispensing device,
c) forming of a drop of the coating solution at the dispensing device,
d) dragging the drop over the surface of the catheter balloon to be coated without the dispensing device itself contacting the surface of the catheter balloon, and
e) redosing of the coating solution so that the drop substantially maintains its size.

This elegant and for the catheter balloon particularly careful method uses a drop of the coating solution to be moved or dragged over the surface of the balloon without the dispensing device contacting the surface of the balloon and thus the drop as well as the surface of the balloon moving relatively to one another.

The coating solution is redosed in such a way that the drop substantially maintains its size as well as the connection of the dispensing device and the surface of the balloon. By means of a volume measuring device the dispensed amount of coating solution can be exactly determined after the coating and thus the amount of active agent on the balloon.

Thread Drag Method:

This method comprises the following steps:
a) providing a catheter balloon in a folded, partially inflated or completely inflated state,
b) providing a coating device with a dispensing device in form of a thread, sponge, leather strip or piece of textile,
c) providing a coating solution,
d) soaking the dispensing device with the coating solution,
e) transferring the coating solution from the dispensing device onto the surface of the catheter balloon to be coated, and
f) redosing of the coating solution so that a consistent dispense of the coating solution from the dispensing device onto the surface of the catheter balloon to be coated occurs.

This likewise very elegant method is also very smooth to the surface of the catheter balloon since the dispensing device contacts the surface of the balloon but is shaped in such a way that it can't damage the surface the balloon. The dispensing device is dragged or pulled over the surface of the balloon by a movement of the catheter balloon relative to the dispensing device and thereby releases a defined amount of the coating solution. By means of a volume measuring device the dispensed amount of coating solution transferred onto the balloon can be exactly determined after the coating, thus yielding the exact amount of active agent on the surface of the balloon.

Ballpoint Method or Roll Method:

This method comprises the following steps:
a) providing a coating device with a ballpoint for transferring the coating solution onto the surface of the catheter balloon to be coated,
b) providing a coating solution with access to the ballpoint,
c) setting the ballpoint of the coating device onto the surface of the catheter balloon to be coated,
d) exerting a pressure on the ballpoint of the coating device for enabling the outflow of the coating solution, and
e) tracing the surface of the catheter balloon to be coated with the ballpoint thus transferring the coating solution onto the surface of the catheter balloon to be coated.

In this likewise quite elegant method the dispensing device rolls over the surface of the balloon by a movement of the catheter balloon relative to the dispensing device and thereby releases by means of a ballpoint an amount of the coating solution onto the surface of the balloon which can be determined with a volume measuring device.

In the following the coating and filling methods are addressed in more detail.

Pipetting Method or Capillary Method:

In this method a pipette or a syringe or any other device capable of releasing pointwise the composition containing the active agent is used.

The terms "composition containing the active agent" or "coating solution" as used herein relate to a mixture of active agent and solvent and/or excipients and/or carrier, thus a real solution, dispersion, suspension or emulsion of an active agent or combination of active agents and at least one component, to be chosen from the solvents, oils, fatty acids, fatty acid esters, amino acids, vitamins, contrast media, salts and/or membrane-building substances listed herein. The term "solution" shall further mean that it is a fluid mixture which, however, can also be gel-like, viscous or pasty (thick viscous or high viscous).

The pipette or syringe or outlet or other device capable for pointwise release of the composition containing the active agent is filled with the composition and its outlet is set preferably to the proximal or distal end of a fold. The escaping composition is drawn from capillary forces into the fold and along the fold until the opposite end of the fold is reached'

The catheter balloon is packed, i.e. deflated. Even a partial or marginal inflation of the catheter balloon is usually not needed to open the folds slightly. Nevertheless the filling of the folds can be carried out with a marginal inflation of the catheter balloon up to maximally 10% of the diameter provided for dilation. On filling the folds there can be also a slight widening of the folds by applying 100 kPa (1 bar) overpressure, preferably 50 kPa (0.5 bar) for widening the folds slightly.

In this method it is important that the composition containing the active agent is sufficiently fluid for the capillary forces to develop.

As compositions particularly solutions of an active agent or a composition of active agents in an alcohol or in a mixture of alcohols are preferred.

The capillary forces should be thus strong that a fold with the length of 10 mm is completely filled during 5 to 80 seconds, preferably during 15 to 60 seconds and particularly preferably during 25 to 45 seconds.

If the composition, respectively solution, too viscous it can be advantageous to incline the catheter balloon with the fold to be filled upwards from the horizontal position to maximally 45°, preferably maximally 30° and thus also using gravitation. In general, the filling of a fold by means of capillary forces occurs, however, in a horizontal position of the catheter balloon with the fold to be filled upside. The pipette or syringe or other device capable for pointwise release of the composition containing the active agent is set onto the fold preferably at the proximal or at the distal end of the fold in a sharp angle in direction of the fold axis in an angle of 10° to 65°, preferably 20° to 55°, more preferably in an angle of 27° to 50° and particularly preferably in an angle of 35° to 45°, measured from the horizontal plane. The filling of the fold is then performed from the upper end of the fold so that the coating solution finds a downhill gradient and additionally to the capillary forces also uses gravitation.

Principally there is also the possibility to set the pipette or syringe or other device capable for pointwise release of the composition containing the active agent to the middle of the folds or to any other point between the distal and the proximal end so that the fold fills itself concomitantly in direction of the proximal and the distal end because of capillary forces, but the starting points at the end of the fold have were found to be preferable.

When the composition for filling the folds respectively the present fold has reached to opposite end the substance flow usually stops by itself and the pipette or syringe or outlet or other device capable for pointwise release of the composition containing the active agent can be removed.

In order to prevent that a larger drop of the composition containing the active agent remains at the setting point of the pipette or syringe or other device capable for pointwise release of the composition containing the active agent it was found to be advantageous to remove the pipette or syringe or other releasing device before the composition containing the active agent reaches completely the other end of the fold. Thereby the remaining composition containing the active agent at the setting point of the pipette or syringe or other releasing device is drawn into the fold so that no coating, or better filling, composition remains outside the fold.

Preferably the pipette or syringe or other releasing device is removed when ca. 90% of the fold is filled with the composition containing the active agent. The optimal moment for removing the pipette or syringe or other releasing device can be determined exactly and reproducibly with a few experiments.

The term "other device capable for pointwise release of the composition containing the active agent" relates to a device which is capable similar to a pipette is capable of providing a steady and continuous flow of the composition containing the active agent so that it can also refer to a pump, micro-pump or another store which ensures this steady and continuous release of the composition containing the active agent.

After the filling of a fold the catheter balloon is rotated so that the next fold to be filled lies upside, and preferentially horizontal. The filling procedure is now repeated.

According to the consistency of the composition containing the active agent it may be necessary to dry the previously filled fold before rotating the balloon for filling the next fold. Drying is preferably achieved by evaporation of the solvent.

Furthermore, this method is also enabled for filling or coating two, more than two or all folds of a catheter balloon at the same time, if the consistency of the composition containing the active agent allows for that, i.e. the consistency is not that fluid that the composition passes out of the folds which are not positioned horizontally.

Particularly the pipetting method is suitable for filling concomitantly several or all folds of a catheter balloon. Herein the catheter balloon can be arranged horizontally or preferably vertically and the releasing devices are set from above to the ends of the folds preferably in an angle of 10 to 70 degrees, so that the composition containing the active agent can flow into the folds.

When all folds of the balloon are filled it comes to final drying. Principally it is not needed that all folds of the catheter balloon are filled, but the filling of all folds is the common and preferred embodiment, since during dilation a preferably maximal amount of active agent shall be transferred onto the vascular wall in a preferably short time.

In the fold balloons according to the invention dilation lasts for preferably maximally 60 seconds and particularly preferably for maximally 30 seconds.

After filling the last fold the last folds are dried, i.e. the content of the last fold is dried preferably without a vacuum under normal pressure by evaporation of the solvent.

To this preliminary drying a final drying can ensue which is carried out according to the invention in rotating catheter balloons. If required or desired, additionally a vacuum can be applied during rotation. This special drying method is described in more detail following the coating methods.

Squirting Method or Syringe Method:

In this method according to the invention a fine syringe, syringe-shaped opening, syringe-shaped outlet or needle or nozzle is set to the proximal or distal end of a fold, and this releasing device in form of a syringe, needle or nozzle is moved along the longitudinal axis of a fold relative to the fold and according to the traced section a certain amount of the composition containing the active agent or a defined flow of the coating solution is released.

Herein it is irrelevant whether the catheter balloon is tethered and the releasing device is moved along the fold, or whether the releasing device is fixed and the catheter balloon moves relatively, or whether both the catheter balloon and the releasing device even move towards one another. If the catheter and the releasing device move relatively towards one another a movement on a straight line in opposite directions is preferred.

From the releasing device, i.e. the syringe, needle or nozzle or the like, a preferably medium to thick viscous composition containing the active agent is released into the inside of the fold preferably in form of a paste or a gel or an oil. Viscosities of preferred solutions range between $10^1$ to $10^6$ mPa·s, preferably between $10^2$ to $10^5$ mPa·s and particularly preferably between $10^3$ to $10^4$ mPa·s.

Thus especially those compositions containing an active-agent along with the above-listed oils, alcohols (especially diols and polyols), fatty acids, fatty acid esters, amino acids, polyamino acids, membrane-building substances, liposomal formulations and/or their salts are suitable.

In the coating procedure the tip of the syringe, needle or nozzle reaches ca. up to the centre of the inside of the fold, thus into the centre of the fold, i.e. the nozzle or the outlet is located relatively central in the cavity formed by the fold. There a continuous flow of the composition containing the active agent occurs in such a way that the velocity and the amount of the release in regard of the relative displacement velocity of the releasing device and the catheter balloon are suitable to fill the fold, respectively the inside of the fold, with the composition containing the active agent by at least 50 volume percent, preferably by at least 70 volume percent and particularly preferably by at least 85 volume percent.

The filling of a fold lasts in a fold length of 10 mm for ca. 5 to 80 seconds, preferably ca. 15 to 60 seconds and particularly preferably ca. 25 to 45 seconds.

During the filling procedure the catheter balloon is packed, i.e. deflated. In general even a partial or marginal inflation of the catheter balloon is not needed for opening the folds slightly. Nevertheless the filling of the folds can be carried out with a marginal inflation of the catheter balloon up to maximally 10% of the diameter provided for dilation. On filling the folds there can be also a slight widening of the folds by applying 100 kPa (1 bar) overpressure, preferably 50 kPa (0.5 bar) for widening the folds slightly.

This coating method can of course also be carried out with fluid compositions containing an active agent, but is rather suitable for oily compositions and high concentrated salt solutions.

Furthermore, this method provides the advantage that more than one fold and particularly all folds can be coated or filled at the same time. Herein a circular array of release devices is disposed according to the number of the folds in such a way that one releasing device per fold is provided. By a slight rotation the tips of the releasing devices are inserted into the folds and placed ca. at the centre of the inside of the folds. By a slight and concomitant movement of the releasing device relative to the longitudinal axis of the folds all folds can be filled at the same time with a continuous and steady flow of the composition containing the active agent.

During the filling or coating of one or all folds the catheter balloon may be positioned vertically, horizontally or obliquely.

If volatile solvents have been used in the composition containing the active agent it may be necessary to dry the content of the folds or to remove the volatile solvent with boiling points under 150° C. In volatile solvents this is preferably done first by evaporation of the one or more volatile solvents.

Then a final drying can occur wherein the catheter balloon is rotated direction of the openings of the folds, seen from the inside of the folds. This method is addressed more in detail further below. If coating solutions were used that remain oily or pasty after removing the possibly present solvent the rotation drying can serve on the one hand for removing the residuals of the solvent with boiling points less than 150° C. and on the other hand for evenly distributing the oily or pasty layers inside the folds.

The turning or rotation of the catheter balloon in direction of the openings of the folds can also serve to evenly distribute the compositions located in or under the folds inside the fold.

This rotation of the fold balloon can be particularly advantageous when using oily or pasty compositions containing an active agent to ensure an even distribution of the composition containing the active agent inside the folds and also on the surface of the folds.

In contrast, the term "filling" rather relates to a complete filling of the inner space of the folds with a composition containing an active agent.

If solvents are used which can be removed by drying in general a filling can't be reached. Thus it is a rather a coating of the inner surfaces of the folds.

If substances with a high boiling point are used instead as carriers or excipients a more or less complete filling of the folds is possible as long as no considerable amount of volatile substances is present in the composition containing an active agent.

This squirting method or syringe method is particularly suitable for the application of compositions containing an active agent into the folds of fold catheter balloons which cannot be applied onto a catheter balloon or even inside the folds by conventional dipping and spraying methods.

In contrast to the conventionally used solid coatings of stents or on catheter balloons these oily and pasty coatings and fillings have the advantage that the compositions containing an active agent don't dry completely but mostly maintain their consistency. Thus coating solutions are used preferably which don't harden completely on air or under protective gas at normal pressure, i.e. after substantially removing a possibly used solvent of the coating solution an oily or pasty coating remains inside the folds of the catheter balloon after the solvent was removed by evaporation or under reduced pressure. Thus coating solutions are preferred which after removing the optionally used solvent have a melting point or solidification point of less than 20° C., preferably less than 30° C. and additionally display a thick viscous, oily or pasty consistency in order that also when storing the coated catheter balloon for several months up to one year the coating doesn't ooze out of the folds.

The use of a removable solvent is, however, not compulsory, so that also physiologically acceptable solvents or a physiologically acceptable component of the coating solution can be used, such as polyethylene glycol, glycerine, propylene glycol or the like, which will not be removed and remains in the coating and keeps the coating in the folds oily and pasty for the shelf life of the coated medical device.

The enormous advantages of such oily and pasty coatings are evident. If the catheter balloon is inflated or dilated at the stenotic place this oily and pasty composition is at least partially, but in general substantially transferred onto the vascular wall and serves as a active agent depot for a delayed release of the active agent to the adjacent tissue for several hours up to days and additionally has the benefit of dissolving plaques, respectively counteracting the sedimentation of plaques, and is biologically degraded itself later on without releasing physiologically critical metabolites. This system perfectly solves the problem to apply on the one hand a coating safely to the catheter balloon for not being washed away by the bloodstream when being introduced or not being transferred when contacting the vascular wall and on the other hand to transfer during dilation a sufficient amount of the active agent onto the vascular wall in a relatively short time, i.e. in 30 to 300 seconds, i.e. as less as possible coating remains on the catheter balloon and as much as possible, i.e. at least 50% of the coating is transferred onto the vascular wall for effectively counteracting restenosis.

Such systems according to the invention cannot only be produced by the squirting method, but also by the other coating methods described herein.

Spray Method or Fold Spray Method

In this method according to the invention a plurality of aligned release apertures is moved or set under the fold of the fold balloon and a composition containing an active agent is released concomitantly from the plurality of apertures into the respective fold.

The release device consists preferably of 2 to 10 nozzles or release apertures which are aligned preferably at equal intervals along the longitudinal direction of the folds.

This release device is then inserted under the fold of the catheter balloon and the respective fold is filled or coated by concomitant release of the composition containing an active agent from the nozzles or other release apertures.

Similar as in the so-called squirting method the filling of a fold lasts ca. 5 to 80 seconds, preferably ca. 15 to 60 seconds and particularly preferably ca. 25 to 45 seconds when having a fold length of 10 mm and using 4 release apertures. The release apertures are preferably located mainly in the centre of the cavity under the folds.

In thus coating or filling variant it isn't necessary to move the release device in the fold of the catheter balloon relative to the longitudinal direction of the fold. In general the catheter balloon and the release device are fixed during the filling or coating wherein, however, a movement along the longitudinal direction of the fold is possible. If a relative movement is provided the distance for the movement is preferably not larger than the distance between two nozzles or release apertures of the release device.

The release device comprises or consists of at least 2 and maximally 10 release apertures or nozzles or the like, and preferably of 3 to 6 and particularly preferably of 4 or 5 release apertures or nozzles or the like, being preferably evenly distributed over the distance of 10 mm.

The release device has 2 to 10 nozzles or similar apertures being capable of releasing the composition containing an active agent evenly or evenly spraying it into the fold.

In this filling or coating method preferably medium to thin viscous compositions or solutions of an active agent or of a combination of active agents is used which notably contain an alcoholic solvent. Furthermore, coating solutions are preferred which don't harden completely but maintain a gel-like, viscous, oily or pasty consistency. Here also the above statements on the squirting method apply, especially for the coating solution and drying.

In this fold spray method the catheter balloon is packed, i.e. deflated. Even a partial or marginal inflation of the catheter balloon is usually not needed to open the folds slightly. Nevertheless the filling of the folds can be carried out with a marginal inflation of the catheter balloon up to maximally 10% of the diameter provided for dilation. On filling the folds there can be also a slight widening of the folds by applying 100 kPa (1 bar) overpressure, preferably 50 kPa (0.5 bar) for widening the folds slightly.

After filling a fold the catheter balloon is rotated so that the next fold to be filled lies preferably upside and preferably horizontally. The fold filling or coating procedure will now be repeated.

According to the consistency of the composition containing an active agent it may be necessary to dry the previously filled fold before rotating the balloon for filling the next fold. The drying is preferably achieved by evaporation of the solvent.

Furthermore it is also possible in this method to coat or fill concomitantly two, more than two or all folds of a catheter balloon if the consistency of the composition containing an active agent allows for that, i.e. if the consistency is not that fluid that the composition leaks out of the folds which don't lie horizontally. For filling or coating several or all folds an appropriate circular disposition of release devices corresponding to the number of folds is provided and placed onto the preferably vertically oriented catheter balloon, and by rotation the release apertures are directed under the folds where the concomitant release of the composition containing an active agent occurs.

When all folds of the balloon are filled final drying occurs. Basically it is of course not necessary to fill all folds of the fold catheter balloon whereas the filling of all folds, however, is the current and preferred embodiment, since during dilation a preferably maximal amount of active agent shall be transferred onto the vascular wall in a preferably short time.

After filling the last fold drying occurs of the last folds, i.e. of the content of the last fold preferably without vacuum under normal pressure by evaporation of the solvent.

To this preliminary drying a final drying can ensue which according to the invention is carried out on rotating catheter balloons. If required or desired, a vacuum can be applied additionally during rotation. This special drying method is described in more detail in the following of the coating methods according to the invention.

Drag Method or Drop-Drag Method:

A particularly preferred method for overall coating as well as for specific coating or filling of the folds is the so-called drag method or drop-drag method.

This method allows for coating a catheter balloon in its packed state with a fluid composition containing an active agent over the complete surface inside and outside the folding.

In this method a dispensing device in form of a syringe, needle, pipette or nozzle is approached to a preferably horizontally tethered, fix or preferably rotating balloon and then a volume of the composition containing an active agent is dispensed in such a way that at the tip of the dispensing device a drop is formed which contacts the dispensing device as well as the balloon.

For a better performance the dispensing device can be prolonged at the outlet with a thin wire, thread or spongiform tool so that the liquid contact between the dispensing device and the balloon is established and maintained by means of this tool.

Optionally also a dosage needle with a lateral opening or a furcate protruding can be used.

By a lateral movement of the dispensing device along the longitudinal direction of the balloon relative to the rotating balloon the drop is dragged and according to the traced section a certain amount of the composition containing an active agent dries as a thin film on the traced surface. Herein the drop size is maintained by redosing the composition containing an active agent until the final dosage is reached.

The movement is maintained as long as the complete target surface is coated and no fluid is present anymore on the balloon surface.

In order to counteract the capillary effect of the folding at the initial dosis serving for building a drop between the balloon surface and the dispensing device the balloon can be bedewed with a suitable solvent, because thus the folds are already filled with liquid and the capillary effect does not suction the drop.

As most of the tips of dispensing devices are made of harder or hard materials, respectively of a material being redoubtable of damaging the balloon material which may lead to perilous complications during dilation, a particularly preferred embodiment consists in conducting a thread or wire at the tip of the dispensing device through the dispensing device or at least the terminal opening of the dispensing device, or tethering it there, which then serves for contacting the balloon surface without the tip of the dispensing device contacting the balloon. This thread or wire consists of a material that can't damage the balloon material.

Instead of a thread or wire also a sponge or spongiform matter, a piece of textile or a correspondingly thin dimensioned piece of leather, or a bunch of hair or bristles can be used. It is required, however, that these tools consist of materials that don't damage the catheter balloon, i.e. they are not sharp or edged, nor release etching, basic, acid or sticky substances or chemicals which could dissolve completely or partially, decompose, stiffen, scratch or cut the polymer of the catheter balloon.

Thus particularly such substances and polymers are preferred as materials for these tools from which also textiles, threads, yarns, bristles for brushes can be manufactured.

According to the invention it is thus achieved that the tip of the dispensing device can be held at a certain distance to the balloon surface and yet the drop and the movement of the drop relative to the balloon surface can be controlled and regulated via the contacting device in form or a thread, wire, sponge, leather strip, bristle or piece of textile.

Basically it doesn't matter whether the dispensing device is moved with the balloon being stationary or the balloon with a stationary dispensing device. A preferred embodiment consists of a rotating balloon in a horizontal position together with a dispensing device disposed from above and moving along the longitudinal axis of the balloon. In this embodiment a spiral coating of the complete surface of the catheter balloon occurs.

In another preferred embodiment the coating of the catheter balloon in a horizontal position occurs at intervals. The balloon being stationary the dispensing device moves along the longitudinal direction of the catheter balloon in an approximately straight line from one end to the other and back, wherein the balloon is rotated about some degrees when the dispensing device reaches the distal or proximal end of the catheter balloon. A linear coating of the complete balloon surface occurs through this embodiment. If the dispensing device is set however on a fold and it is moved along the fold and this procedure is repeated with the other folds after rotating the balloon a specific fold-filled catheter balloon results.

Thread Drag Method:

In this method no drop is moved over the surface of the catheter balloon but a thread connected with the dispensing device, or serving as a dispensing device, is dragged over the surface of the balloon or set or stippled onto the balloon surface and can serve also in the inoperative state for releasing a solution containing an active agent.

In this procedure a solution containing an active agent flows along the thread wherein preferably no drop is formed. The thread is permanently bedewed with the solution containing an active agent and releases thus solution to the balloon surface as soon as the thread gets in contact with it.

Also this method has the big advantage that the tip of the dispensing device consisting mostly of a hard material doesn't contact the balloon material, similar as in the drop-drag method, and thus no damaging of the catheter balloon occurs.

Preferably, the thread is dragged horizontally along the longitudinal direction while the catheter balloon is rotating, wherein it releases a rapidly drying trace of solution containing an active agent.

This method, however, is not limited to an embodiment with a thread, but also several threads can be moved concomitantly over the balloon surface, wherein in this case the balloon is preferably vertically positioned. Moreover, the threads can also be linked or form a mesh. Herein the threads are linked with at least one dispensing device which continuously provides the threads or the mesh with a solution containing an active agent.

This method thus is suitable for the complete or partial coating of the balloon surface. If only the folds should be filled or coated instead there is the option of inserting a thread at least partially into the fold, or to place it into the fold when folding the balloon, and let the solution containing an active agent flow into the fold by means of this thread, wherein after filling the fold the thread is preferably removed.

Furthermore, for the specific filling of the folds a combination of the pipetting and the thread drag method is particularly suitable, wherein such a big amount of the solution containing an active agent is released from the dispensing device by means of the thread at the proximal or distal end into the unfilled fold of an inflated catheter balloon that the capillary effect suctions the solution into the fold.

The drop-drag method as well as the thread drag method both solve elegantly the problem to coat or fill specifically the balloon surface or specifically the folds of the balloon with a defined amount of active agent without damaging the balloon material. The dispensing device may have a volume measuring device which records or displays the released amount of solution containing an active agent.

Furthermore, these methods are particularly suitable for coating and/or filling the folds of a balloon in the deflated (folded) state which is particularly demanding since the balloon surface of a folded balloon is not even and the common coating methods for regular-shaped bodies can only be applied with corresponding problems. Instead in the drop-drag method or thread drag method differences in distance between the balloon surface and the dispensing device are compensated elegantly by the contacting device in form of a thread, wire, sponge, leather strip, bristle, or piece of textile.

Ballpoint Method or Roll Method:

A preferred variation of the drop-drag method consists of using a spherical coating ball. The ball has such a diameter that it just can't drop out of the outlet of the coating container. It shuts the container completely so that no coating solution can escape between the ball and the vascular wall. When pressure is applied on this ball when contacting the object to be coated the ball moves into the container according to the variably applied pressure and the coating solution can escape between the ball and the vascular wall of the solution container. With a concomitant movement of either the coating container or of the object to be coated and a desired angle between them the ball rolls on the surface and ensures a particularly even coating of the surface. This way different objects can be coated with form fidelity since the ball can trace the surface like a sensor by means of the adjustable pressure and angle and thus provides a particularly high variability in respect of the surfaces to be coated and also of the coating options.

This coating method can be applied excellently especially in catheter balloons since each catheter balloon has a different surface design, is uneven and no balloon surface is equal to another. A preferably optically controlled ballpoint coating method offers the option of coating any different and uneven as well as unequal surface evenly. Furthermore, the ballpoint for transferring the coating solution has the advantage that it doesn't damage the surface of the catheter balloon and the ballpoint respectively the ball can be manufactured of a soft or rubber-like material as e.g. caoutchouc, which is even more saving for the balloon surface in comparison with a metal ball.

Since moreover the ballpoint can be placed very precisely there are controlled starting and end points for the coating. Furthermore the coating device can be designed in such a way that a three-dimensional movement is possible so that the complete catheter balloon can be coated without even once setting off or resetting the ballpoint. After tracing the balloon surface to be coated in a serpentine way the ballpoint of the coating device gets back to the starting point, wherein the initially coated tracks have dried in the meanwhile and a further coating layer can be applied onto the first.

Furthermore a well controllable and even coating results from the roll movement of the ballpoint, wherein the thickness of the coating layer can be controlled via the pressure applied to the ball and the thrust.

Rotation Drying:

As mentioned above the coated or filled catheter balloons can be dried during rotation after coating or filling each fold or after coating or filling all folds or of the folds to be coated or filled if not all folds shall be coated or filled. This is most of the times indicated as step f) in the methods according to the invention.

This rotation drying has several advantages. On the one hand the composition containing the active agent is dried and additionally evenly distributed inside the folds as well as on the surface of the folds.

The rotation drying is particularly suitable for oily or viscous compositions containing an active agent in order to obtain an even distribution of the composition in the respective fold, wherein these coatings in general don't dry but maintain their viscous, oily, gel-like or pasty consistency which is also desired and particularly preferred.

Additionally vacuum can be applied during the rotation of the catheter balloon in order to obtain an intensive drying of the composition containing an active agent.

During drying under vacuum especially in viscous, high viscous or solidifying solutions boiling delays occur, i.e. residuals of the solvent pocketed in the oil or solid are released spontaneously and tear or bust the coating or filling. By drying under vacuum with a concomitant rotation these boiling delays are avoided and a dried and/or oily, viscous, gel-like or pasty even coating within of the folds is obtained.

Moreover, the sense of rotation is crucial. The sense of rotation is in direction of the apertures of the folds when regarding them from the inside of the fold. The catheter balloon is thus rotated like the bucket of a bucket-wheel excavator for pressing the composition containing the active agent into the inside of the folds by means of the rotatory force.

Preferably the fold balloon is rotated with a rotatory velocity of 50 to 500, preferably 150 to 300 cycles per minute.

According to the active agent to be imported into the folds or according to the consistency of the composition containing the active agent to be imported under the folds of a catheter balloon the suitable coating method according to the invention can be selected.

All coating methods according to the invention which enable a specific coating or filling of the folds are suitable, optionally together with a rotation drying method, for obtaining a non-solid but oily, gel-like, pasty or high viscous coating or filling of the folds.

The fold spray method is preferably suitable for thin to medium viscous compositions containing an active agent, while the pipetting method is preferably suitable for light, medium and slightly hard viscous compositions and the squirting method is particularly well applicable for medium viscous, viscous to high viscous compositions.

The term viscosity refers to the dynamic viscosity [□]:

$$[\eta] = \frac{kg}{m \cdot s} = Pa \cdot s = \frac{Ns}{m^2}$$

The squirting method can be preferably used for thick viscous compositions. Preferred are viscosities at room temperature in the range of oils (olive oil: $10^2$ mPa·s), honey ($10^3$ mPa·s), glycerine (1480 mPa·s) or syrup ($10^5$ mPa·s). This method works of course also in thin viscous solutions with □≤$10^2$ mPa·s.

The pipetting method can be used preferably in medium viscous solutions. Preferred are viscosities at room temperature in the range of 0.5 mPa·s to 5000 mPa·s, more preferred in the range of 0.7 mPa·s to 1000 mPa·s, even more preferred in the range of 0.9 mPa·s to 200 mPa·s and particularly preferred in the range of 1.0 mPa·s to 100 mPa·s. In this viscosity range oils, contrast media and/or salts can be found which are diluted with common solvents, especially alcohols. The pipetting method can be used over a very broad viscosity range.

The fold spray method is preferably used in thin viscous compositions. Preferred are viscosities at room temperature in the range of 0.1 mPa·s to 400 mPa·s, more preferred in the range of 0.2 mPa·s to 100 mPa·s and particularly preferred in the range of 0.3 mPa·s to 50 mPa·s (water: 1.0 mPa·s; kerosene: 0.65 mPa·s; pentane: 0.22 mPa·s; hexane: 0.32 mPa·s; heptane: 0.41 mPa·s; octane: 0.54 mPa·s; nonane: 0.71 mPa·s; chloroform: 0.56 mPa·s; ethanol: 1.2 mPa·s; propanol: 2.3 mPa·s; isopropanol: 2.43 mPa·s; isobutanol: 3.95 mPa·s; isotridecanol: 42 V mPa·s).

Coated Catheter Balloons

According to the methods disclosed herein catheter balloons without a stent and partially also with a stent can be coated so that the present invention relates to coated catheter balloons which can be obtained by the methods described herein.

A particularly preferred embodiment uses a catheter balloon with a crimped stent. These stents can be bare non-coated (bare) stents or preferably stents coated with only one hemocompatible layer. As hemocompatible layer particularly the heparin and chitosan derivatives disclosed herein are preferred and primarily desulfated and reacetylated or re-proprionylated heparin.

Moreover, there is the option of applying under and/or on the layer containing the transport mediator yet one or more layers of pure active agent or a polymer or polymer containing an active agent.

On using the fold balloons which form folds when being packed they can be filled with active agent and transport mediator. Particularly the pipetting method is suitable therefore.

A possibly present solvent can be removed under diminished pressure, thus drying the mixture inside the folds. On dilating such a balloon which in general is used without a stent the folds turn or bulge to the outside and thus release their content to the vascular wall.

The methods according to the invention are suitable for the coating of guide wires, spirals, catheters, cannulae, tubes and generally tubular implants or parts of the aforementioned medical devices if a structural element similar to a stent is contained in such a medical device that shall be coated or filled. Stents and especially such as coronary, vascular, trachea, bronchia, urethra, oesophagus, gall, kidney, small intestine, colon stents for example can be coated.

The coated medical devices are particularly used for keeping all duct-like structures open, for example of the urinary tract, oesophagus, trachea, bile duct, renal tract, blood vessels in the whole body including the brain, duodenum, pylorus, small and large intestine, but also for keeping open artificial outlets, as being used for the intestine or the trachea.

Thus the coated medical devices are suitable for the prevention, reduction or treatment of stenoses, restenoses, atherosclerosis and all other forms of occluded vessels or stenoses of passages or outlets.

The balloon catheters according to the invention without a stent are particularly suitable for the treatment of in-stent stenosis, i.e. or the treatment of recurring vessel stenoses inside an already implanted stent which preferably is not bioresorbable. In such in-stent restenoses the placement of another stent inside the already existing stent is particularly problematic as the vessel in general can only poorly be widened by the second stent. Herein the application of an active agent by means of balloon dilation offers an ideal treatment method since this treatment can be repeated several times, if necessary, and from a therapeutic point of view may obtain the same or significantly better results than another stent implantation.

Furthermore the catheter balloons according to the invention without a crimped stent are particularly suitable for the treatment of small vessels, preferably small blood vessels. Small vessels refer to those vessels with a vessel diameter less than 2.5 mm, preferably less than 2.2 mm.

To resume, for the use of selected matrices and excipients the following applies:

The abovementioned matrices and excipients as well as their mixtures and combinations preferably have at least one of the following characteristics for successful local application of one or more active agents:
1) the exposure time of the short-term implant is sufficient for the transfer of a suitable therapeutic amount of the active agent into the cells,
2) during exposure a sufficient amount of coating material containing the active agent adheres to the vascular wall for ensuring the desired therapeutic effect, and it is particularly preferred
3) that the coating containing the active agent and present on the short-term implant displays a higher affinity to the vascular wall than to the surface of the implant so that an optimal transfer of the active agent onto the target can occur. This works excellently mainly for pasty, gel-like or oily coatings.

Of course in all cases a coated or uncoated stent can build a system with the balloon catheter, depending on the individual requirements. Likewise other excipients as e.g. the imaging agents can be added, if needed.

For example the exposure time of the particularly preferred embodiment of a balloon catheter coated by the spray method with paclitaxel is already sufficient for applying a therapeutic amount of paclitaxel which was sedimented amorphously by the spray method onto and into the cell wall. Here, a stent rendered hemocompatible with a semi-synthetic oligosaccharide and likewise coated with paclitaxel serves as a store for the elution of further amounts of active agent provided for a longer time span.

Because of the amorphous consistency of paclitaxel on the stent and the catheter balloon obtained from the special spray method paclitaxel is not flushed or washed away from the surface during the introduction of the catheter so that the desired amount of active agent reaches its target and is released there by dilation to the vascular wall. Because of the concomitant coating of the stent and the catheter balloon the vessel is completely covered with active agent. It is preferred further that the catheter balloon is also coated with paclitaxel in the sections extending the stent ends so that a supply of the vessel with paclitaxel (or instead of paclitaxel any other active agent) occurs also in the section of the stent ends and beyond for 1 to 3 mm in proximal and distal direction. Also here the amorphous structure of paclitaxel is of uttermost importance because only thereby the surface of the layer with the active agent is thus enlarged that an optimal amount of the active agent adheres to the cell wall and can enter the cell wall respectively the cells.

The addition of a vasodilator directly acting on the cell wall or of a carrier easily permeating the membrane (e.g. DMSO, PETN, lecithin) can still enhance significantly the uptake into the cells during an accumulated exposure time of preferably 30 to 300 seconds.

In another particularly preferred embodiment of substance-eluting balloon catheter the active agent is solved together with a hydrophobic long-chained fatty acid, e.g. isopropyl myristate, in a suitable solvent and applied to the surface of the catheter balloon. For coating all coating methods described in the following are suitable. The addition of the fatty acid enables the transfer of the coating material from the surface of the catheter onto the vascular wall, wherein the amount of the transferred substance-eluting matrix is sufficient to provide the active agent in a sufficient concentration as well as to prevent that the matrix is instantaneously washed away in the blood stream.

A further particularly preferred embodiment consists in the use of mixture with high affinity to the cell wall of the polysaccharide carrageenan, phosphatidylcholine, one of the major components of cell membranes, as a membrane-permeating substance and glycerine that because of its excellent adhesive properties allows for a delayed release of the active agent of up to 12 hours after dilating the vessel. All coating methods are suitable for this embodiment, particularly preferred are the pipetting, thread drag and ballpoint method described herein.

EXAMPLES

Example 1

Figure 1:
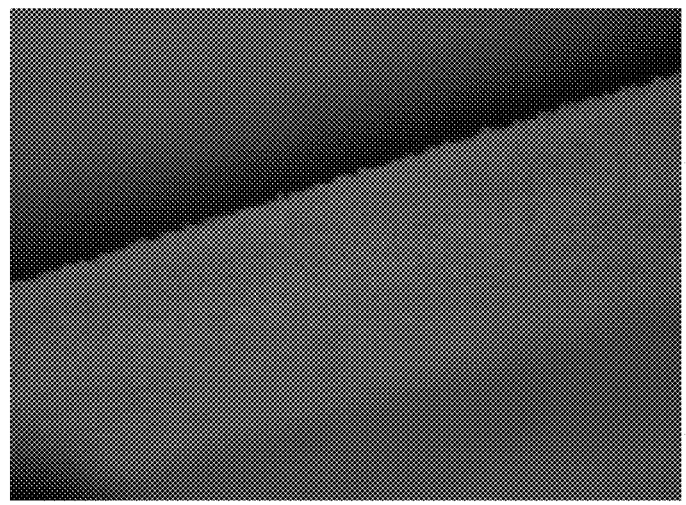
FIG. 1 shows a balloon catheter coated with paclitaxel in PEG (amplification 80×).
Figure 2:
FIG. 2 shows a balloon catheter coated with paclitaxel in ethanol (amplification 40×).
Figure 3:
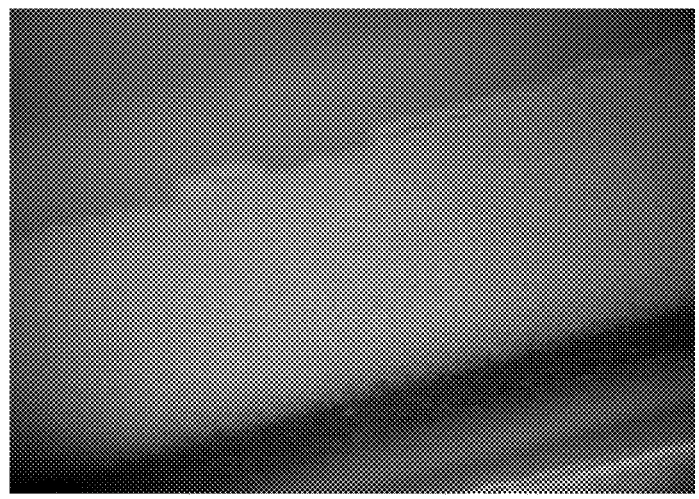
FIG. 3 shows a balloon catheter coated with paclitaxel and PVP after expansion (amplification 80×).
Figure 4:
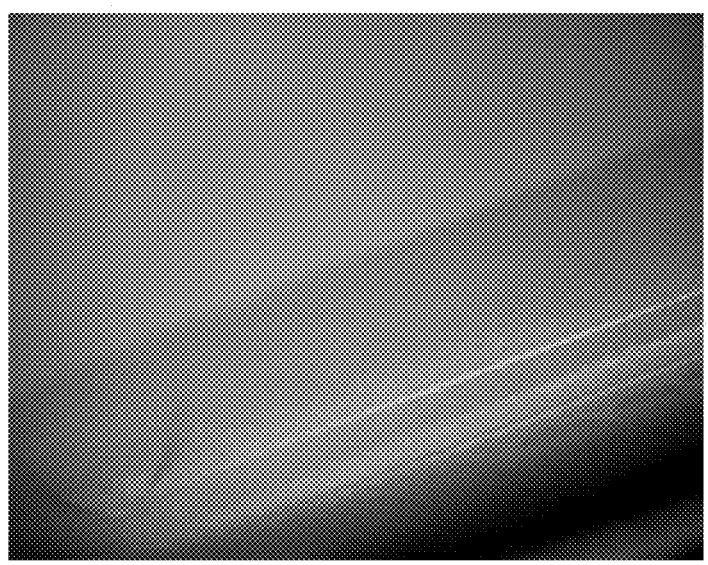
FIG. 4 shows a 4*20 mm balloon with paclitaxel in chloroform low dose after expansion (amplification 40×).
Figure 5:
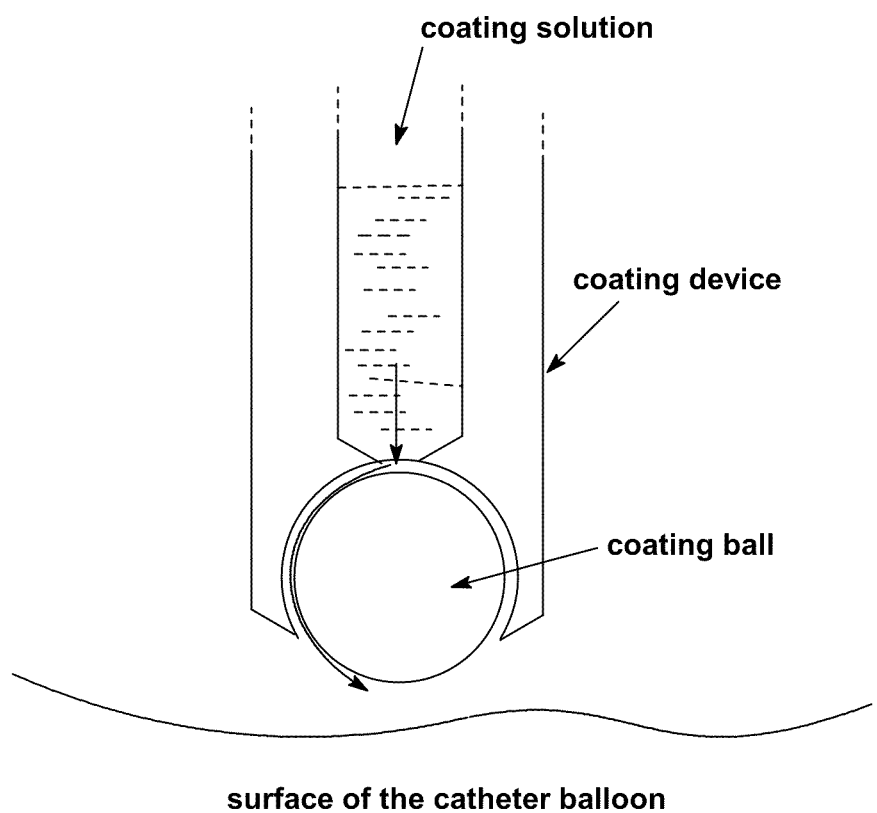
FIG. 5 shows a coating device according to the ballpoint method, wherein the coating solution is inside the coating device and is released via a rotatable ball onto the surface to be coated.

A gene encoding for hemoxygenase HO-2 is embedded in pAH 9 vector. The plasmids are stored in lipid vesicles by using di-ethers or tetra-ethers. To the resulting emulsion a biopolymer paclitaxel or rapamycin are added. As biopolymers heparin, heparan sulfates or derivatives of heparin or heparan sulfates such as desulfated heparin are used.

After adding desulfated heparin the thin viscous mixture is first applied via dipping method on a catheter balloon in its packed form. Therefore the catheter balloon is inserted vertically into the dipping solution and slowly (v<1 mm/s) and vertically pulled out of the solution so that an equal bubble-free film can form on the surface of the catheter.

After a short drying time of max. 30 minutes particularly the folds are refilled again with the pipetting method to ensure a complete coating and an optimal loading of the balloon catheter with rapamycin. To this end the coated balloon catheter is disposed on a rotation motor with a tilt angle of 25° in such a way that the balloon catheter cannot bend. The dosage syringe ending in a blunt cannula is positioned in such a way that it is inserted from the superior fold end into the fold and a defined amount of the coating solution is released into the fold.

After filling the fold the balloon catheter is rotated about its longitudinal axis after waiting for up to 30 sec., so that the next fold can be filled.

By aid of the tilt angle the capillary effect and gravitation can be used to fill the fold completely or partially, according to the desired rapamycin dosage.

At the moment of dilating the balloon in the interior of the vessel the liposome complexes contact the cell wall and fusion with the lipophilic cell membrane. In the cell endosomes transport the lipoplexes to the nucleus. The inducible DNA is not incorporated into the chromosomal DNA of the cell but remains active in the nucleus as independent so-called episomal plasmid DNA. A section of the plasmid DNA shaped as a promoter starts the synthesis of hemoxygenase 1 which then produces CO.

Example 1a)

The complete and equal coating of the folds is possible by mounting the balloon catheter to the rotation motor in such a way that it is tethered horizontally without bending or sagging. The fold to be coated lies upside so that it can't bend sideways.

Now the coating cannula is positioned in such a way that it captures the fold during the movement from the proximal to the distal end and back in such a way that only that part of the fold material is lifted that is filled concomitantly with the coating solution during the movement of the cannula along the fold.

Thus an even distribution of the coating solution is obtained from the beginning to the end of the fold.

The velocity with which the cannula moves horizontally along the fold and the depth of penetration into the fold are thus adjusted, that the fold closes evenly after the filling step.

The drying of the balloon catheters filled in such a way is achieved by rotation drying at room temperature.

Example 2

NO synthase III is produced recombinantly according to the protocol in Biochemistry 2002. 30, 41(30), 9286-9830 and MPM1 Vol. 16, No. 12, 2003, pp. 1094-1104.

The recombinant NOS III is solved in a predominantly aqueous medium. Co-solvents up to 15 vol. %, preferably up to 9 vol. %, can be added to the watery solution. As co-solvents tetrahydrofuran (THF), propanol, isopropanol, ethanol, methanol, dimethyl formamide (DMF), dimethyl sulfamide (DMSO), acetone or acetic acid are suitable.

Furthermore, an excess of L-arginine as well as 15 mg simvastatin per ml solution are added to the watery solution with 10 vol. % DMSO.

A biologically degradable polymer is added to the resulting solution. Preferred resorbable polymers are polymethylmethacrylate (PMMA), polytetrafluoroethylene (PTFE), polyurethanes, polyvinyl chloride (PVC), polyvinyl pyrrolidones, polyethylene glycols, polydimethyl siloxanes (PDMS), polyesters, nylons, polyethylene oxide and polylactides. Particularly preferred are polyvinyl pyrrolidones, polyethylene glycols, polyesters, polylactides as well co-polymers of diols and esters, respectively diols and lactides. As diols ethane-2-diol, propane-1,3-diol or butane-1,4-diol are used for example.

In the present case polyvinyl pyrrolidone and fasudil are added to the aqueous solution so that a 1% polymer-containing viscous solution results. A catheter balloon with a crimped stent is coated several times completely with this solution by means of the thread drag method.

The balloon catheter with the crimped stent is mounted via an adapter onto the drive shaft of the rotation motor and tethered in such a way that it is positioned horizontally without bending. Through a dosage needle and the welded on drag wire one drop of solution is dragged over the rotating balloon until a coherent coating forms. After that the still rotating catheter/stent system is exposed to a slight warm airflow for a preliminary drying so that a high viscous non-fluid surface forms. Subsequently it is dried at room temperature.

The stent as well as the coating can be resorbable and can be degraded slowly after incorporation into the cell wall. Especially during the first 10 days after implantation NOS III provides a sufficient amount of NO which positively influences and regulates the healing process of the cell wall and the cell growth.

Example 3

A catheter balloon is coated with a biostable coating of cellulose nitrate via the drop-drag method.

For this purpose the catheter is fixed into the adapter of the rotation motor in such a way that he is tethered horizontally without a bending or sagging being possible. The dispensing device is tethered over the balloon in such a way that the distance of the pipette through which the coating solution escapes has just the size that the escaping drop contacts the surface of the balloon without detaching from the pipette tip. The velocity by which the coating solution escapes is adjusted in such a way that the drop cannot pull off during the longitudinal movement of the catheter balloon. When the upper surface of the balloon is coated completely in such a way the balloon is rotated so far that the adjacent sector can be coated in the same longitudinal direction. The procedure is repeated as often until the balloon catheter has performed a complete cycle.

On this layer the enzyme NOS III or HO-1 is immobilized by cross-linking it with glutardialdehyde after the application. Nevertheless the enzyme keeps a sufficient degree of activity for building CO respectively NO after the implantation of the stent.

On this layer a pure layer of active agent out of paclitaxel is applied.

If necessary the paclitaxel substance layer may be coated with a barrier layer of polylactides, polyglycolides, polyanhydrides, poyphosphazenes, polyorthoesters, polysaccharides, polynucleotides, polypeptides, polyolefins, vynylchloride polymers, fluorine-containing polymers, teflon, polyvinylacetates, polyvinylalcohols, polyvinylacetals, polyacrylates, polymethacrylates, polystyrene, polyamides, polyimides, polyacetals, polycarbonates, polyesters, polyurethanes, polyisocyanates, polysilicones as well as co-polymers and mixtures of these polymers.

Example 4

A hemoglobin derivative is produced according to embodiment 1 or 2 of WO 02/00230 A1. The resulting hemoglobin polymer was used in three series of experiments.

One fraction of the hemoglobin polymers was saturated with CO. Another fraction was saturated with NO and the remaining fraction was saturated with a mixture of CO and NO, Thereafter the active agent paclitaxel was added to each fraction.

A catheter balloon was coated with a biostable polymer coating. In the present case a polyvinyl ester was used as biostable polymer. On this polymeric layer the CO-saturated hemoglobin polymers were applied by means of the spray method under CO atmosphere, dried and stored under CO atmosphere.

The NO saturated hemoglobin polymers were used for coating a catheter balloon together with a crimped cobalt/chromium stent. To this end the NO saturated hemoglobin polymers were mixed in an aqueous solution together with a polylactides, paclitaxel was added applied onto the balloon including the stent via the roll method, wherein he roll and the drying method were repeated three times each. The coating procedure was carried out under argon as inert gas and the catheter balloons including the stents were then stored under argon.

The balloon catheter with the crimped stent is fixed in a horizontal position. The dispensing device for the coating solution is disposed such a way that it can be moved along the longitudinal direction of the catheter and vertically to it. Herein the vertical movement is controlled via a fix application of pressure to the ball in such a way that the pressure through the contact with the surface to be coated on the ball of the outlet is always exerted equally and thus always the same amount of the coating solution escapes. This ensures that during the same time always the same amount of coating solution is applied onto the surface of the catheter balloon as well as of the stent and the stent spacings.

During the coating the ball is pressed in corresponding to the adjusted pressure when contacting the surface to such a degree that the solution escapes of the outlet along the ball. Through a concomitant even movement of the catheter/stent in the longitudinal direction the ball is moved and distributes the coating solution evenly on the surface by the roll movement.

The tracing of the surface us carried out under a concomitant slight rotation of the catheter about its longitudinal axis so that the coating of the complete surface of the catheter can be carried out without interrupting the roll movement of the ball-shaped outlet.

The NO and CO saturated hemoglobin polymers were mixed in an aqueous solution together with a polyglycolide and paclitaxel and then used as a high viscous spray solution for the specific coating of the folds of a catheter balloon. To this end the balloon is tethered horizontally and inflated to such a small degree that the folds start opening. By means of a nozzle the coating solution can now be applied in an adjusted dispense amount along the fold at the bottom of the fold while the balloon catheter rotates about its longitudinal axis. Since the coating paste sticks to the bottom of the fold the balloon catheter can be safely rotated immediately after filling each fold for filling the next fold.

After removing the slight overpressure the folds can be brought back into their initial position. A drying procedure is not necessary in this example.

Example 5

In another embodiment of the present invention CO or NO or a mixture of CO and NO is released from the inside of the catheter balloon through a plurality of micro- and nano-pores during dilation and on the one hand supports the detachment of the coating on the catheter balloon from the balloon surface during dilation and on the other hand the uptake of the active agent in the coating on the balloon surface into the vascular wall as a vasodilator. On the balloon surface there is preferably a polymeric coating containing one or more active agents which counteract or prevent a re-occlusion or a restenosis of the vessel.

Example 6a

The balloon catheter is coated all over with an alcoholic solution of an iodine-containing contrast medium and paclitaxel (respectively another active agent or combination of active agents) via the thread drag method.

For this end a 2% solution of contrast medium is produced in which such an amount of paclitaxel is solved that a 30% solution of the active agent results.

The balloon is coated completely with this solution and then dried under slow rotation about the longitudinal axis at room temperature for at least three hours. This procedure is repeated at least one time.

After complete drying the balloon catheter coated such a way with active agent is coated with a 1% PVA solution, for example with a topcoat, in the same way or by another suitable method such as the roll method.

Example 7a

The fold balloon expanded to nominal pressure is dipped into a 1% dipping solution of paclitaxel and chloroform for 5-10 s and subsequently dried under rotation about the longitudinal axis to such a degree that the major portion of the chloroform has evaporated. Before a complete drying the balloon is deflated again in the air stream.

Example 7b

The fold balloon is tethered in a horizontal position on the rotatable axis so that the fold to be filled is always lying upside. Thus step by step each fold is filled with a solution containing an active agent (e.g. from example 17) which displays a honey- or syrup-like viscosity (viscosities from $10^2$ to $10^5$ mPa·s) from the beginning to the end of the fold by means of a teflon cannula as enlargement of a needle syringe.

For this end the teflon cannula is conducted to the centre of the cavity formed by the fold, and during the movement of the horizontally tethered catheter in its longitudinal direction a defined amount of a high viscous solution is released into the fold cavity (squirting method). The amount of the filled material is limited in such a way that the fold doesn't lift from the balloon body after filling and varies corresponding to different balloon dimensions and manufacturers.

Example 7c

The balloon from Example 7a, loaded with active agent and re-deflated like the fold balloon from Example 7b partially loaded with active agent, can be coated in a second step through the spray method with a polymeric outer layer as a barrier. For this end the concentration of the polymeric spray solution must be kept so small that the polymeric layer obtained after drying does not hamper a regular unfolding. For example, a 0.5% PVP solution is already apt therefore.

Example 8

A catheter balloon is coated with a layer of pure active agent of paclitaxel. Then the catheter balloon is provided with a protective wrapper for preventing premature detachment of the active agent, as used in self-expanding Nitinol stents. The protective wrapper can be removed in vivo immediately before dilation.

Example 9

A solution of desulfated heparin is prepared in a methanol/ethanol mixture and acidified with acetic acid so that a pH value of 3 to 5 results. Paclitaxel is added to this solution. A catheter balloon is coated with this solution and subsequently a slight cross-linking of the dried coating on the balloon with glutaraldehyde is carried out.

Example 10

A conventional catheter balloon is preferably coated in a first step with a lubricant such as graphite or a stearate, and subsequently coated preferably by the squirting method with a viscous mixture of an oil or fat and an active agent such as rapamycin or paclitaxel.

If necessary, a slight hardening can be performed by autopolymerization initiated by oxygen molecules or radiation and/or radical formers. Thus a smooth surface results on the surface of the catheter balloon which in general doesn't need further protection from premature detachment. The catheter balloon can be advanced in its present form to the stenotic section of the vessel and there the transfer of the coating onto the vascular wall can be effected by dilating the balloon, wherein the lubricant directly on the balloon surface promotes the detachment of the oily coating.

Example 11

Magnetic particles in the nanometer to micrometer range with an iron-containing core are provided according to known methods with an outer shell containing carboxyl groups. Paclitaxel is added to these magnetic particles in a methanol/ethanol mixture and then the alcoholic solution is used for coating the catheter balloon.

The coating solution can be applied by the spray method because of its low viscosity. If preferably the folds of a balloon are coated with this solution the fold spray method is particularly suitable. If a dispense through several nozzles is performed concomitantly so that the fold is sprayed concomitantly along its entire fold length a preliminary drying can occur when working in a warm gentle airstream so that all folds of the balloon can be coated in the shortest time. Then a rotation drying occurs.

On dilating the coated catheter balloons an external magnetic field is applied which immobilizes the magnetic particles at the stenotic section and thus fosters the uptake into the smooth muscle cells.

Example 12

Magnetic ferrite particles are provided with an organic shell containing the active agent paclitaxel. The magnetic particles are applied on a catheter balloon in the interior of which a magnetic field can be generated for immobilizing the magnetic particles.

On dilating the catheter balloon the magnetic field is reversed in polarity and thus leads to a repulsion of the magnetic particles from the balloon surface and to an enhanced uptake into smooth muscle cells.

Example 13

Paclitaxel is solved in DMSO containing ca. 10 vol. % water. Potassium oxalate, sodium chloride, glutaminic acid and oxalic acid are added to this solution and the catheter balloon is coated several times with this solution by using the thread drag method and dried after the coating. Subsequently, the coated catheter balloon is provided with a biodegradable layer of a lactam.

Example 14

A mixture of sodium stearate, potassium valerate, malonic acid and paclitaxel in ethylene glycol, ethanol and water is prepared, filled into a pipette and squirted by means of the pipette under the folds of a fold balloon. After drying a powdery coating of the fold interspaces results, which is easily detached on dilating the balloon.

Example 15

Paclitaxel is mixed with magnesium sulfate, potassium chloride, lithium chloride and sodium acetate and worked up to a paste by adding an alcoholic solvent, and for dilution possibly a contrast medium, which then is filled into a syringe and is squirted under the folds of a fold balloon and is going to dry there in the air until a brittle coating results. During coating the tip of the squirting nozzle traces along the fold applying a layer of paste in the fold along the longitudinal direction of the fold.

Example 16

A thin viscous alcoholic solution of paclitaxel is prepared which is so thin viscous that the solution is dragged into the folds by itself through capillary forces. By means of a capillary set on an end of the fold the alcoholic paclitaxel solution is let to flow into the fold until the inner space of the fold is filled completely by capillary forces. The content of the fold is left for drying, the balloon is rotated and the next fold filled. Each fold is filled only once.

Example 17

A mixture of 70% linseed oil and 30% olive oil is prepared. This mixture is solved in a ratio of 1:1 in chloroform and after adding paclitaxel (25 weight percentage) applied onto an evenly rotating catheter balloon by means of the roll method. After evaporating chloroform in a gentle airstream the balloon catheter is stored in a drying closet at 70° C. so that a surface is provided which is already adhesive but smooth, highly viscous and thus not impeding on expanding the balloon.

Example 18

A cobalt/chromium stent is crimped into a catheter balloon of polyamide.

Now a solution of paclitaxel in DMSO is applied onto the stent by means of a syringe. The solution is so thin viscous that it flows between the closely fitting struts of the stent and fills the interspaces between the balloon surface and the inner surface of the stent as well as between the single struts of the stent. The solvent evaporates and the pure active agent sediments as a solid onto the catheter balloon under the stent, in the stent interspaces and on the stent and the balloon surface. The catheter balloon is coated with active agent at both ends of the stent for ca. 2 to 3 mm beyond the stent ends.

Example 19

A rapamycin solution is prepared in ethanol and the solution is sprayed several times on a catheter balloon without a stent, the catheter balloon is dried in the meantime by letting the solvent evaporate.

After repeating the spray coating three times the catheter balloon is finally dried and an uncoated metal stent is crimped onto the balloon.

Example 20

A commercially available catheter balloon is coated with an amount of 3 µg paclitaxel per $mm^2$ balloon surface. The coating is done with the pipetting method by using a solution of paclitaxel in DMSO. The DMSO solution may additionally contain salts up to 1 mg per ml, such as sodium acetate and preferably acid as well as neutral amino acids. Then the uncoated cobalt/chromium metal stent is crimped onto the coated catheter balloon.

Example 21

A catheter balloon with a crimped uncoated metal stent is coated with a solution of paclitaxel in DMSO by means of the drop-drag method. The coating procedure is repeated three to four times until the interspaces between the balloon surface and the inner surface of the stent as well as the interspaces of the single struts of the stent are visibly filled with active agent.

If desired, a protective layer of a polylactide for example can be applied additionally onto the layer with the active agent paclitaxel.

Example 22

A commercially available catheter balloon is coated with a dispersion of paclitaxel in acetic acid ethyl ester with 5 vol. % acetic acid so that an amount of 2-3 µg paclitaxel per $mm^2$ balloon surface results. A bioresorbable stent of polyhydroxybutyrate is crimped onto the coated balloon surface.

Example 23

Onto a catheter balloon coated in its folds with paclitaxel via the capillary method and having an amount of 1-2 µg paclitaxel per $mm^2$ fold a titanium stent is crimped which is coated with a polymeric carrier system of a polyether sulfone containing the active agent paclitaxel in a preferably cytostatic dosage. The titanium stent was previously coated with a solution of paclitaxel and the polyether sulfone in methylene chloride via the pipetting method. On the titanium stent there are ca. 0.5 µg paclitaxel per $mm^2$ stent surface.

Example 24

A catheter balloon coated with rapamycin embedded in a polylactide-polyglycolide polymer is provided. Now a bioresorbable stent of polylactide is crimped onto this catheter balloon which is coated with polylactide containing paclitaxel in an amount of ca. 1.0 µg per $mm^2$ stent surface.

Example 25

A non-dilated fold balloon is coated completely with an active agent and an excipient as carrier by means of the described pipetting method.

For this end 150 mg sirolimus are solved in 4.5 ml acetone and mixed with a solution of 100 µl isopropyl myristate in 450 µl ethanol. After applying the solution the fold balloon is dried over night.

Example 26

The fold balloon coated according to Example 25 is introduced into a PBS filled silicon tube and then expanded to nominal pressure for 60 sec.

Subsequently, the sirolimus content remaining on the balloon catheter, the portion solved in the PBS buffer and the content of active agent adhering to the inner surface of the tube are determined after extraction with acetonitrile by means of HPLC measurement:

| Determining the sirolimus content after expanding the fold balloon by means of HPLC measurement [in %] | | |
| --- | --- | --- |
| on the fold balloon | in PBS buffer | on the inner surface of the tube |
| 35.2% | 17.3% | 47.5% |

Example 27

Coating of a Catheter with the Thread Drag Method

When initiating the rotation of the catheter a slight negative pressure is drawn upon the balloon so that the folds don't bend during the rotational movement of the balloon about its own longitudinal axis. Subsequently the balloon is pre-bedewed with the wetting solution. Immediately after the coating procedure is carried out. A drop of solution is dragged over the balloon through the dispensing needle and the welded on dragging wire until the solvent evaporates to such a degree that a solid coating is formed.

After ending the adjusted overcoatings the catheter keeps on rotating for some seconds. Subsequently the catheter is removed from the device and dried at room temperature.

Example 28

Covalent Hemocompatible Coating of Stents

Non-expanded cleansed stents of medical stainless steel LVM 316 are dipped into a 2% solution of 3-aminopropyltriethoxysilane in an ethanol/water mixture (50/50 (v/v)) for 5 minutes and subsequently dried. Then the stents are washed over night with demineralised water.

3 mg desulfated and reacetylated heparin are solved in 30 ml 0.1 M MES buffer (2-(N-morpholino)ethane sulfonic acid at pH 4.75 and then 30 mg N-cyclohexyl-N'-(2-morpholinoethyl)carbodiimide-methyl-p-toluol sulfonate are added. The stents are stirred in this solution over night at 4° C. Subsequently they are washed intensively with water and 4M NaCl solution.

Example 29

The cleansed respectively covalently coated stents are crimped onto the balloon catheter and coated together with a spray solution containing an active agent by means of the thread drag method.

Preparation of the spray solution: 44 mg taxol are solved in 6 g chloroform.

Example 30

Coating of a Hemocompatibly Furnished Stent with a Matrix Containing an Active Agent by Means of the Roll Method Coating solution: a polylactide RG5032/taxol solution of 145.2 mg polylactide and 48.4 mg taxol are filled up to 22 g with chloroform.

Example 31

Coating of the all-in System Stent+Balloon with a Matrix Loaded with Active Agent as Basic Coat and the Active Agent as Top Coat Basic coat: 19.8 mg linseed oil and 6.6 mg taxol are filled up to 3 g with chloroform Top coat: 8.8 mg taxol are filled up to 2 g with chloroform The balloon catheter with a crimped stent is coated with the basic coat by means of the drop-drag method. As soon as this basic coat becomes a high viscous film by evaporation of the solvent on the system surface the second layer with the pure active agent can be sprayed on.

Example 32

Coating of a Balloon Catheter with a Cell Affine Matrix Containing an Active Agent The balloon catheter is mounted by means of an adapter onto the drive shaft of a rotation motor and fixed in such a way that it stays in a horizontal position without bending. After applying a slight negative pressure on the balloon the balloon is coated with the solution according to the adjusted number of balloon tracings.

Coating solution: Carrageenan, phosphatidylcholine and glycerine (1:2:2) are solved in ethanol/water (1:1; v:v)

Thread Drag Method:

A drop of solution is dragged over the rotating balloon through the dispensing needle and the welded on drag wire until the solvent is evaporated that much that a solid coating has formed. Subsequently, the catheter is removed from the device and dried over night at room temperature under continuous rotation.

The invention claimed is:

1. A catheter balloon coated with a coating, the coating consisting of:
paclitaxel and at least one citrate ester.

2. A catheter balloon according to claim 1, wherein the citrate ester is tributyl citrate, triethyl citrate, acetyl tributyl citrate, acetyl triethyl citrate, or a mixture thereof.

3. A method of treating a patient to lessen occurrence of restenosis at a vascular site, comprising advancing a catheter having a balloon having a coating consisting of an antiproliferative active agent and a member of the group consisting of triethyl citrate, triethyl citrate acetylate, tributyl citrate, and tributyl citrate acetylate to a treatment site of a vessel wall and inflating the balloon to contact the vessel wall and transfer at least some of the antiproliferative active agent to the vessel wall, wherein the antiproliferative active agent is paclitaxel.

4. A method as in claim 3 wherein the member is tributyl citrate acetylate.

5. A method of treating a patient to lessen occurrence of restenosis at a vascular site, comprising advancing a catheter having a balloon having a coating consisting of an antiproliferative active agent and a citrate ester to a treatment site of a vessel wall and inflating the balloon to contact the vessel wall and transfer at least some of the antiproliferative active agent to the vessel wall, wherein the antiproliferative active agent is paclitaxel.

* * * * *